(12) United States Patent
Dongsheng et al.

(10) Patent No.: US 8,236,557 B2
(45) Date of Patent: Aug. 7, 2012

(54) HYBRID-AAV VECTORS TO DELIVER LARGE GENE EXPRESSION CASSETTE

(75) Inventors: Duan Dongsheng, Columbia, MO (US); Arkasubhra Ghosh, Singapore (SG); Yongping Yue, Columbia, MO (US)

(73) Assignee: University of Missouri-Columbia, Columbia, MO (US)

( * ) Notice: Subject to any disclaimer, the term of this patent is extended or adjusted under 35 U.S.C. 154(b) by 511 days.

(21) Appl. No.: 12/473,651

(22) Filed: May 28, 2009

(65) Prior Publication Data

US 2010/0003218 A1 Jan. 7, 2010

Related U.S. Application Data

(60) Provisional application No. 61/130,087, filed on May 28, 2008.

(51) Int. Cl.
*C12N 15/86* (2006.01)
*A01N 63/00* (2006.01)

(52) U.S. Cl. .................................. 435/320.1; 424/93.2

(58) Field of Classification Search .................. None
See application file for complete search history.

(56) References Cited

U.S. PATENT DOCUMENTS 7,892,824 B2 * 2/2011 Duan et al. ................. 435/320.1

OTHER PUBLICATIONS

Acsadi, G., G. Dickson, D. R. Love, A. Jani, F. S. Walsh, A. Gurusinghe, J. A. Wolff, and K. E. Davies. 1991. Human dystrophin expression in mdx mice after intramuscular injection of DNA constructs [see comments]. *Nature* 352:815-8.
Albrecht, D. E., and S. C. Froehner. 2002. Syntrophins and dystrobrevins: defining the dystrophin scaffold at synapses. *Neurosignals* 11:123-9.
Alter, J., F. Lou, A. Rabinowitz, H. Yin, J. Rosenfeld, S. D. Wilton, T. A. Partridge, and Q. L. Lu. 2006. Systemic delivery of morpholino oligonucleotide restores dystrophin expression bodywide and improves dystrophic pathology. *Nat Med* 12:175-7.
Beggs, A. H., E. P. Hoffman, J. R. Snyder, K. Arahata, L. Specht, F. Shapiro, C. Angelini, H. Sugita,and L. M. Kunkel. 1991. Exploring the molecular basis for variability among patients with Becker muscular dystrophy: dystrophin gene and protein studies. *Am J Hum Genet* 49:54-67.
Bilbao, R., D. P. Reay, E. Wu, H. Zheng, V. Biermann, S. Kochanek, and P. R. Clemens. 2005. Comparison of high-capacity and first-generation adenoviral vector gene delivery to murine muscle in utero. *Gene Ther* 12:39-47.
Brenman, J. E., D. S. Chao, S. H. Gee, A. W. McGee, S. E. Craven, D. R. Santillano, Z. Wu, F. Huang, H. Xia, M. F. Peters, S. C. Froehner, and D. S. Bredt. 1996. Interaction of nitric oxide synthase with the postsynaptic density protein PSD-95 and alpha1-syntrophin mediated by PDZ domains. *Cell* 84:757-67.
Brenman, J. E., D. S. Chao, H. Xia, K. Aldape, and D. S. Bredt. 1995. Nitric oxide synthase complexed with dystrophin and absent from skeletal muscle sarcolemma in Duchenne muscular dystrophy. *Cell* 82:743-52.
Bulman, D. E., E. G. Murphy, E. E. Zubrzycka-Gaarn, R. G. Worton, and P. N. Ray. 1991. Differentiation of Duchenne and Becker muscular dystrophy phenotypes with amino- and carboxyterminal antisera specific for dystrophin. *Am J Hum Genet* 48:295-304.
Chao, D. S., J. R. Gorospe, J. E. Brenman, J. A. Rafael, M. F. Peters, S. C. Froehner, E. P. Hoffman, J. S. Chamberlain, and D. S. Bredt. 1996. Selective loss of sarcolemmal nitric oxide synthase in Becker muscular dystrophy. *J Exp Med* 184:609-18.
Chapman, V. M., D. R. Miller, D. Armstrong, and C. T. Caskey. 1989. Recovery of induced mutations for X chromosome-linked muscular dystrophy in mice. *Proc Natl Acad Sci USA* 86:1292-6.
Clemens, P. R., S. Kochanek, Y. Sunada, S. Chan, H. H. Chen, K. P. Campbell, and C. T. Caskey. 1996. In vivo muscle gene transfer of full-length dystrophin with an adenoviral vector that lacks all viral genes. *Gene Ther* 3:965-72.
Crawford, G. E., J. A. Faulkner, R. H. Crosbie, K. P. Campbell, S. C. Froehner, and J. S. Chamberlain. 2000. Assembly of the dystrophin-associated protein complex does not require the dystrophin COOHterminal domain. *J Cell Biol* 150:1399-410.
Danko, I., J. D. Fritz, J. S. Latendresse, H. Herweijer, E. Schultz, and J. A. Wolff. 1993. Dystrophin expression improves myofiber survival in mdx muscle following intramuscular plasmid DNA injection. *Hum Mol Genet* 2:2055-61.
Davies, K. E., and K. J. Nowak. 2006. Molecular mechanisms of muscular dystrophies: old and new players. *Nat Rev Mol Cell Biol* 7:762-73.
Deconinck, N., and B. Dan. 2007. Pathophysiology of duchenne muscular dystrophy: current hypotheses. *Pediatr Neurol* 36:1-7.
DelloRusso, C., J. M. Scott, D. Hartigan-O'Connor, G. Salvatori, C. Barjot, A. S. Robinson, R. W. Crawford, S. V. Brooks, and J. S. Chamberlain. 2002. Functional correction of adult mdx mouse muscle using gutted adenoviral vectors expressing full-length dystrophin. *Proc Natl Acad Sci USA* 99:12979-84.
Duan, D., Z. Yan, Y. Yue, W. Ding, and J.F. Engelhardt. 2001a. Enhancement of muscle gene delivery with pseudotyped AAV-5 correlates with myoblast differentiation. *J Virol* 75:7662-7671.
Duan, D, Y. Yue, and J.F. Engelhardt. 2003. Consequences of DNA-dependent protein kinase catalytic subunit deficiency on recombinant adeno-associated virus genome circularization and heterodimerization in muscle tissue. *J Virol* 77:4751-4759.

(Continued)

*Primary Examiner* — Michael Burkhart
(74) *Attorney, Agent, or Firm* — Perkins Coie LLP

(57) ABSTRACT

Hybrid adeno-associated virus (AAV) vector systems able to efficiently express therapeutic target genes larger than may be carried in a single AAV vector are provided, wherein a highly recombinogenic foreign DNA sequence is incorporated into two or more ITR-mediated AAV vectors. In one aspect of one embodiment, the novel hybrid AAV vector system is a hybrid dual AAV (hdAAV) vector system. In another aspect of one embodiment, the novel hybrid AAV vector system is a hybrid tri AAV (htAAV) vector system. A method of treating a clinical disease caused at least in part by a defective gene is provided, and comprises (1) providing a hybrid AAV vector system capable of expressing a therapeutic target gene, wherein the therapeutic target gene is capable of replacing, restoring or counteracting the effects of the defective gene; and (2) administering a therapeutic amount of said vector system to a subject wherein said therapeutic target gene is expressed at levels having a therapeutic effect.

19 Claims, 18 Drawing Sheets

OTHER PUBLICATIONS

Duan, D, Z. Yan, and J.F. Engelhardt. 2006. Expanding the capacity of AAV vectors. In: Bloom, ME, Cotmore, SF, Linden, RM, Parrish, CR and Kerr, JR (eds). *Parvoviruses*. Hodder Arnold; Distributed in the USA by Oxford University Press: London, New York. pp. 525-532.

Duan, D., P. Sharma, J. Yang, Y. Yue, L. Dudus, Y. Zhang, K. J. Fisher, and J. F. Engelhardt. 1998. Circular Intermediates of Recombinant Adeno-Associated Virus have Defined Structural Characteristics Responsible for Long Term Episomal Persistence In Muscle. *J Vriol* 72:8568-8577.

Duan, D., Y. Yue, and J. F. Engelhardt. 2001b. Expanding AAV Packaging Capacity With Trans-splicing or Overlapping Vectors: A Quantitative Comparison. *Mol Ther* 4:383-91.

Duan, D., Y. Yue, Z. Yan, and J. F. Engelhardt. 2000. A new dual-vector approach to enhance recombinant adeno-associated virus-mediated gene expression through intermolecular cis activation. *Nat. Med* 6:595-8.

Dudley, R. W., Y. Lu, R. Gilbert, S. Matecki, J. Nalbantoglu, B. J. Petrof, and G. Karpati. 2004. Sustained improvement of muscle function one year after full-length dystrophin gene transfer into mdx mice by a gutted helper-dependent adenoviral vector. *Hum Gene Ther* 15:145-56.

Emery, A. E. 1991. Population frequencies of inherited neuromuscular diseases—a world survey. *Neuromuscul Disord* 1:19-29.

Ervasti, J. M. 2007. Dystrophin, its interactions with other proteins, and implications for muscular dystrophy. *Biochim Biophys Acta* 1772:108-17.

Ervasti, J. M., and K. P. Campbell. 1991. Membrane organization of the dystrophin-glycoprotein complex. *Cell* 66:1121-31.

Fechner, H., A. Haack, H. Wang, X. Wang, K. Eizema, M. Pauschinger, R. Schoemaker, R. Veghel, A. Houtsmuller, H. P. Schultheiss, J. Lamers, and W. Poller. 1999. Expression of coxsackie adenovirus receptor and alphav-integrin does not correlate with adenovector targeting in vivo indicating anatomical vector barriers. *Gene Ther* 6:1520-35.

Fischer, A.C., C.I. Smith, L. Cebotaru, X. Zhang, F.B. Askin, J. Wright, S.E. Guggino, R.J. Adams, T. Flotte, and W.B. Guggino. 2007. Expression of a truncated cystic fibrosis transmembrane conductance regulator with an AAV5-pseudotyped vector in primates. *Mol Ther* 15: 756-763.

Flotte, T.R., S.A. Afione, R. Solow, M.L. Drumm, D. Markakis, W.B. Guggino, P.L. Zeitlin and B.J. Carter. (1993). Expression of the cystic fibrosis transmembrane conductance regulator from a novel adeno-associated virus promoter. *J Biol Chem* 268: 3781-3790.

Flotte, T.R. 2007. Gene therapy: the first two decades and the current state-of-the-art. *J Cell Physiol* 213: 301-305.

Fu, H., J. Muenzer, R.J. Samulski, G. Breese, J. Sifford, X. Zeng, and D.M. McCarty. 2003. Self-complementary adeno-associated virus serotype 2 vector: global distribution and broad dispersion of AAV-mediated transgene expression in mouse brain. *Mol Ther* 8: 911-917.

Ghosh, A. 2007a. Rational design of split gene vectors to expand the packaging capacity of adenoassociated viral vectors. Ph.D. Thesis. University of Missouri, Columbia.

Ghosh, A., Y. Yue, and D. Duan. 2006. Viral serotype and the transgene sequence influence overlapping adeno-associated viral (AAV) vector-mediated gene transfer in skeletal muscle. *J Gene Med* 8:298-305.

Ghosh, A., Y. Yue, Y. Lai, and D. Duan. 2008. A hybrid vector system expands adeno-associated viral vector packaging capacity in a transgene independent manner. *Mol Ther* 16:124-130.

Ghosh, A., Y. Yue, C. Long, B. Bostick, and D. Duan. 2007b. Efficient Whole-body Transduction with Trans-splicing Adeno-associated Viral Vectors. *Mol Ther* 15:750-5.

Gilbert, R., R. W. Dudley, A. B. Liu, B. J. Petrof, J. Nalbantoglu, and G. Karpati. 2003. Prolonged dystrophin expression and functional correction of mdx mouse muscle following gene transfer with a helper-dependent (gutted) adenovirus-encoding murine dystrophin. *Hum Mol Genet* 12:1287-99.

Gilbert, R., A. Liu, B. Petrof, J. Nalbantoglu, and G. Karpati. 2002. Improved Performance of a Fully Gutted Adenovirus Vector Containing Two Full-Length Dystrophin cDNAs Regulated by a Strong Promoter. *Mol Ther* 6:501.

Gilbert, R., J. Nalbantoglu, J. M. Howell, L. Davies, S. Fletcher, A. Amalfitano, B. J. Petrof, A. Kamen, B. Massie, and G. Karpati. 2001. Dystrophin expression in muscle following gene transfer with a fully deleted ("gutted") adenovirus is markedly improved by trans-acting adenoviral gene products. *Hum Gene Ther* 12:1741-55.

Gilchrist, S. C., M. P. Ontell, S. Kochanek, and P. R. Clemens. 2002. Immune response to full-length dystrophin delivered to Dmd muscle by a high-capacity adenoviral vector. *Mol Ther* 6:359-68.

Grady, R. M., R. W. Grange, K. S. Lau, M. M. Maimone, M. C. Nichol, J. T. Stull, and J. R. Sanes. 1999. Role for alpha-dystrobrevin in the pathogenesis of dystrophin-dependent muscular dystrophies. *Nat Cell Biol* 1:215-20.

Grady, R. M., H. Zhou, J. M. Cunningham, M. D. Henry, K. P. Campbell, and J. R. Sanes. 2000. Maturation and maintenance of the neuromuscular synapse: genetic evidence for roles of the dystrophin—glycoprotein complex. *Neuron* 25:279-93.

Gregorevic, P., M. J. Blankinship, J. M. Allen, R. W. Crawford, L. Meuse, D. G. Miller, D. W. Russell, and J. S. Chamberlain. 2004. Systemic delivery of genes to striated muscles using adeno-associated viral vectors. *Nat Med* 10:828-34.

Halbert, C. L., J. M. Allen, and A. D. Miller. 2002. Efficient mouse airway transduction following recombination between AAV vectors carrying parts of a larger gene. *Nat Biotechnol* 20:697-701.

Harper, S. Q., M. A. Hauser, C. DelloRusso, D. Duan, R. W. Crawford, S. F. Phelps, H. A. Harper, A. S.Robinson, J. F. Engelhardt, S. V. Brooks, and J. S. Chamberlain. 2002. Modular flexibility of dystrophin: implications for gene therapy of Duchenne muscular dystrophy. *Nat Med* 8:253-61.

Hillier, B. J., K. S. Christopherson, K. E. Prehoda, D. S. Bredt, and W. A. Lim. 1999. Unexpected modes of PDZ domain scaffolding revealed by structure of nNOS-syntrophin complex. *Science* 284:812-5.

Hoffman, E. P. 1993. Genotype/phenotype correlations in Duchenne/Becker dystrophy. *Mol Cell Biol Hum Dis Ser* 3:12-36.

Hoffman, E. P., R. H. Brown, Jr., and L. M. Kunkel. 1987. Dystrophin: the protein product of the Duchenne muscular dystrophy locus. *Cell* 51:919-28.

Hoffman, E. P., K. H. Fischbeck, R. H. Brown, M. Johnson, R. Medori, J. D. Loike, J. B. Harris, R. Waterston, M. Brooke, L. Specht, and et al. 1988. Characterization of dystrophin in muscle-biopsy specimens from patients with Duchenne's or Becker's muscular dystrophy. *N. Engl J Med* 318:1363-8.

Hoffman, E. P., L. M. Kunkel, C. Angelini, A. Clarke, M. Johnson, and J. B. Harris. 1989. Improved diagnosis of Becker muscular dystrophy by dystrophin testing. *Neurology* 39:1011-7.

Huang, X., F. Poy, R. Zhang, A. Joachimiak, M. Sudol, and M. J. Eck. 2000. Structure of a WW domain containing fragment of dystrophin in complex with beta-dystroglycan. *Nat Struct Biol* 7:634-8.

Jiang, Z., G. Schiedner, S. C. Gilchrist, S. Kochanek, and P. R. Clemens. 2004. CTLA4Ig delivered by high-capacity adenoviral vector induces stable expression of dystrophin in mdx mouse muscle. *Gene Ther* 11:1453-61.

Jung, D., B. Yang, J. Meyer, J. S. Chamberlain, and K. P. Campbell. 1995. Identification and characterization of the dystrophin anchoring site on beta-dystroglycan. *J Biol Chem* 270:27305-10.

Kameya, S., Y. Miyagoe, I. Nonaka, T. Ikemoto, M. Endo, K. Hanaoka, Y. Nabeshima, and S. Takeda. 1999. alpha1-syntrophin gene disruption results in the absence of neuronal- type nitric-oxide synthase at the sarcolemma but does not induce muscle degeneration. *J Biol Chem* 274:2193-200.

Koenig, M., A. H. Beggs, M. Moyer, S. Scherpf, K. Heindrich, T. Bettecken, G. Meng, C. R. Muller, M. Lindlof, H. Kaariainen, and et al. 1989. The molecular basis for Duchenne versus Becker muscular dystrophy: correlation of severity with type of deletion. *Am J Hum Genet* 45:498-506.

Koenig, M., A. P. Monaco, and L. M. Kunkel. 1988. The complete sequence of dystrophin predicts a rod-shaped cytoskeletal protein. *Cell* 53:219-26.

Kunkel, L. M. 2005. 2004 William Allan Award address. Cloning of the DMD gene. *Am J Hum Genet* 76:205-14.

Kunkel, L. M., and E. P. Hoffman. 1989. Duchenne/Becker muscular dystrophy: a short overview of the gene, the protein, and current diagnostics. *Br Med Bull* 45:630-43.

Lai, Y., Y. Yue, M. Liu, and D. Duan. 2006. Synthetic intron improves transduction efficiency of transsplicing adeno-associated viral vectors. *Hum Gene Ther* 17:1036-42.

Lai, Y., Y. Yue, M. Liu, A. Ghosh, J. F. Engelhardt, J. S. Chamberlain, and D. Duan. 2005. Efficient in vivo gene expression by trans-splicing adeno-associated viral vectors. *Nat Biotechnol* 23:1435-9.

Li, D., Yue, Y., and Duan, D. 2008. Preservation of Muscle Force in Mdx3cv Mice Correlates with Low-Level Expression of a Near Full-Length Dystrophin Protein. *Am. J. Path* 172:1332-41.

Li, S., E. Kimura, R. Ng, B. M. Fall, L. Meuse, M. Reyes, J. A. Faulkner, and J. S. Chamberlain. 2006. A highly functional mini-dystrophin/GFP fusion gene for cell and gene therapy studies of Duchenne muscular dystrophy. *Hum Mol Genet* 15:1610-22.

Liu, M., Y. Yue, S. Q. Harper, R. W. Grange, J. S. Chamberlain, and D. Duan. 2005. Adeno-associated virus-mediated micro-dystrophin expression protects young Mdx muscle from contraction-induced injury. *Mol Ther* 11:245-56.

Matecki, S., R. W. Dudley, M. Divangahi, R. Gilbert, J. Nalbantoglu, G. Karpati, and B. J. Petrof. 2004. Therapeutic gene transfer to dystrophic diaphragm by an adenoviral vector deleted of all viral genes. *Am J Physiol Lung Cell Mol Physiol* 287:L569-76.

McCarty, D.M., H. Fu, P.E. Monahan, C.E. Toulson, P. Naik, and R.J. Samulski. 2003. Adeno-associated virus terminal repeat (TR) mutant generates self-complementary vectors to overcome the rate-limiting step to transduction in vivo. *Gene Ther* 10: 2112-2118.

Nakai, H., T.A. Storm, and M.A. Kay. 2000. Increasing the size of rAAV-mediated expression cassettes in vivo by intermolecular joining of two complementary vectors. *Nat Biotechnol* 18:527-532.

Nalbantoglu, J., G. Pari, G. Karpati, and P. C. Holland. 1999. Expression of the primary coxsackie and adenovirus receptor is downregulated during skeletal muscle maturation and limits the efficacy of adenovirus-mediated gene delivery to muscle cells. *Hum Gene Ther* 10:1009-19.

Ostedgaard, L.S., J. Zabner, D.W. Vermeer, T. Rokhlina, P.H. Karp, A.A. Stecenko, C. Randak, and M.J. Welsh. 2002. CFTR with a partially deleted R domain corrects the cystic fibrosis chloride transport defect in human airway epithelia in vitro and in mouse nasal mucosa in vivo. *Proc Natl Acad Sci USA* 99:3093-3098.

Ostedgaard, L.S., T. Rokhlina, P.H. Karp, P. Lashmit, S. Afione, M. Schmidt, J. Zabner, M.F. Stinski, J.A. Chiorini, and M.J. Welsh. 2005. A shortened adeno-associated virus expression cassette for CFTR gene transfer to cystic fibrosis airway epithelia. *Proc Natl Acad Sci USA* 102: 2952-2957.

Peters, M. F., M. E. Adams, and S. C. Froehner. 1997. Differential association of syntrophin pairs with the dystrophin complex. *J Cell Biol* 138:81-93.

Petrof, B. J. 1998. The molecular basis of activity-induced muscle injury in Duchenne muscular dystrophy. *Mol Cell Biochem* 179:111-23.

Petrof, B. J. 2002. Molecular pathophysiology of myofiber injury in deficiencies of the dystrophinglycoprotein complex. *Am J Phys Med Rehabil* 81:S162-74.

Phelps, S. F., M. A. Hauser, N. M. Cole, J. A. Rafael, R. T. Hinkle, J. A. Faulkner, and J. S. Chamberlain. 1995. Expression of full-length and truncated dystrophin mini-genes in transgenic mdx mice. *Hum Mol Genet* 4:1251-8.

Rando, T. A. 2001. The dystrophin-glycoprotein complex, cellular signaling, and the regulation of cell survival in the muscular dystrophies. *Muscle Nerve* 24:1575-1594.

Reich, S.J., A. Auricchio, M. Hildinger, E. Glover, A.M. Maguire, J.M. Wilson, and J. Bennett et al. (2003). Efficient trans-splicing in the retina expands the utility of adeno-associated virus as a vector for gene therapy. *Hum Gene Ther* 14:37-44.

Romero, N. B., S. Braun, O. Benveniste, F. Leturcq, J. Y. Hogrel, G. E. Morris, A. Barois, B. Eymard, C.Payan, V. Ortega, A. L. Boch, L. Lejean, C. Thioudellet, B. Mourot, C. Escot, A. Choquel, D. Recan, J. C. Kaplan, G. Dickson, D. Klatzmann, V. Molinier-Frenckel, J. G. Guillet, P. Squiban, S. Herson, and M. Fardeau. 2004. Phase I study of dystrophin plasmid-based gene therapy in Duchenne/Becker muscular dystrophy. *Hum Gene Ther* 15:1065-76.

Rothe, F., K. Langnaese, and G. Wolf. 2005. New aspects of the location of neuronal nitric oxide synthase in the skeletal muscle: a light and electron microscopic study. *Nitric Oxide* 13:21-35.

Sadoulet-Puccio, H. M., M. Rajala, and L. M. Kunkel. 1997. Dystrobrevin and dystrophin: an interaction through coiled-coil motifs. *Proc Natl Acad Sci USA* 94:12413-8.

Sander, M., B. Chavoshan, S. A. Harris, S. T. Iannaccone, J. T. Stull, G. D. Thomas, and R. G. Victor. 2000. Functional muscle ischemia in neuronal nitric oxide synthase-deficient skeletal muscle of children with Duchenne muscular dystrophy. *Proc Natl Acad Sci USA* 97:13818-23.

Sironi, M., U. Pozzoli, R. Cagliani, G. P. Comi, A. Bardoni, and N. Bresolin. 2001. Analysis of splicing parameters in the dystrophin gene: relevance for physiological and pathogenetic splicing mechanisms. *Hum Genet* 109:73-84.

Spessert, R., and M. Claassen. 1998. Histochemical differentiation between nitric oxide synthaserelated and -unrelated diaphorase activity in the rat olfactory bulb. *Histochem J* 30:41-50.

Sun, L., J. Li, and X. Xiao. 2000. Overcoming adeno-associated virus vector size limitation through viral DNA heterodimerization. *Nat Med* 6:599-602.

Thomas, G. D., M. Sander, K. S. Lau, P. L. Huang, J. T. Stull, and R. G. Victor. 1998. Impaired metabolic modulation of alpha-adrenergic vasoconstriction in dystrophin-deficient skeletal muscle. *Proc Natl Acad Sci USA* 95:15090-5.

Thomas, G. D., P. W. Shaul, I. S. Yuhanna, S. C. Froehner, and M. E. Adams. 2003. Vasomodulation by skeletal muscle-derived nitric oxide requires alpha-syntrophin-mediated sarcolemmal localization of neuronal Nitric oxide synthase. *Circ Res* 92:554 60.

Tidball, J. G., and M. Wehling-Henricks. 2007. The role of free radicals in muscular dystrophy. *J Appl Physiol* 102:1677-86.

Tochio, H., Q. Zhang, P. Mandal, M. Li, and M. Zhang. 1999. Solution structure of the extended neuronal nitric oxide synthase PDZ domain complexed with an associated peptide. *Nat Struct Biol* 6:417-21.

Uchida, Y., Y. Maeda, E. Kimura, S. Yamashita, Y. Nishida, T. Arima, T. Hirano, E. Uyama, S. Mita, and M. Uchino. 2005. Effective repetitive dystrophin gene transfer into skeletal muscle of adult mdx mice using a helper-dependent adenovirus vector expressing the coxsackievirus and adenovirus receptor (CAR) and dystrophin. *J Gene Med* 7:1010-22.

Wang, B., Li, J and X. Xiao. 2000. Adeno-associated virus vector carrying human minidystrophin genes effectively ameliorates muscular dystrophy in mdx mouse model. *Proc Natl Acad Sci USA* 97: 13714-13719.

Wang, Y. 2006. HSV-1 amplicon vectors are an efficient gene transfer system for skeletal muscle cells. *Curr Gene Ther* 6:371-81.

Wang, Z., T. Zhu, C. Qiao, L. Zhou, B. Wang, J. Zhang, C. Chen, J. Li, and X. Xiao. 2005. Adenoassociated virus serotype 8 efficiently delivers genes to muscle and heart. *Nat Biotechnol* 23:321-8.

Wang, Z., H.I Ma, J. Li, L. Sun, J. Zhang, and X. Xiao. 2003. Rapid and highly efficient transduction by double-stranded adeno-associated virus vectors in vitro and in vivo. *Gene Ther* 10: 2105-2111.

Wolff, J. A., and V. Budker. 2005. The mechanism of naked DNA uptake and expression. *Adv Genet* 54:3-20.

Xu, Z., Y. Yue, Y. Lai, C. Ye, J. Qiu, D.J. Pintel, and D. Duan. 2004. Trans-splicing adeno-associated viral vector-mediated gene therapy is limited by the accumulation of spliced mRNA but not by dual vector coinfection efficiency. *Hum Gene Ther* 15:896-905.

Yan, Z., D. C. Lei-Butters, Y. Zhang, R. Zak, and J. F. Engelhardt. 2007. Hybrid adeno-associated virus bearing nonhomologous inverted terminal repeats enhances dual-vector reconstruction of minigenes in vivo. *Hum Gene Ther* 18:81-7.

Yan, Z., R. Zak, Y. Zhang, and J. F. Engelhardt. 2005. Inverted terminal repeat sequences are important for intermolecular recombination and circularization of adeno-associated virus genomes. *J Virol* 79:364-79.

Yan, Z., Y. Zhang, D. Duan, and J. F. Engelhardt. 2000. From the Cover: Trans-splicing vectors expand the utility of adeno-associated virus for gene therapy. *Proc Natl Acad Sci USA* 97:6716-6721.

Yang, J., W. Zhou, Y. Zhang, T. Zidon, T. Ritchie, and J. F. Engelhardt. 1999. Concatamerization of Adeno-associated Viral Circular Genomes Occurs Through Intermolecular Recombination. *J Virol* 73:9468-77.

Yoshimura, M., Sakamoto, M., Ikemoto, M., Mochizuki, Y., Yuasa, K., Miyagoe-Suzuki, Y., and Takeda, S. 2004. AAV Vector-Mediated Microdystrophin Expression in a Relatively Small Percentage of mdx Myofibers Improved the mdx Phenotype. *Mol Ther* 10:821-28.

Yue, Y., and D. Duan. 2003a. Double strand interaction is the predominant pathway for intermolecular recombination of adeno-associated viral genomes. *Virology* 313:1-7.

Yue, Y., Z. Li, S. Q. Harper, R. L. Davisson, J. S. Chamberlain, and D. Duan. 2003b. Microdystrophin Gene Therapy of Cardiomyopathy Restores Dystrophin-Glycoprotein Complex and Improves Sarcolemma Integrity in the Mdx Mouse Heart. *Circulation* 108:1626-32.

Yue, Y., M. Liu, and D. Duan. 2006. C-terminal truncated microdystrophin recruits dystrobrevin and syntrophin to the dystrophin-associated glycoprotein complex and reduces muscular dystrophy in symptomatic utrophin/dystrophin double knock-out mice. Mol Ther 14:79-87.

Yue, Y., J. W. Skimming, M. Liu, T. Strawn, and D. Duan. 2004. Full-length dystrophin expression in half of the heart cells ameliorates beta-isoproterenol-induced cardiomyopathy in mdx mice. *Hum Mol Genet* 13:1669-75.

Yue, Y., and D. Duan. 2002. Development of multiple cloning site cis-vectors for recombinant adeno-associated virus production. *Biotechniques* 33: 672, 674, 676-678.

Zhang, L, C. Wang, H. Fischer, P.D. Fan, J.H. Widdicombe, Y.W. Kan, and J.Y. Dong. 1998. Efficient expression of CFTR function with adeno-associated virus vectors that carry shortened CFTR genes. *Proc Natl Acad Sci USA* 195: 10158-10163.

* cited by examiner

HYBRID-AAV VECTORS TO DELIVER LARGE GENE EXPRESSION CASSETTE

PRIORITY CLAIM

The present application claims benefit to United States Provisional Patent Application No. 61/130,087, filed May 28, 2008, the disclosure of which is incorporated herein by reference in its entirety.

GRANT STATEMENT

This invention was made at least in part from government support under Grant Nos. AR-49419, DK-76552, and NS-62934 awarded by the National Institutes of Health. The Government has certain rights in this invention.

BACKGROUND

Gene therapy is a technique used to correct defective genes that are responsible for the development of many diseases. The most common approach to gene therapy involves the insertion of a normal gene into a location within the genome to replace a nonfunctional gene. A vector is often used to deliver the therapeutic, normal gene to the subject's target cells. One vector used in gene therapy is adeno-associated virus (AAV), which is particularly attractive because it is not currently known to cause disease (thereby causing a very mild immune response), infects dividing and non-dividing cells, and may incorporate its genome into that of the host cell. However, AAV gene therapy has been challenged by its inherent 5 kilobase (kb) viral packaging limit. To deliver a large therapeutic gene using AAV gene therapy, investigators have attempted different strategies such as truncating the gene itself and/or the use of shorter transcriptional regulatory elements (Flotte, 1993; Ostedgaard et al., 2005). These approaches have met with some success for certain disease genes, but they did not completely solve the problem of delivering a large gene, such as the full-length dystrophin coding sequence, using AAV.

Mutations in the dystrophin gene result in Duchenne muscular dystrophy (DMD), Becker muscular dystrophy (BMD) and X-linked dilated cardiomyopathy (XLDC). Currently, there is no cure for these devastating diseases, but progress in gene therapy has brought hope of curing these relentless diseases. Dystrophin is a 427 kD rod-shaped cytosolic protein located under the sarcolemma (Hoffman et al., 1987; Koenig et al., 1988). It has four functional domains including the N-terminal, rod, cysteine-rich (CR) and C-terminal domains, as shown in FIG. 1. The rod domain can be further divided into 24 spectrin-like repeats and 4 proline-rich hinges. The N-terminal domain and a stretch of basically charged repeats in the rod domain connect dystrophin to γ-actin (Ervasti, 2007). The end of hinge 4 and the CR domain link dystrophin to the transmembrane protein dystroglycan (DG), which then binds to laminin in the extracellular matrix (Huang et al., 2000; Jung et al., 1995). The dystrophin-DG-laminin linkage is further stabilized by sarcoglycans (SGs) and sarcospan (SS). Essentially this structural link (between the cytoskeleton and the extracellular matrix) provides mechanical support to maintain sarcolemma integrity during muscle contraction. In dystrophin deficient muscle, the failure to absorb contraction-induced stress contributes to muscle pathology (Davies et al., 2006; Ervasti, 2007; Petrof, 1998; Petrof, 2002). The dystrophin C-terminal domain binds to two molecules of syntrophin (Syn) and one molecule of dystrobrevin (Dbr). Syntrophin and dystrobrevin also bind to each other (Peters et al., 1997; Sadoulet-Puccio et al., 1997). Both syntrophin and dystrobrevin have multiple isoforms. The predominant forms in muscle are α-syntrophin and α-dystrobrevin, respectively. Syntrophin is an important scaffolding molecule (Wang et al., 2000). Its PDZ-domain interacts with signaling molecule nNOS, as shown in FIG. 1 (Brenman et al., 1996; Hillier et al., 1999; Tochio et al., 1999). Together, dystrophin and its associated proteins (including DG, SG, sarcospan, syntrophin, dystrobrevin, and nNOS) form the dystrophin-associated glycoprotein complex (DGC) (Ervasti, 2007; Ervasti et al., 1991). The DGC provides mechanical support and signaling function for muscle.

In DMD patients, a complete loss of the dystrophin protein leads to severe muscle disease and premature death. DMD is the most prevalent lethal childhood genetic disease, affecting one in 3,500 newborn boys worldwide. In BMD patients, reduced expression or expression of a truncated dystrophin causes a relatively mild phenotype with later onset and relatively slow progression (Beggs et al., 1991; Bulman, 1991; Emery, 1991; Hoffman, 1993; Hoffman et al., 1988; Koenig et al., 1989). Selective loss of dystrophin in the heart leads to XLDC.

Gene therapy for DMD, BMD and XLDC attempts to replace the defective dystrophin gene with a functional dystrophin gene, so that all affected muscles in a patient's body may be treated. Currently, three gene therapy approaches have entered clinical trials with limited success. These therapies include antisense oligonucleotide (AON) mediated exon skipping, full-length dystrophin replacement with a plasmid vector, and adeno-associated virus (AAV) mediated microgene therapy.

AON-mediated exon-skipping aims at restoring the open reading frame by re-directing dystrophin RNA splicing. As defined by its mechanism, this approach only produces an internally truncated protein instead of the full-length protein. AON-mediated exon-skipping faces several challenges. First, it requires an accurate molecular diagnosis. The AON tailored to one type of mutation may not be applicable to other mutations. Second, the exon-skipping method cannot treat patients who carry mutations in the CR domain. Third, exon-skipping often requires repeated delivery of AON to the target tissue. It is currently not clear whether repeated AON administration is associated with untoward clinical effects.

Plasmid-mediated gene therapy has also met its challenges. The first clinical trial with the plasmid vector was reported in 2004 using direct muscle injection (Romero et al., 2004), but studies have demonstrated relatively low and variable dystrophin expression from the plasmid vector (Wolff et al., 2005). Currently the efficiency is below the therapeutic threshold (Romero et al., 2004). Additional hurdles to be resolved for the plasmid-mediated gene therapy include transient expression and poor cardiac transduction.

The AAV vector has several features that are extremely suitable for DMD, BMD and XLDC, which affects nearly all body muscles. First, AAV is an effective muscle gene delivery vector, as a single intravenous injection can result in widespread, systemic transduction in skeletal and heart muscles (Ghosh et al., 2007b; Gregorevic et al., 2004; Wang et al., 2005). Additionally, both skeletal and cardiac muscles are highly transduced by AAV vectors. The main drawback of the AAV vector is its 5 kb packaging capacity. The full-length dystrophin coding sequence is more than 11 kb, which is beyond the 5 kb packaging capacity of a single AAV vector.

Different approaches using dual-vector strategies have been attempted to expand AAV vector packaging capacity (Duan et al., 2006). Among these approaches are trans-splicing (ts) and overlapping (ov) AAV vector systems (Duan et al., 2000; Yan et al., 2000; Sun et al., 2000; Nakai et al., 2000; Duan et al., 2001 b). In tsAAV vectors, split segments of a target gene are engineered with splicing signals. Upon co-infection, the AAV genomes undergo head-to-tail recombination through the viral inverted terminal repeats (ITRs). The engineered splicing signals then remove the ITR junction and restore transgene expression. In the ovAAV vectors, the two split segments share a common sequence. Upon co-infection, these segments undergo homologous recombination to recover the full-length gene. The tsAAV and ovAAV strategies raised hope that AAV vector gene therapy could be expanded to diseases that are linked to large therapeutic gene. However, these approaches have failed solve the size problem, because inherent limitations related to the molecular properties of the target gene remain. Thus, the small packaging capacity is still considered a major limitation in AAV gene therapy (Flotte, 2007.).

Besides the plasmid vector therapy described above, other approaches to express the full-length dystrophin protein have been attempted without clinical success. For example, the vectors based on herpes simplex virus type 1 (HSV-1) amplicon and gutted adenovirus have been shown to have the capacity to express the full-length protein. However, HSV-1 amplicon approach has limited application for in vivo gene therapy because it cannot efficiently infect mature muscle (Wang, 2006). The gutted adenoviral vector approach also encounters problems. The gutted adenoviral vectors are the vectors deleted of all adenoviral sequences except for the terminal repeats and packaging signal. Compared with AAV vectors, the gutted adenoviral vectors are poorly expressed in skeletal muscle (Fechner et al., 1999; Nalbantoglu et al., 1999; Uchida et al., 2005), and some studies have also shown the vector genome loss over time (Dudley et al., 2004). Furthermore, the systemic whole body transduction has not been established with the gutted adenoviral vector.

SUMMARY

In one embodiment, a hybrid dual AAV (hdAAV) vector system comprises a first recombinant AAV vector comprising (i) a first DNA segment comprising a 5'-inverted terminal repeat (5'-ITR) of AAV, (ii) a second DNA segment comprising a first portion of an open reading frame of a target gene operably linked to a promoter, (iii) a third DNA segment comprising a splice donor site, (iv) a fourth DNA segment comprising an alkaline phosphatase (AP) gene fragment, and (v) a fifth DNA segment comprising a 3'-inverted terminal repeat (3'-ITR) of AAV; and a second recombinant AAV vector comprising (i) a first DNA segment comprising a 5'-ITR of AAV, (ii) a second DNA segment comprising the AP gene fragment, (iii) a third DNA segment comprising a splice acceptor site, (iv) a fourth DNA segment comprising a second portion of the open reading frame of the target gene, which together with the first portion of the open reading frame encodes the target gene (polypeptide), operably linked with a polyadenylation (pA) signal, and (v) a fifth DNA segment comprising a 3'-ITR of AAV.

In some aspects, the hdAAV vector system described above may be used with any target gene between 5kb and 10 kb. In a further aspect, the target gene may be a mini-dystrophin or micro-dystrophin gene.

In some aspects, the AP gene fragment may be the 0.87 kb, middle one-third of the full AP gene (SEQ ID NO:1). In other aspects, the AP gene fragment may be selected from any of the AP fragments dissected from the 0.87 kb fragment, such as the 0.44 kb front one-half ("AP-front") fragment (SEQ ID NO:2), the 0.43 kb back one-half ("AP-back") fragment, the 0.27 kb head ("AP-head") fragment (SEQ ID NO:4), the 0.34 body fragment ("AP-body") fragment (SEQ ID NO:5) and the 0.26 tail ("AP-tail") fragment (SEQ ID NO:6).

In another embodiment, a hybrid tri-AAV (htAAV) vector system comprises a first recombinant AAV vector comprising (i) a first DNA segment comprising a 5'-inverted terminal repeat (5'-ITR) of AAV, (ii) a second DNA segment comprising a head portion of an open reading frame of a target gene operably linked to a promoter, (iii) a third DNA segment comprising a first splicing donor site, (iv) a fourth DNA segment comprising an AP-head sequence, and (v) a fifth DNA segment comprising a 3'-inverted terminal repeat (3'-ITR) of AAV; a second recombinant AAV vector comprising (i) a first DNA segment comprising a 5'-ITR of AAV, (ii) a second DNA segment comprising the AP-head sequence, (iii) a third DNA segment comprising a first splicing acceptor site, (iv) a fourth DNA segment comprising a middle portion of the open reading frame of the target gene, (v) a fifth DNA segment comprising a second splicing donor site, (vi) a sixth DNA segment comprising a AP-tail sequence, and (vii) a seventh DNA segment comprising a 3'-ITR of AAV; and a third recombinant AAV vector comprising (i) a first DNA segment comprising a 5'-ITR of AAV, (ii) a second DNA segment comprising the AP-tail sequence, (iii) a third DNA segment comprising a second splicing acceptor site, (iv) a fourth DNA segment comprising a tail portion of the open reading frame of the target gene, which together with the head and middle portions encodes the target gene, operably linked with a pA signal, and (v) a fifth DNA segment comprising a 3'-ITR of AAV.

In some aspects, the 3'-ITR and 5'-ITR sets may be from different AAV serotypes. In one aspect, the htAAV vector system of claim 7, wherein the 5'-ITR of the first recombinant AAV vector and the 3'-ITR of the third recombinant AAV vector are from AAV serotype-5 and wherein the 3'-ITR of the first recombinant AAV vector, the 5'-ITR and 3'-ITR of the second recombinant AAV vector and the 5'-ITR of the third recombinant AAV vector are from AAV serotype-2.

In other aspects, the target gene expressed by the htAAV vector system is between 10 kb and 15 kb. The target gene may be a full-length dystrophin coding sequence. According to one embodiment of the htAAV vector system for expressing the full-length dystrophin, the head portion of the therapeutic target gene is SEQ ID NO:7, the middle portion of the therapeutic target gene is SEQ ID NO:8, and the tail portion of the therapeutic target gene is SEQ ID NO:9.

In further aspects, the AP-head gene fragment used in the htAAV vector system is SEQ ID NO:4, and in other aspects, the AP-tail gene fragment used in the htAAV vector system is SEQ ID NO:6

In yet another embodiment, a method of treating a clinical disease caused at least in part by a defective gene comprises (1) providing a hybrid AAV vector system capable of expressing a therapeutic target gene, wherein the therapeutic target gene is capable of replacing, restoring or counteracting the effects of the defective gene; and (2) administering a therapeutic amount of said vector system to a subject wherein said therapeutic target gene is expressed at levels having a therapeutic effect.

In one aspect, the clinical disease is caused by a single defective gene. In another aspect, the clinical disease is DMD, BMD, XLDC or any other form of muscular dystrophy, and the target gene is dystrophin. In still other aspects, the hybrid vector system is an hdAAV vector system and the target gene is a mini-or micro-dystrophin gene or the hybrid vector system is an htAAV vector system and the target gene is a full-length dystrophin coding sequence.

BRIEF DESCRIPTION OF THE DRAWINGS

FIG. 6A shows representative photomicrographs of LacZ staining from different experiment groups. FIG. 6B illustrates quantitative evaluation of β-galactosidase activity in AAV infected muscles. FIG. 6C is a bar graph that shows the relative transduction efficiency of the dual vectors comparing to that of the single intact LacZ vector.

DETAILED DESCRIPTION

Hybrid adeno-associated virus (AAV) vector systems able to efficiently express therapeutic target genes larger than may be carried in a single AAV vector are provided. The term "therapeutic target gene," "target gene" or "transgene" as used herein generally refer to a nucleotide sequence to be transferred using a vector and encodes a gene to a substance, such as a protein or peptide that has therapeutic potential with respect to a disease. When expressed, the therapeutic target gene may comprise a full-length protein or any number of domains, portions, segments or fragments thereof.

Figure 1:
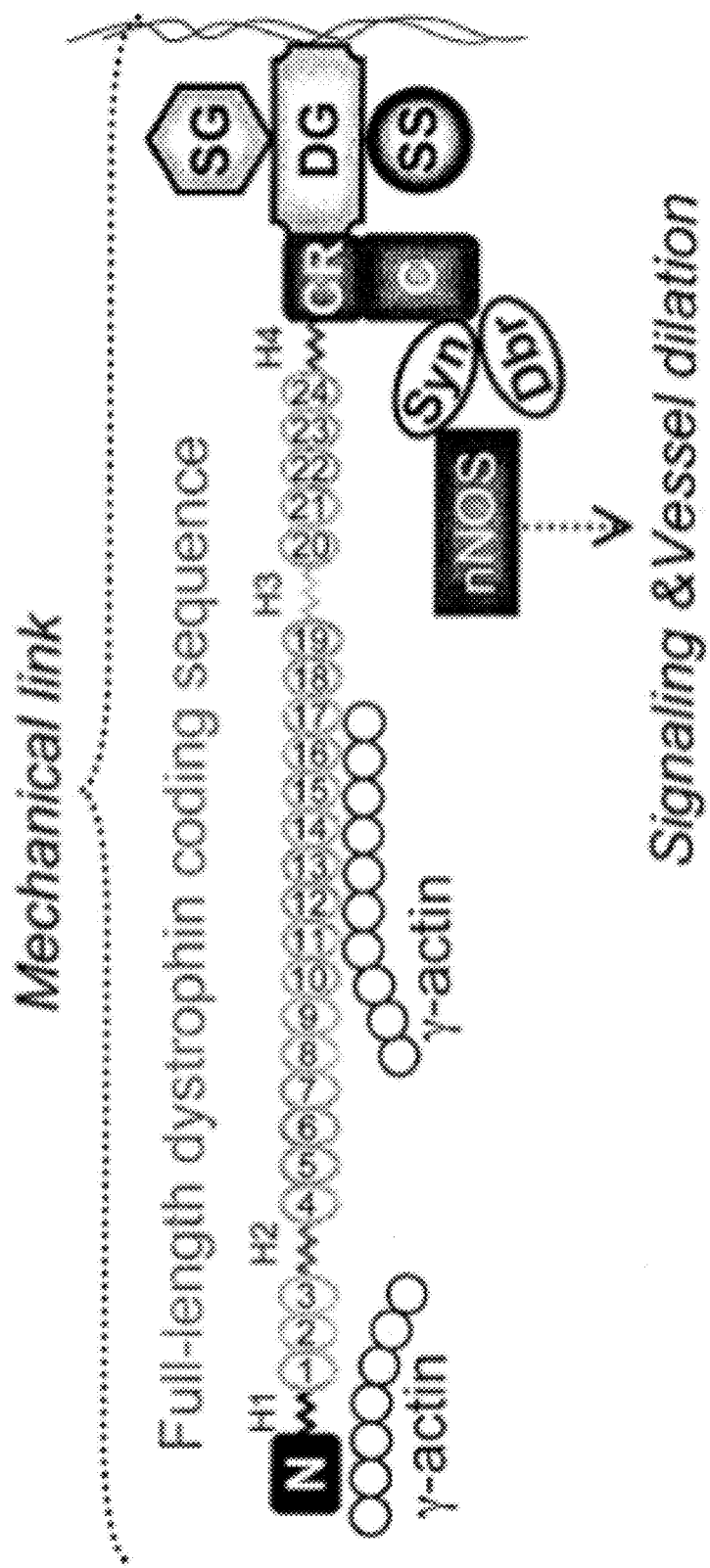
FIG. 1 is a schematic overview of the full length dystrophin coding sequence and associated proteins.
Figure 2:
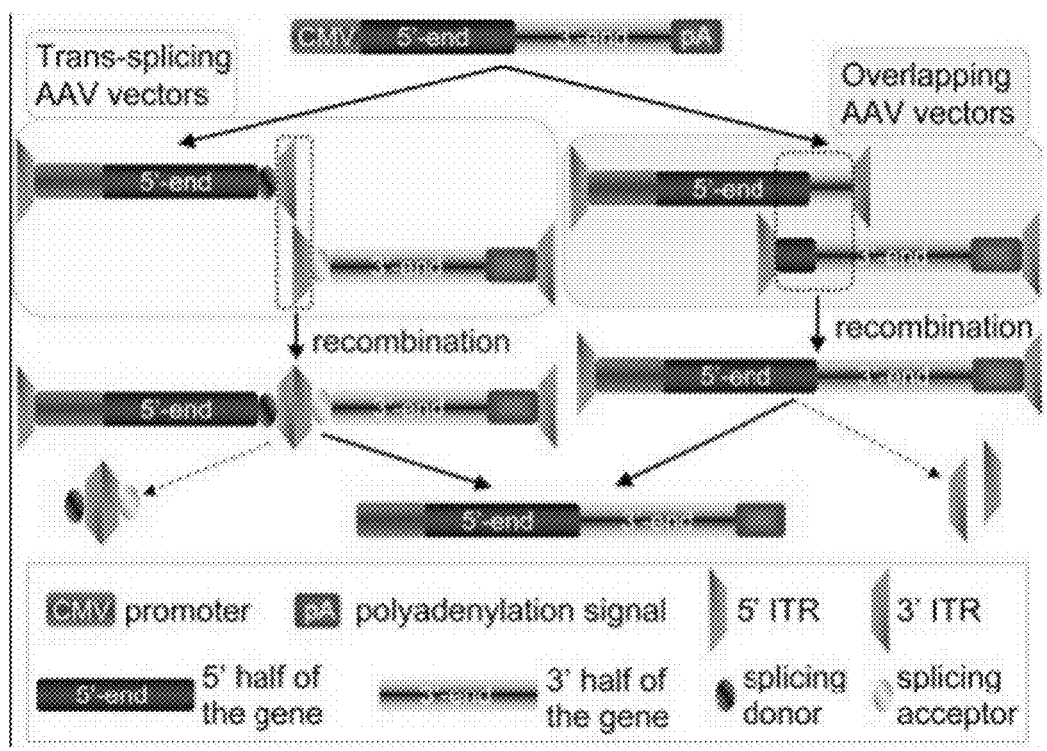
FIG. 2 is a schematic view of transgene reconstitution in trans-splicing (ts) and overlapping (ov) AAV vectors.

Traditional AAV vector systems include trans-splicing AAV (tsAAV) vectors and overlapping AAV (ovAAV) vectors. FIG. 2 outlines such tsAAV and ovAAV strategies.

In tsAAV, a large therapeutic target gene is split into a donor vector and an acceptor vector. The donor vector carries the 5' end of the gene and the splicing donor signal. The acceptor vector carries the splicing acceptor signal and the 3' end of the gene. Expression is achieved by AAV ITR-mediated intermolecular recombination and subsequent splicing of the recombined genome (Duan et al., 2001b; Sun et al., 2000; Yan et al., 2000). In ovAAV vectors, a large therapeutic gene is split into an upstream vector and a downstream vector. The upstream and the downstream vectors share a region of homology (Duan et al., 2001b; Halbert et al., 2002). Transgene reconstitution is achieved though homologous recombination between the overlapping regions in the upstream and the downstream vectors.

The traditional tsAAV and ovAAV systems are limited by the inherent properties of the therapeutic target gene. For the tsAAV vectors, an optimal site to split the therapeutic target gene must be identified. This requires labor-intensive screening and involves a likelihood that a particular therapeutic target gene may not carry an optimal site. The ovAAV strategy only works for a therapeutic target gene that contains a highly recombinogenic domain.

In one embodiment, a novel hybrid AAV vector system is described, wherein a highly recombinogenic foreign DNA sequence is incorporated into two or more ITR-mediated AAV vectors. In one aspect of one embodiment, the novel hybrid AAV vector system is a hybrid dual AAV (hdAAV)

vector system. In another aspect of one embodiment, the novel hybrid AAV vector system is a hybrid tri AAV (htAAV) vector system.

Figure 3:
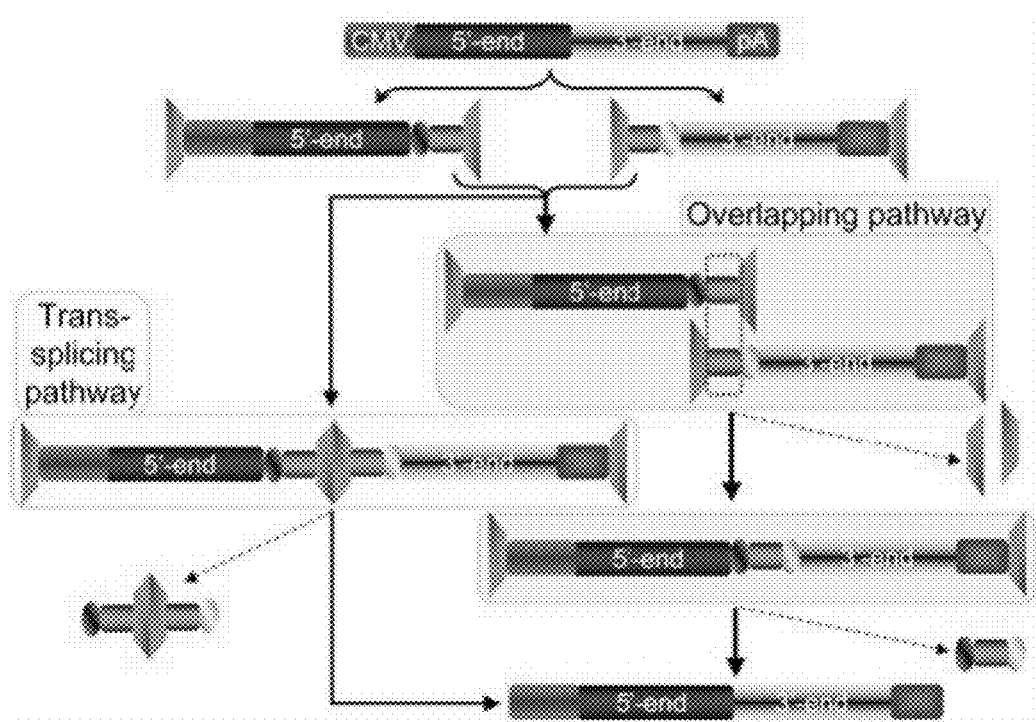
FIG. 3 is a schematic illustration of transgene reconstitution pathways in a hybrid dual (hd) AAV vector system.
Figure 5:
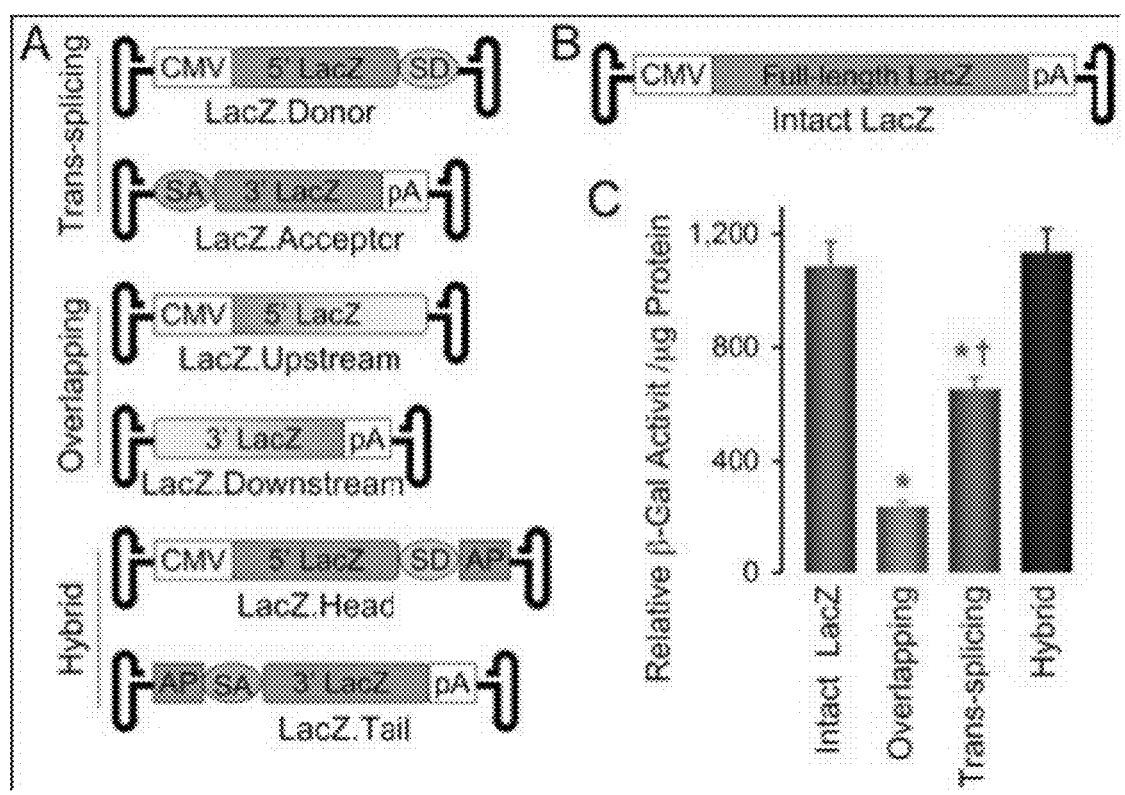
FIG. 5A illustrates LacZ trans-splicing (ts), overlapping (ov), and hybrid AAV dual vector systems.
FIG. 5B illustrates a single intact LacZ AAV vector.
FIG. 5C represents the relative transduction efficiency (β-galactosidase activity) in each of the vectors at 45 hours post-infection in MO59K cells.
Figure 6:
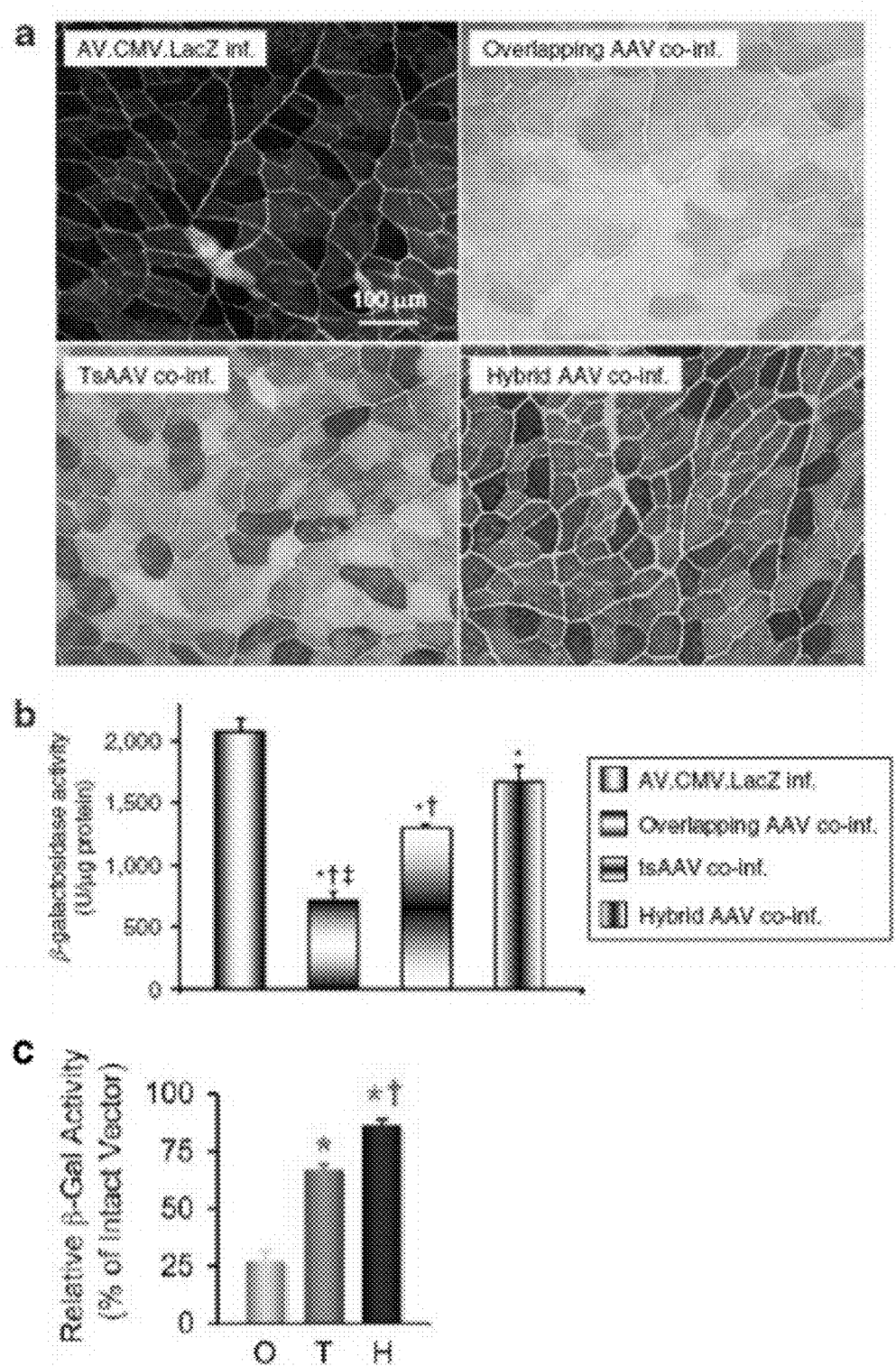
FIG. 6 illustrates an in vivo comparison of the LacZ dual AAV vectors depicted in FIG. 5A-B. The TA muscles of 6-week old BL10 mice were infected with an intact LacZ vector or co-infected with the dual AAV vectors. Transgene expression was determined at 6 weeks post infection by histochemical staining in muscle section and β-galactosidase activity assay in muscle lysate.
Figure 7A:
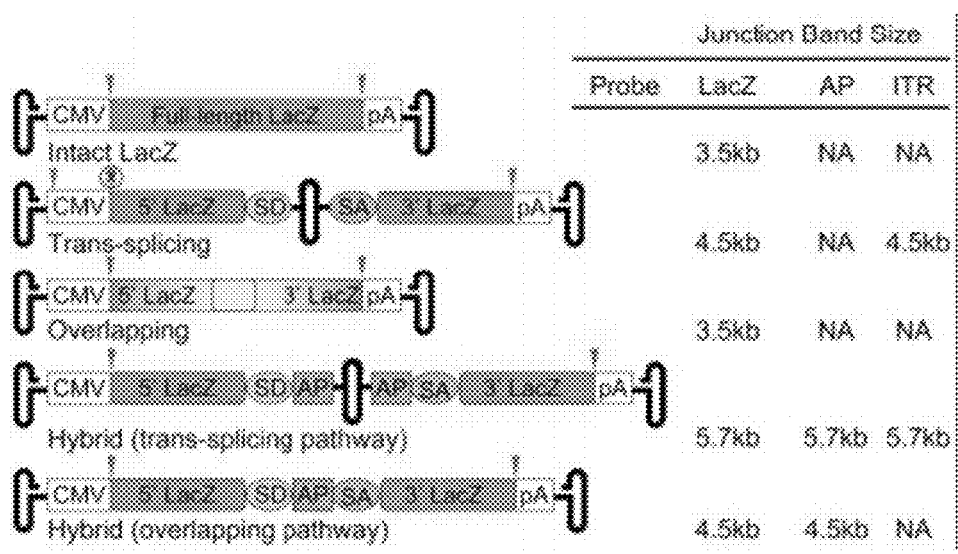
FIG. 7A illustrates the expected size of the diagnostic bands. NA=not applicable; Arrowheads=restriction enzyme sites. All restriction enzyme sites are NotI except for one SpeI site in the LacZ. Donor vector.

The novel hybrid AAV vector systems described herein allow for an expanded therapeutic target gene packaging in a therapeutic target gene-independent manner—which increases the efficiency of reconstituted gene transduction. This strategy allows therapeutic target gene reconstitution to occur by both ITR-dependent and ITR independent pathways as seen in FIGS. 5 to 7 and Example 4. Briefly, when a therapeutic target gene is split and inserted into the novel hybrid vector system, the therapeutic target gene reconstitution can be achieved through two pathways. It can occur via ITR-mediated recombination (FIG. 3, ts pathway) which is influenced by the gene splitting site. Alternatively, it can also occur through homologous recombination of the foreign DNA sequence (FIG. 3, overlapping pathway), which is not influenced by the therapeutic target gene.

Figure 7B:
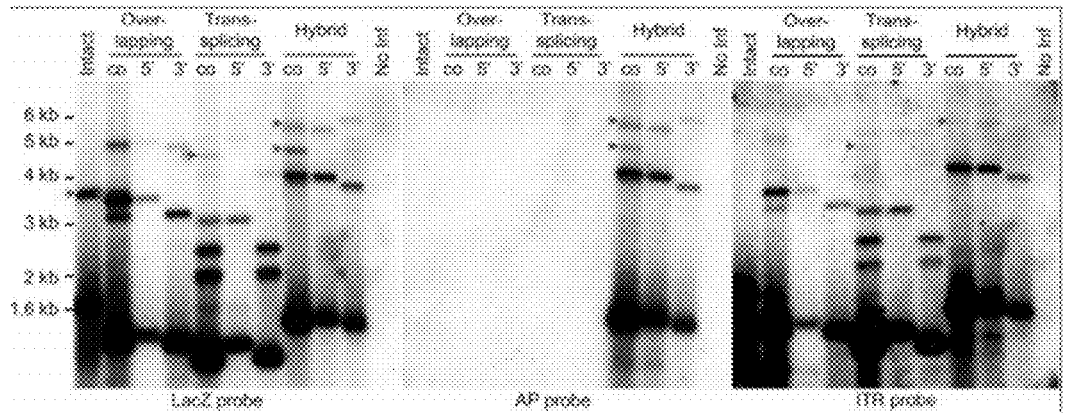
FIG. 7B depicts representative Southern blots. The same blot was sequentially probed with the LacZ, AP and ITR probes.

Participation of both the ts and overlapping pathways in transgene reconstitution was confirmed by Southern blot (FIG. 7B). Diagnostic bands for both the ITR-dependent (ts) pathway and the ITR-independent (overlapping) pathway were detected in hybrid vector infected cells (FIG. 7B). To further confirm the participation of both ts and overlapping pathways, a series of competition experiments were performed as described in Example 4 (see FIG. 9).

The efficiency of these systems in comparison to the other traditional AAV vector systems can be see in FIGS. 5 and 6 and is described in the examples below. The hybrid vectors outperformed tsAAV and ovAAV in both in vitro and in vivo experiments. In MO59Kcells, the hybrid vectors reached the same transduction efficiency as that of a single intact AAV vector (See FIG. 5 and Example 3 for hdAAV vectors and FIG. 12 and Example 6 for htAAV vectors), and in adult mouse muscle, the hybrid vectors reached 80% of that from a single intact AAV vector (See FIG. 6C and Example 3 for hdAAV vectors and FIG. 13 and Example 6 for htAAV vectors).

In one aspect, an hdAAV vector system comprises a first and a second AAV vector. The first AAV vector comprises a series of linked DNA sequences including, in order, a 5'-ITR of AAV, a first portion of a therapeutic target gene operably linked to a promoter, a splice donor site, a highly recombinogenic foreign DNA sequence, and a 3'-ITR of AAV. The second AAV vector comprises a series of linked DNA sequences including, in order, a 5'-ITR of AAV, the highly recombinogenic foreign DNA sequence, a splice acceptor site, a second portion of a therapeutic target gene operably linked to a pA signal, and a 3'-ITR of AAV. After reconstitution by an ITR-dependent or ITR-independent pathway in a host cell or cells, the first and second portions of the therapeutic target gene together encode a functional therapeutic target gene. An hdAAV vector system may be used in conjunction with a therapeutic target gene that is no more than 10 kb. Preferably, the therapeutic target gene associated with an hdAAV vector system is between 5 and 10 kb. When dissecting a large target gene into two sections to package into a set of hdAAV hybrid vectors, each portion of the therapeutic target gene (first and second portions) should fit into the AAV vector's packaging limit. The size of each therapeutic target gene portion will vary depending on the size of the promoter, ITR sets, splicing sets, and pA signal chosen.

In another aspect, an htAAV vector system comprises a first, second and third AAV vector. The first AAV vector comprises a series of linked DNA sequences including, in order, a 5'-ITR of AAV, a head portion of a therapeutic target gene operably linked to a promoter, a first splicing donor site, a first highly recombinogenic foreign DNA sequence, and a 3'-ITR of AAV. The second AAV vector comprises a series of linked DNA sequences including, in order, a 5'-ITR of AAV, the first highly recombinogenic foreign DNA sequence, a first splicing acceptor site, a middle portion of a therapeutic target gene, a second splicing donor site, a second highly recombinogenic foreign DNA sequence, and a 3'-ITR of AAV. The third AAV vector comprises a series of linked DNA sequences including, in order, a 5'-ITR of AAV, the second highly recombinogenic foreign DNA sequence, a second splice acceptor site, a tail portion of a therapeutic target gene operably linked to a pA signal, and a 3'-ITR of AAV. After reconstitution by an ITR-dependent or ITR-independent pathway in a host cell or cells, the head, middle and tail portions of the therapeutic target gene together encode a functional therapeutic target gene. An htAAV vector system may be used in conjunction with a therapeutic target gene that is no more than 15 kb. Preferably, the therapeutic target gene associated with an htAAV vector system is between 10 and 15 kb. When dissecting a large target gene into three sections to packaged into a set of htAAV hybrid vectors, each portion of the target gene (head, middle and tail portions) needs to fit into the AAV vector's packaging limit. The size of each therapeutic target gene portion will vary depending on the size of the promoter, ITR sets, splicing sets, and pA signal chosen.

Figure 4:
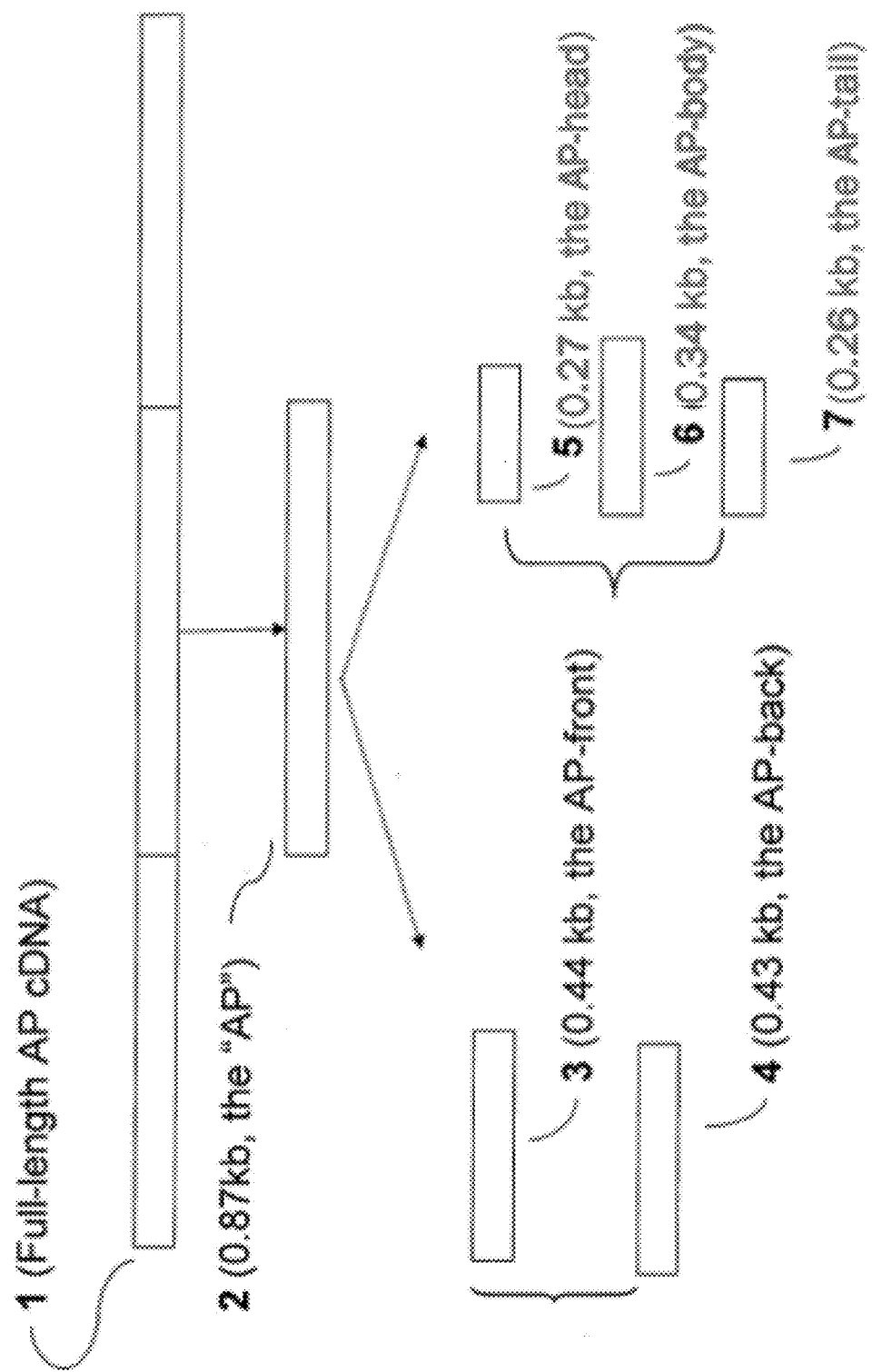
FIG. 4 illustrates the dissections of the alkaline phosphatase (AP gene) that may be used as highly recombinogenic DNA sequences in the hybrid vector systems described herein.

In one embodiment, the highly recombinogenic foreign DNA sequence comprises a portion of the alkaline phosphatase gene (AP). FIG. 4 illustrates dissections of the full AP sequence 1 and the AP portions that may be used in the hybrid AAV vector systems described herein. In one aspect, the highly recombinogenic foreign DNA sequence or sequences may include the middle one-third of the AP sequence, "AP" 2 (SEQ ID NO:1). The use of the middle one-third of the AP sequence in an hdAAV vector system is illustrated in the examples below. The AP 2 may be dissected into two sections: the AP-front, 3 (SEQ ID NO:2), and the AP-back 4 (SEQ ID NO:3). In another aspect, the AP 2 may be dissected into three fragments: the AP-Head 5 (SEQ ID NO:4), the AP-body 6 (SEQ ID NO:5), and the AP-tail 7 (SEQ ID NO:6). In another aspect, the highly recombinogenic foreign DNA sequence or sequences may be selected from AP-front, 3 (SEQ ID NO:2), AP-back 4 (SEQ ID NO:3), AP-Head 5 (SEQ ID NO:4), AP-body 6 (SEQ ID NO:5), and the AP-tail 7 (SEQ ID NO:6). In some preferred aspects, the highly recombinogenic foreign DNA sequence or sequences may be selected from the middle one-third of the AP sequence, "AP" 2 (SEQ ID NO:1), AP-Head 5 (SEQ ID NO:4), and AP-tail 7 (SEQ ID NO:6).

The AAV used in any of the embodiments described herein may refer to the naturally occurring wild-type virus or derivatives thereof. Thus, all AAV subtypes, serotypes and pseudotypes, both naturally occurring and recombinant forms are contemplated, except where required otherwise. As used herein, the term "serotype" refers to an AAV that is identified by and distinguished from other AAVs based on capsid protein amino acid sequences and/or the capsid protein reactivity with defined antisera. There are at least 11 serotypes of primate AAVs, AAV-1 to AAV-11. For example, serotype AAV-6 is used to refer to an AAV which contains capsid proteins encoded from the cap gene of AAV-6 and a genome containing 5' and 3'-ITR sequences from the same AAV-6 serotype. Pseudotyped AAV refers to an AAV that contains capsid proteins from one serotype and a viral genome including 5' and 3'-lTRs of a second serotype.

To improve unidirectional reconstitution in an htAAV vector system, two or more sets of splicing donor and splicing acceptors may be included. Additionally, two or more sets of ITRs from different AAV serotypes may be included. An ITR is an inverted terminal repeat sequence such as the sequence that is found at both ends of the viral genome of all known AAV serotypes. The inverted terminal repeats may be any set of ITR sequences. In one embodiment, two ITR serotypes are used, AAV-2 and AAV-5. The splicing signals may be any set of splicing donor and its corresponding acceptor, such as the splicing signals from the dystrophin gene, the splicing signals from adenovirus, or any synthetic splicing signals.

Gene therapy may be conducted to enhance the level of expression of a particular protein either within or secreted by a host cell or cells. The hdAAV and htAAV vector systems described above are suited for carrying large genes that may be used to genetically alter cells either for gene marking, replacement of a missing or defective gene, or insertion of a different therapeutic gene. Alternatively, a target therapeutic gene may be provided to the cell that decreases the level of expression. This may be used for the suppression of an undesirable phenotype, such as the product of a gene amplified or overexpressed during the course of a malignancy, or a gene introduced or overexpressed during the course of a microbial infection.

The therapeutic target gene may be any large gene (greater than 5 kb) that is associated with a clinical disease. In some embodiments, the clinical disease is caused by single-gene defects leading to missing, dysfunctional, under or over expressed proteins. Examples of diseases caused by single-gene defects include adenosine deaminase (ADA) deficiency, cystic fibrosis, hemophilia, muscular dystrophy (including DMD, BMD and XLDC), limb-girdle muscular dystrophy 2B, Miyoshi myopathy, anterior tibial distal myopathy, congenital muscular dystrophy, familial hypertrophic cardiomyopathy 1, dilated cardiomyopathy 1S, midventricular hypertrophic cardiomyopathy, myosin storage myopathy, Laing distal myopathy, Stargardt's disease, sickle cell anemia, phenylketonuria, Huntington's disease, myotonic dystrophy, familial hypercholesterolemia, neurofibromatosis, and polycystic kidney disease. Therapeutic target genes associated with single-gene defect diseases include adenosine deaminase (ADA), cystic fibrosis transmembrane conductance regulator (CFTR), Factor VIII clotting factor, dystrophin, dysferlin, alpha-2 laminin, myosin heavy chain 7, ATP-binding cassette transporter (ABCA4 for Stargardt's disease), hemoglobin, phenylalanine hydroxylase (PAH), huntingin (HTT), dystrophia myotonica protein kinase (DMPK), low-density lipoprotein receptor (LDLR), apolipoprotein B (APOB), neurofibromin (NF1), polycystic kidney disease 1 (PKD1) and polycystic kidney disease 2 (PKD2). In other embodiments, the clinical disease may be an acquired disease such as cancer, Parkinson's disease, viral infection (such as influenza, CMV or other herpesvirus, HIV, and hepatitis), heart disease, stroke, and diabetes. Some therapeutic target genes associated with these acquired diseases are, but not limited to, p53, glutamic acid decarboxylase (GAD), angiogenic proteins (for example, vascular endothelial growth factor (VEGF), fibroblast growth factor (FGF) and hepatocyte growth factor (HGF)), brain derived neurotrophic factor (BDNF), and insulin.

In one embodiment, the therapeutic target gene is dystrophin and the associated clinical disease is any form of dystrophin-deficient muscular dystrophy. The hybrid systems are advantageous for the expression of dystrophin because (1) there are no efficient recombinogenic domains in dystrophin to mediate the traditional ovAAV system and (2) dystrophin has very poor splicing sites for the traditional tsAAV system.

In DMD patents and animal models of DMD, membrane-associated nNOS is lost. nNOS is an important signaling molecule. The absence of sarcolemmal nNOS plays a significant role in DMD pathogenesis (Davies et al., 2006; Deconinck et al., 2007; Rando, 2001; Tidball et al., 2007). In particular, the lack of sarcolemmal nNOS has been shown to cause functional ischemia in contracting muscle in mouse models of DMD and in human DMD patients (Sander et al., 2000; Thomas et al., 1998; Thomas et al., 2003). It has been shown that the dystrophin C-terminal domain binds to syntrophin (Brenman et al., 1995). Syntrophin then recruits nNOS to the sarcolemma through its PDZ domain (Crawford et al., 2000; Yue et al., 2006). Furthermore, the presence of sarcolemmal syntrophin barely restores nNOS. Restoring nNOS is one goal for the treatment of DMD, BMD, XLDC and other muscular dystrophy therapies. Thus, it is important that the hybrid vector system is able to carry a dystrophin gene that is able to restore nNOS.

In some embodiments, the therapeutic target gene is a micro-dystrophin or a mini-dystrophin gene. A micro-dystrophin gene is a nucleic acid molecule or sequence that is 5 kb or less in length and encodes a modified or non-full-length dystrophin polypeptide that retains the N-terminal domain, the cysteine-rich domain, two or more repeats of the mid-rod domain, and two or more hinges of the mid-rod domain of a full-length dystrophin protein. A mini-dystrophin gene is a nucleic acid molecule or sequence that is more than 5 kb in length but less than the full-length dystrophin coding sequence and encodes a modified or non-full-length dystrophin polypeptide that retains the N-terminal domain, the cysteine-rich domain, two or more repeats of the mid-rod domain, and two or more hinges of the mid-rod domain of a full-length dystrophin protein molecule. Micro- or mini-dystrophin genes contemplated retain one or more biological functions of a full-length dystrophin protein. In one embodiment, the therapeutic target gene is a mini-dystrophin or micro-dystrophin gene able to restore nNOS. Examples of such mini/micro-dystrophin genes can be found in U.S. patent application Ser. No. 12/009,537 to Duan et al. and is incorporated herein by reference.

In other embodiments, the therapeutic target gene encodes a full-length dystrophin gene (the "full-length dystrophin coding sequence"). Clinical studies reveal the complexity between dystrophin gene mutation and disease phenotype (Beggs et al., 1991; Bulman et al., 1991; Hoffman et al., 1989; Koenig et al., 1989). These studies suggest that the 24 spectrin-like repeats in the rod domain are not functionally equivalent. In-frame deletion of certain regions in the rod domain is associated with more severe clinical disease. Very small in-frame deletions (such as deletion of exons 45 to 48) result in clinical symptoms even if they were expressed at the wild-type level (Beggs et al., 1991). These findings suggest that the strategies based on internally truncated mini and micro proteins may convert severe DMD to mild BMD but may not cure patients. Vectors that that can efficiently express the full-length protein remain the top choice for DMD and BMD gene therapy.

Figure 16:
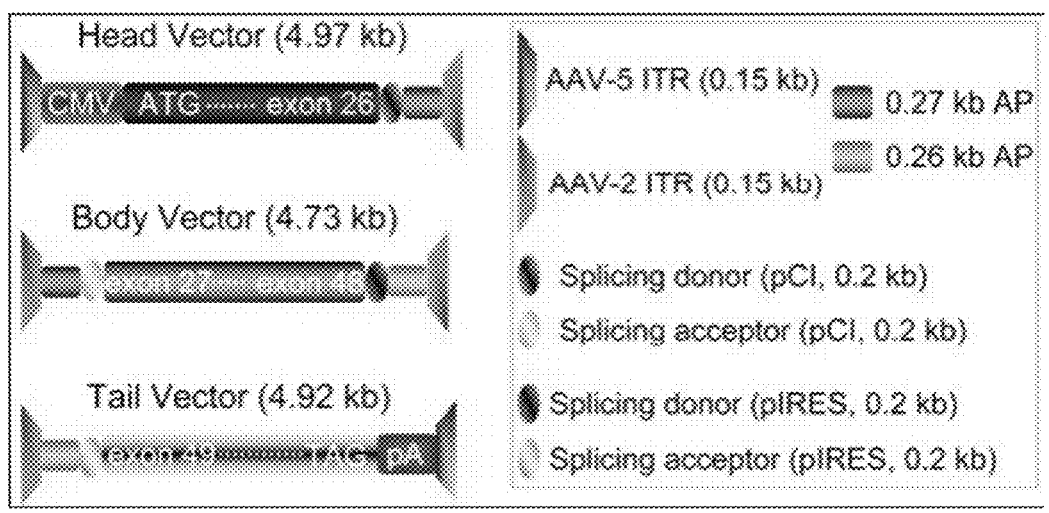
FIG. 16 is a schematic view of the htAAV vectors that contain, in three portions (head, middle, tail) the full-length dystrophin coding sequence.

When dissecting the full-length dystrophin coding sequence into three portions to be packaged into an htAAV vector system, each portion must fit into the AAV vector's packaging limit. Table 1 lists the size of each portion of the dystrophin gene that is able to fit within this limit. The maximum size of each portion is 3.64 bp, 3.77 bp and 4.03 bp for the head, middle and tail portions, respectively (Table 1). Table 2 lists a number of combinations that may be used to split the full-length dystrophin coding sequence, five of which (Table 2, #1 to #5) are able to fit into each AAV vector's packaging limit (see Example 7). In one embodiment, the full-length dystrophin coding sequence is dissected into three sections wherein the head portion spans from the ATG to exon 26 (SEQ ID NO:7), the middle portion spans from exon 27 to exon 48 (SEQ ID NO:8) and the tail portion spans from exon 49 to the TAG stop codon (SEQ ID NO:9). FIG. 16 illustrates three htAAV vectors carrying three dystrophin gene fragments and their resulting AAV vector size.

In another embodiment, a method for the treatments of DMD, BMD and/or XLDC in a subject by administering to the subject a therapeutically effective amount of the hybrid vector system containing a full length, mini or micro-dystrophin gene of the present invention.

The introduction of viral vectors by the methods of the embodiments described herein may involve use of any number of delivery techniques (both surgical and non-surgical) which are available and well known in the art. Such delivery techniques, for example, include vascular catheterization, cannulization, injection, inhalation, topical, oral, percutaneous, intra-arterial, intravenous, and/or intraperitoneal administrations. Vectors may also be introduced by way of biosprostheses, including, by way of illustration, vascular grafts, heart valves, intravascular stents, intravascular paving as well as other non-vascular prostheses.

In particular, for delivery of a vector of the embodiments described herein to a tissue such as muscle or lung, any physical or biological method that will introduce the vector to a host animal may be employed. Vector means both a bare recombinant vector and vector DNA packaged into viral coat proteins, as is well known for virus administration. Dissolving a virus vector in phosphate buffered saline is sufficient to provide a vehicle useful for muscle tissue expression, and there are no known restrictions on the carriers or other components that can be co-administered with the vector. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier or ease of administration and handling.

A therapeutically effective amount of the hdAAV or htAAV vector is administered, depending on the objectives of treatment. A therapeutically effective amount may be given in single or multiple doses. The minimal amount of dystrophin required for an effective DMD gene therapy has been determined. At the protein level, one fifth of the wild type level is sufficient to reduce muscle disease (Beggs et al., 1991; Bulman et al., 1991; Hoffman et al., 1989; Phelps et al., 1995). At the cell level, 15% mosaic expression ameliorates muscular dystrophy and 50% mosaic expression ameliorates cardiomyopathy (Hoffman et al., 1988; Kunkel et al., 1989; Liu et al., 2005; Yue et al., 2004). Based on these findings, $\geq$5% protein level expression in muscle lysate (by western) and $\geq$15% positive cells on muscle cross section (by immunostaining) are defined as therapeutic expression (Li et al., 2008; Yoshimura et al., 2004).

The effectiveness of the genetic alteration can be monitored by several criteria. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed. The treated subject may also be monitored for clinical features, and to determine whether the cells express the function intended to be conveyed by the therapeutic target gene. As described in Example 9, the function of mouse muscle injected with an htAAV vector system containing the full length dystrophin coding sequence may be measured by specific twitch force, specific tetanic force, and force drop over 10 cycles of eccentric contraction.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic regimen is ultimately the responsibility of the prescribing physician.

The following examples are provided to better illustrate the embodiments and are not to be interpreted as limiting the scope of any claimed embodiment. The extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLE 1

Materials And Methods

Proviral plasmids and recombinant AAV production. Seven different proviral cis plasmids were used for generating the LacZ AAV vectors. All the cis plasmids were flanked by AAV serotype-2 ITR. In the expression cassette, transcriptional regulation is controlled by the CMV promoter and the simian virus 40 polyadenylation signal (pA).

pcisCMV.LacZ was used for generating the single intact AAV vector (AV.CMV.LacZ). pcisCMV.LacZ.Upstream and pcisCMV.LacZ.Downstream were used for making the ovAAV vectors. pcisCMV.LacZ.Upstream was generated by replacing the Rous sarcoma virus (RSV) promoter in pcisRSV.LacZ.Upstream with the CMV promoter from pcisCMV.LacZ (Duan et al., 2001b) pcisCMV.LacZ. Downstream is identical to the previously described pcisRSV.LacZ.Downstream (Duan et al., 2001b).

A new set of cis plasmids to make the CMV promoter-based LacZ tsAAV vectors was generated. In the new LacZ tsAAV vectors, the LacZ gene was split at a putative splicing junction (AAG/G) that has been previously described (Xu et al., 2004). To generate pcisCMV.LacZ.Donor (also known as pDD535), a 1,687 bp DNA fragment was amplified using a previously reported pZX18 plasmid as the template (Xu et al., 2004). The polymerase chain reaction (PCR) primers were DL301 (forward primer) 5'-GCGC<u>GCTAGC</u>GGGATCGAAAGAGCCTGCTAAAGC (SEQ ID NO:10) (the underlined nucleotides represent the NheI site) and DL246 (reverse primer) 5'-GCGC<u>GGATCC</u>ATGCGGTACCTCAGAAACGC (SEQ ID NO:11) (the BamHI site is underlined). This PCR fragment contains the 5'-end of the LacZ gene and a splicing donor signal derived from the first intron of the human β-globulin gene. The NheI/BamHI double-digested fragment was then cloned between the CMV promoter and the 3'-ITR in pDD472, an intermediate cis plasmid carrying the CMV promoter. The final pcisCMV.LacZ.Donor plasmid contains the CMV promoter, 5'-end of the LacZ gene, and the splicing donor signal. In order to generate pcisCMV.LacZ.Acceptor (also called pDD536), 11,735 bp DNA fragment was amplified using pZX18 as the template and DL302 (5'-GAAGACTCTTGCGTTTCTG) (SEQ ID NO:12), as the forward primer, and DL303 (5'-GCGC TCTAGACGGGCAGACATGGCCTGCCCGG (SEQ ID NO:13), the XbaI site is underlined) as the reverse primer. The PCR product was digested with KpnI and IbaI and then cloned into pDD295, an intermediate cis plasmid carrying the simian virus 40 pA. The final pcisCMV.LacZ.Acceptor plasmid contains the splicing acceptor signal from the human immunoglobulin heavy chain gene, 3'-end of the LacZ gene, and the pA signal.

Figure 18:
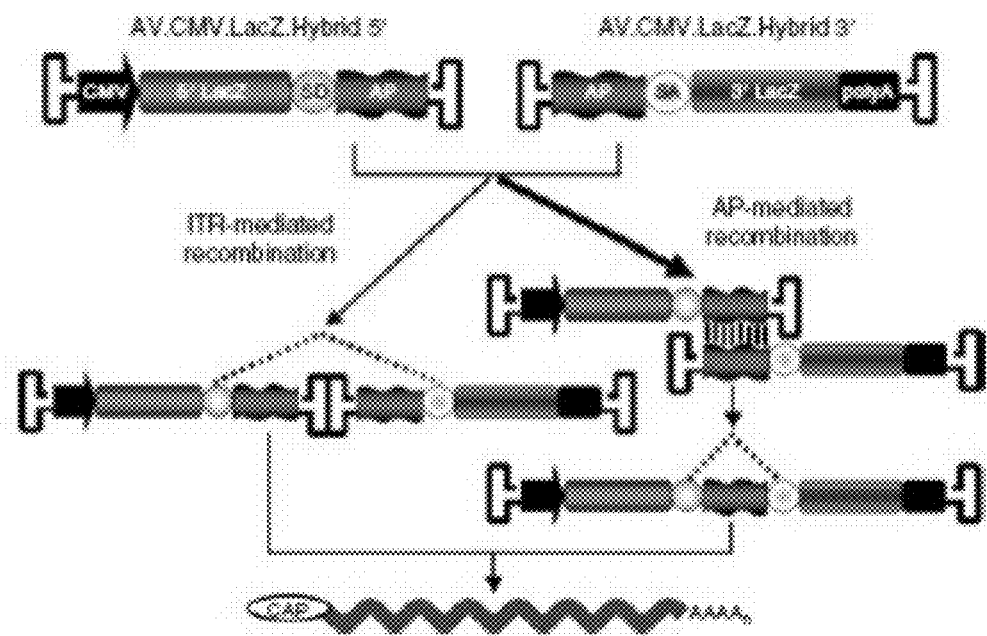
FIG. 18 is a schematic view of hybrid vector-mediated transgene reconstitution. The AV.CMV.LacZ.Hybrid5' vector contains the cytomegalovirus (CMV) promoter, the 5' half of the LacZ gene, the splicing donor (SD) and the 872 bp alkaline phosphatase (AP) sequence. The AV.CMV.LacZ.Hybrid3' vector contains the 872 bp AP sequence followed by the splicing acceptor (SA), the 3' half of the LacZ gene and the simian virus 40 polyadenylation signal (pA). Vector genomes are flanked by the adeno-associated virus-2 inverted terminal repeats (ITRs). Upon co-infection, the complete LacZ expression cassette can be reconstituted through AP sequence-mediated homologous recombination. Alternatively, it can be generated through viral ITR-mediated head-to-tail recombination. LacZ expression is achieved after the junction sequences are removed by cellular splicing machinery (dotted lines).

The LacZ dual hybrid AAV vectors were generated by engineering an 872 bp AP gene fragment into the CMV LacZ tsAAV vectors. The AP gene fragment comes from the middle one-third of the AP complementary DNA. Previous studies with the AP ovAAV vectors suggested that this 872 bp fragment is highly recombinogenic (Ghosh et al., 2006). First, an intermediate plasmid (pAG15) was generated. Briefly, the 872 bp AP gene fragment was amplified using the following set of primers: DL412 (forward primer) 5'-AGGTCT GCATGCGTGATCCTAGGTGG (SEQ ID NO:14) (underlined nucleotides represent the SphI site) and DL413 (reverse primer) 5'-ATATTAGCATGCACCACGGACCGCC (SEQ ID NO:15) (underline nucleotides represent the SphI site). There is a unique AvrII site and a unique RsrII site at the 5'- and the 3'-ends of the AP gene fragment, respectively. The PCR product was cloned into the SphI site in the middle of the synthetic intron in pZX18 to make pAG15 (Xu et al., 2005). To generate the pcisCMV,LacZ.Hybrid5' (also called pAG27), an AvrII (blunted)/NotI fragment from pAG15 was cloned between the BamHI (blunted) and NotI sites in pDD2, a previously reported cis plasmid (Yue et al., 2002). The resulting pcisCMV.LacZ.Hybrid5' plasmid contains the CMV promoter, the 5' half of the LacZ gene, the splicing donor signal, and the 872 bp AP sequence (FIG. 18). To generate pcisCMV.LacZ.Hybrid3' plasmid (also called pAG28), an RsrII (blunted)/NotI fragment form pAG15 was cloned between the SalI (blunted) and NotI sites in pAG1, an intermediate construct. The resulting pcisCMV.LacZ.Hybrid3' plasmid contains the same AP sequence, the splicing acceptor, the 3' half of the LacZ gene, and the simian virus 40 pA (FIG. 18).

To generate mini-dystrophin dual-vectors, an intermediate plasmid pAG21 was constructed in which the intron-containing AP sequence (from pAG15) was inserted into the exon 55/56 junction in the mini-dystrophin gene. Three PCRs were carried out to amplify (i) a 420 bp fragment on the 5'-end of the exon 55/56 junction (forward primer, DL382, 5'-GCCA GAGCCAAGCTTGAGTCATGG (SEQ ID NO:16); reverse primer, DL383, 5'-GATACTTACTTGCCATTGTTTCAT CAG (SEQ ID NO:17)); (ii) a 1 kb fragment on the 3'-end of the exon 55/56 junction (forward primer, DL384, 5'-TCTC CACAGGACCTCCAAGGTGAAATTG (SEQ ID NO:18); reverse primer, DL385, 5'-CCACCTGCAGAAGCTTC CATCTGG (SEQ ID NO:19)); and (iii) a 1 kb fragment containing intron splicing signals and the AP sequence (forward primer, DL386, 5'-CAATGGCAAGTAAGTATCAAG GTTACAAG (SEQ ID NO:20); reverse primer, DL387, 5'-TTGGAGGTCCTGTGGAGAGAAAGGCAAAG (SEQ ID NO:21)). The 5'-end of the third PCR fragment overlaps the 3'-end of the first PCR product. The 3'-end of the third PCR fragment overlaps the 5'-end of the second PCR product. The template for the first two PCRs is the ΔH2-R19 mini-dystrophin gene [a gift from Dr. Jeffrey Chamberlain (University of Washington, Seattle, Wash.)]. The template for the third PCR is pAG15. A final PCR was performed using DL382 and DL385 primers and all three PCR fragments as templates (1:1:1) to generate a 2.5 kb product. The 2.5 kb fragment was then used to swap out a corresponding 1.4 kb HindIII fragment from the mini-dystrophin gene to generate pAG21.

The pcisMinidys.Hybrid5' (also called pAG25) was constructed by inserting a 3,325 bp AvrII/NsiI fragment from pAG21 into a previously described pYL8 plasmid (Lai et al., 2005). The final product contains the CMV promoter, the 5' half of the mini-dystrophin gene (up to the end of exon 55), the splicing donor signal, and the 872 bp AP sequence. The pcisMinidys.Hybrid.3' (also called pAG26) was generated by cloning a 4 kb KpnI/HpaI fragment from pAG21 into pDD295. The final product contains the same AP sequence, the splicing acceptor, the 3' half of the mini-dystrophin gene, and the simian virus 40 pA.

The pcisAV.Donor.55 (also called pAG39, 55 stands for exon 55) was generated by inserting a 2,453 bp RsrII/NsiI fragment from pAG21 into a previously described pYL8 plasmid (Lai et al., 2005). The pAV.Acceptor.55 (also called pAG40) was generated by removing the AP sequence from pcisMinidys.Hybrid.3' with an AvrII/RsrII double digestion.

All viral stocks were made of serotype-6 recombinant AAV (AAV-6) and produced according to a published protocol (Ghosh et al., 2006; Lai et al., 2005; Lai et al., 2006).

In vitro studies. The transduction efficiency of the AAV vectors was examined in MO59K cells, a human glioblastoma cell line (American Type Culture Collection # CRL-2365; Manassas, Va.). Eighty percent confluent cells were infected in serum-free, antibiotic-free medium. Two hours after AAV inoculation, fetal bovine serum and penicillin and streptomycin were brought to the levels of concentration recommended by the American Type Culture Collection (Manassas, Va.). LacZ expression was analyzed at 45 hours after infection by cytological staining and the β-galactosidase assay (Applied Biosystems, Bedford, Mass.) as described earlier (Duan et al., 2001a).

Southern blot. Low molecular weight DNA was isolated from AAV-infected MO59K cells using a modified Hirt DNA isolation protocol. Briefly, at 45 hours after infection, cells were harvested from 6-well plates using a cell scraper in phosphate-buffered saline. After a 1 minute centrifugation at 800 g, the cell pellet was resuspended in 300 μl lysis buffer containing 1% sodium dodecyl sulfate, 50 mmol/l EDTA, and 100 mmol/l Tris pH 8.0. Cell lysate was then digested with proteinase K (1 μg/μl final concentration) and pronase (0.5 μg/μl final concentration) for 30 minutes. In order to precipitate low molecular weight DNA, 75 μl 5 mol/l NaCl was added to the cell lysate. After 2 hours incubation at 4° C., 250 μl Tris-EDTA (10 mmol/l Tris, pH 8.0, 1 mmol/l EDTA) and 100 μl Promega neutralizing solution (Wizard Plus SV minipreps, Promega, Madison, Wis.) were added to the tube. Cell lysate was mixed by inverting the tube several times. Cellular debris (including chromosome DNA) was then removed by 35 minutes of centrifugation at 15,700 g. Finally, low molecular weight DNA was purified using a DNA miniprep column (Wizard Plus SV minipreps, Promega, Madison, Wis.) and eluted in DNase-free water.

Southern blot was performed as previously described using radiolabeled LacZ, AP, and ITR probes, respectively (Duan et al., 2003). For the LacZ probe, a 780 bp MluI fragment from the LacZ gene was used. This probe spans both the 5' and 3' parts of the split LacZ gene. For the AP probe, a 359 bp SacI fragment from the middle of the AP gene was used. For the ITR probe, a 266 bp SphI fragment from a previously reported pZX19 plasmid was used (Xu et al., 2004). This fragment contains the double-D ITR sequence. To compare results from different probes, the membrane was first hybridized with the LacZ probe. After stripping, the same membrane was re-hybridized with the AP probe. The membrane was then stripped again and re-hybridized with the ITR probe. There was no leftover radioactivity in the membrane between different hybridizations.

Animal studies. Experiments in animals were performed in accordance with guidelines from the National Institutes of Health and institutional guidelines of the University of Missouri. Male BL10 and mdx mice were purchased from the Jackson Laboratory (Bar Harbor, Me.). Recombinant AAV was delivered to the tibialis anterior muscle in accordance with a previously described protocol (Duan et al., 1998) LacZ expression was analyzed by histochemical staining and β-galactosidase assay (Applied Biosystems, Bedford, Mass.) as described earlier (Ghosh et al., 2006; Duan, 2001a). Dystrophin expression was determined by immunofluorescence staining using a human dystrophin specific antibody (Dys-3, Novocastra, Newcastle, UK) in accordance with our published protocol (Yue et al., 2003b).

Other Materials. Full-length human dystrophin cDNA was obtained from Dr. Jeffrey Chamberlain (University of Washington, Seattle, Wash.). AAV-5 ITR was obtained from Dr. John Engelhardt (University of Iowa, Iowa City, Iowa). In all of the studies, synthetic intron splicing signals were used rather than the endogenous intron splicing signals, since it has been shown that synthetic splicing signal are as efficient as, or even more efficient than the endogenous splicing signals (Lai et al., 2006). Synthetic splicing signals were obtained from pCI (Promega, Madison, Wis.) and synthetic intron from pIRES (Clontech, Palo Alto, Calif.).

Statistical analysis. Data are presented as mean±SEM. Statistical analysis was performed using the SPSS software (SPSS, Chicago, Ill.). Statistical significance among multiple experimental groups was determined using one-way analysis of variance followed by Tukey post hoc analysis. Statistical significance between two experimental groups was determined by student t-test. The difference was considered to be significant when $P<0.05$.

EXAMPLE 2

Design and Construction of LacZ hdAAV Vectors

To accurately compare different vector systems, a series of AAV vectors to express a LacZ-expression cassette were generated. The AAV vectors packaged the same LacZ gene expression cassette into a single intact vector (AV.CMV.LacZ), the traditional dual tsAAV and ovAAV vectors, and dual hybrid AAV vectors.

FIG. 18 illustrates the design of the LacZ hdAAV vectors. The LacZ gene is divided into two parts and separately packed into two independent AAV virions called AV.CMV.LacZ.Hybrid5' and AV.CMV.LacZ.Hybrid3', respectively. Prior data on dual AAV vectors showed that transgene reconstitution is either dependent on the gene splitting site (for tsAAV vectors) or the transgene sequence (for the ovAAV vectors) (Ghosh et al., 2006; Lai et al., 2005; Lai et al., 2006). Thus, the success of these approaches hinges on the transgene itself. The key innovation in the hdAAV vectors is the inclusion of a highly recombinogenic foreign DNA sequence to allow for transgene-independent reconstitution. AV.CMV.LacZ.Hybrid5' contains the cytomegalovirus (CMV) promoter, the 5'-end of the LacZ gene, the splicing donor signal, and an 872 bp AP gene fragment. AV.CMV.LacZ.Hybrid3' contains the same 872 bp AP gene fragment, followed by the splicing acceptor signal, the 3'-end of the LacZ gene, and the pA signal. The 872 bp AP gene fragment represents the middle one-third of the human placental AP complementary DNA. This fragment is highly recombinogenic in the context of the ov vectors (Ghosh et al., 2006). To minimize the influence of the gene splitting site, the LacZ gene was split at exactly the same location in both the ts and hd vectors. The AP gene fragment facilitates homologous recombination between AV.CMV.LacZ.Hybrid5' and AV.CMV.LacZ.Hybrid3' in co-infected cells. The full-length LacZ expression cassette is regenerated through a transgene independent pathway. Because the hdAAV vectors also contain ITRs, transgene reconstitution can also undergo ITR-mediated recombination as in the traditional tsAAV vectors (FIG. 18).

EXAMPLE 3

In Vitro and In Vivo Transduction Efficiency of Dual-Hybrid AAV Vectors

LacZ Expression from the dual hybrid AAV vectors reached that of the single intact vector in MO59K cells. A series of AAV vectors were generated to express a LacZ-expression cassette as described in Examples 1 and 2. The AAV vectors packaged the same LacZ gene expression cassette into a single intact vector (AV.CMV.LacZ), the traditional dual tsAAV and ovAAV vectors, and dual hybrid AAV vectors. Because the LacZ-expression cassette is well known and characterized, this design eliminates the potential influence of the transcription regulatory elements in different systems. In all of the dual AAV vector sets, each individual vector carried only part of the LacZ gene. Individual infection with these vectors did not yield LacZ expression.

To evaluate the relative transduction efficiencies of the dual-vector strategies, MO59K cells were infected with the tsAAV, ovAAV and hybrid AAV vectors at a multiplicity of infection of 20,000 vector genome (vg) particles per cell (10,000 vg particles per cell for each vector). As a control, MO59K cells were infected with the single intact AV.CMV.LacZ at a multiplicity of infection of 10,000 vg particles per cell. This illustrates the maximal achievable infection level. LacZ staining was performed at 45 hours after-infection. Highly efficient transduction from AV.CMV.LacZ was observed from the hybrid AAV vectors, but not from the ovAAV or tsAAV vectors.

As shown in FIG. 5C, β-galactosidase activity in cell lysate was quantified to further demonstrate each dual vector's transduction efficiency. AV.CMV.LacZ infection yielded an activity of 1307±22 U/μg protein. The activity levels from the ovAAV and tsAAV vectors were significantly lower than that from the single intact AV.CMV.LacZ. Furthermore, the transduction efficiencies of the ovAAV vectors (389±20 U/μg protein) was lower than those of the tsAAV vectors (654±40 U/μg protein). Consistent with in situ LacZ staining results, the activity in dual hybrid AAV vector-infected cells reached 1137±82 U/μg protein. This level is significantly higher than those of the tsAAV and ovAAV vectors, and it was statistically comparable to that of the single intact AV.CMV.LacZ.

Transduction efficiency of the dual hybrid AAV vectors was significantly higher in mouse muscle. To determine whether the dual hybrid AAV vectors were could efficiently reconstitute LacZ expression in skeletal muscle, injections of single intact AV.CMV.LacZ ($1 \times 10^{10}$ vg particles) and different sets of the dual AAV vectors ($1 \times 10^{10}$ vg particles of each vector: tsAAV, ovAAV and hybrid AAV and a total of $2 \times 10^{10}$ vg particles per muscle) were made into the tibialis anterior muscles of 6-8 week old BL10 mice. LacZ expression was examined 6 weeks later (FIG. 6). In histochemical staining, widespread expression was observed in single intact AV.CMV.LacZ infected muscles and hybrid AAV vector co-infected muscles. The tsAAV and ovAAV vectors showed patchy expression with lower intensity (FIG. 6A). To quantify the relative efficiency among various vector sets, β-galactosidase activity was measured (FIG. 6B). As in the in vitro results in MO59K cells, the highest activity was achieved with the single intact AV.CMV.LacZ (2071±103 U/μg protein). The lowest activity was seen with the ovAAV vectors (711±69 U/μg protein). The tsAAV vectors resulted in an activity (1288±40 U/μg protein) higher than those of the ovAAV vectors, but significantly lower than that of the single intact vector. Among the three dual-vector systems, the dual hybrid AAV vectors yielded the highest β-galactosidase activity (1674±86 U/μg protein). This level reached 80.8% of that from the single intact vector, and was significantly higher than that from the other dual-vector systems (FIG. 6C).

EXAMPLE 4

Molecular Evidence for Target-Gene Independent Reconstitution of the Dual-Hybrid AAV Vectors The hdAAV vectors are designed such that gene reconstitution in the LacZ hybrid vector system occurs in a LacZ gene-independent manner. Specifically the engineered AP-sequence mediates homologous recombination between AV.CMV.LacZ.Hybrid5' and AV.CMV.LacZ.Hybrid3'. The complete expression cassette regenerates irrespective of the gene-splitting site and the recombinogenic potential of the LacZ gene sequence. The dual hybrid AAV vectors can also undergo ITR-mediated tsAAV pathway.

Figure 8:
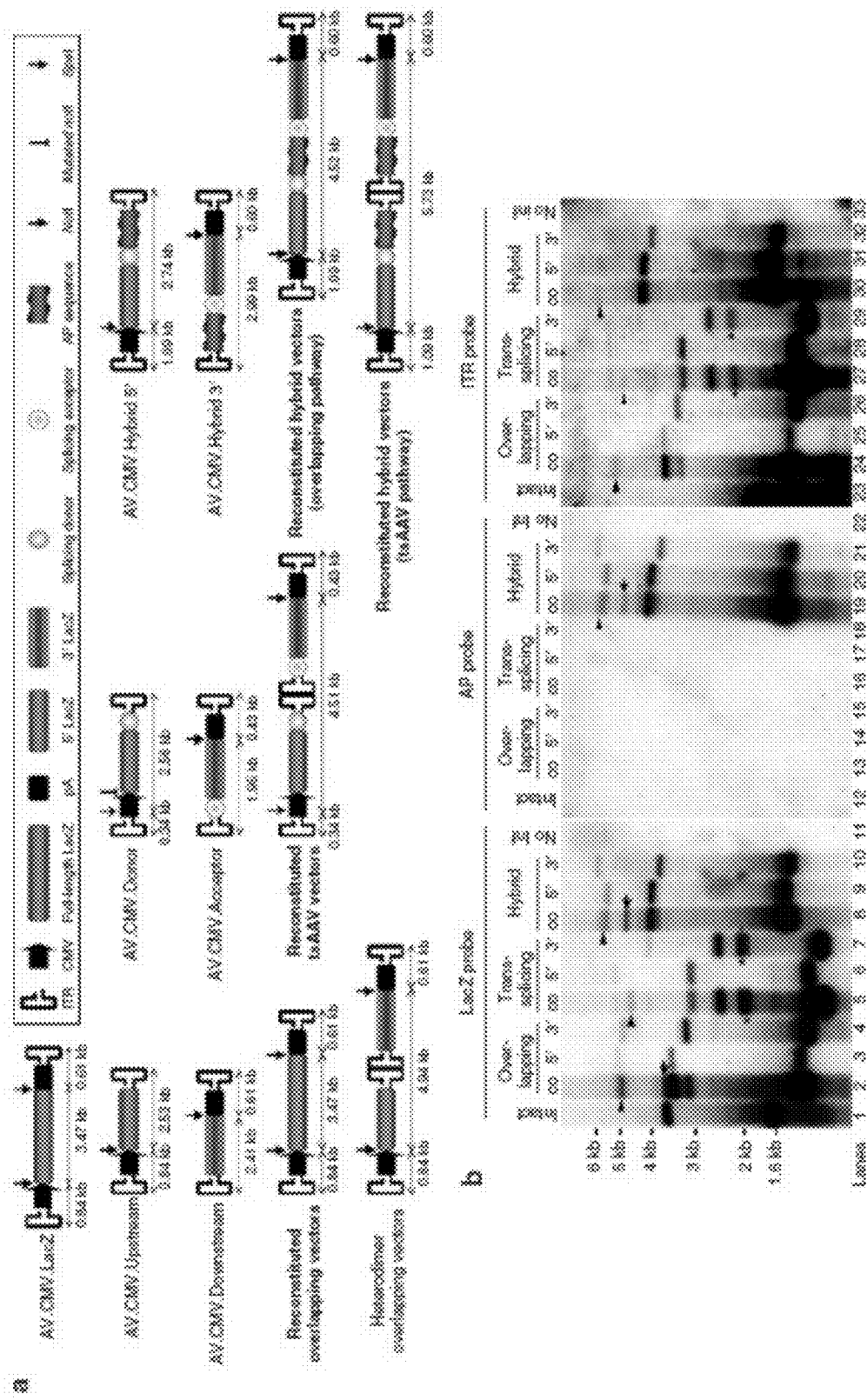
FIG. 8A is a schematic representation of the vector genome structure and the expected restriction pattern in individually infected or co-infected cells. For the purpose of presentation, all vector genomes are in linear form.
FIG. 8B depicts representative Southern blots of Hirt DNA from AAV-infected cells.

To demonstrate LacZ gene-independent reconstitution, the vector genome in AAV-infected cells was examined (FIG. 8). Low molecular weight Hirt DNA was digested with NotI (for AV.CMV.LacZ, ovAAV vector and hybrid AAV vector infection) or NotI/SpeI (for tsAAV vector infection). In AV.CMV.LacZ infected cells, NotI released a 3.47 kb band which was recognized only by the LacZ probe but not by the AP or ITR probes (FIG. 8b, lanes 1, 12, 23). Both AV.CMV.LacZ.Upstream and AV.CMV.LacZ.Downstream have only one NotI site. In cells individually infected with these vectors, diagnostic bands of 3.37 kb (for AV.CMV.LacZ.Upstream) and 3.02 kb (AV.CMV.LacZ.Downstream) were observed for head-to-tail monomers/concatamers by the LacZ and ITR probes, but not by the AP probe (FIG. 8b, lanes 3, 4, 14, 15, 25 and 26) Using the LacZ probe, a 5.06 kb tail-to-tail concatamer band for AV.CMV.LacZ.Upstream infection and a 4.82 kb head-to-head concatamer band for AV.CMV.LacZ.Downstream infection were observed. (FIG. 8b, lanes 3 and 4).

In ovAAV vector co-infected cells, the 3.47 kb diagnostic band representing the reconstituted genome was detected (FIG. 8b, lane 2). This band was not seen by the AP or ITR probes (FIG. 8b, lanes 13 and 24).

In AV.CMV.LacZ.Donor, the NotI site was inactivated during cloning, therefore SpeI/NotI double digestion was used. SpeI cuts AV.CMV.LacZ.Donor once but does not cut AV.CMV.LacZ.Acceptor. In cells individually infected with AV.CMV.LacZ.Donor or AV.CMV.LacZ.Acceptor, head-to-tail bands with the LacZ and ITR probes were observed (2.90 kb for AV.CMV.LacZ. Donor and 2.38 kb for AV.CMV.LacZ.Acceptor; FIG. 8b, lanes 6, 7, 28, and 29). The 5.12 kb tail-to-tail band (for AV.CMV.LacZ.Donor; FIG. 8b, lane 6) and the 3.9 kb head-to-head band (for AV.CMV.LacZ.Acceptor; FIG. 8b, lane 7) were also observed with the LacZ probe. Additionally, in AV.CMV.LacZ.Acceptor infected cells, a prominent ~2 kb band (FIG. 8b, lanes 7 and 29, asterisk) was detected. AV.CMV.LacZ.Acceptor has a vector genome size of 2.38 kb, a perfect size for self-complementary AAV packaging (Wang et al., 2003; McCarty et al., 2003; Fu et al., 2003). A self-annealed linear double-stranded vector genome, would be expected to produce a 1.95 kb band. Thus, the ~2 kb band may represent the self-annealed vector genome. All of the bands seen in individual vector infected cells were observed in AV.CMV.LacZ.Donor and AV.CMV.LacZ.Acceptor co-infected cells. The 4.51 kb diagnostic band representing the reconstituted vector genome was also observed (FIG. 8b, lanes 5 and 27).

Individual infection with each one of the hybrid vectors yielded band patterns similar to those seen with single infection of other dual-vectors. Head-to-tail monomer/concatamer bands (a 3.83 kb band for AV.CMV.LacZ.Hybrid5' infection and a 3.59 kb band for AV.CMV.LacZ.Hybrid5' infection; FIG. 8b, lanes 9, 10, 20, 21, 31, and 32) were detected with all three probes (LacZ, AP, and ITR, respectively). The 5.48 kb tail-to-tail concatamer band in AV.CMV.LacZ.Hybrid5' infected cells (FIG. 8b, lanes 9 and 20) and the 5.98 kb head-to-head concatamer band in AV.CMV.LacZ.Hybrid5' infected cells were also detected using the LacZ and AP probes (FIG. 8b, lanes 10 and 21). Vector genomes reconstituted through the AP sequence-mediated homologous recombination (the ov pathway) were observed for hd vector co-infection, as shown by a 4.52 kb band detected by the LacZ and AP probes but not by the ITR probe (FIG. 8b lanes 8, 19, and 30). Reconstitution of the LacZ expression cassette via ITR-mediated recombination (the ts pathway), was shown by a 5.73 kb band that was detected by all three probes.

Figure 9A:
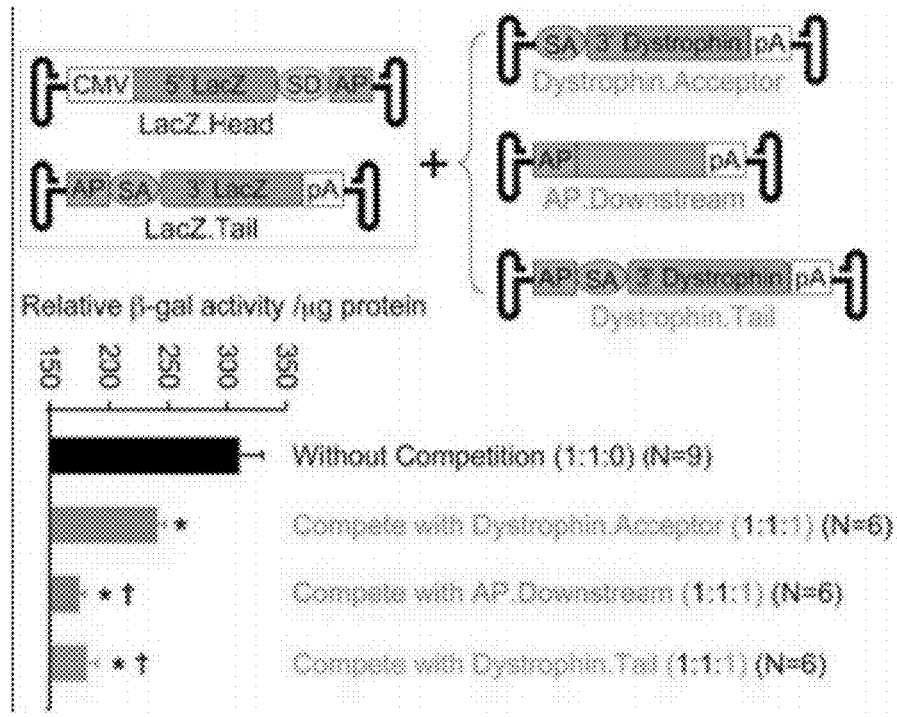
FIG. 9A illustrates a single-vector competition study.
Figure 9B:
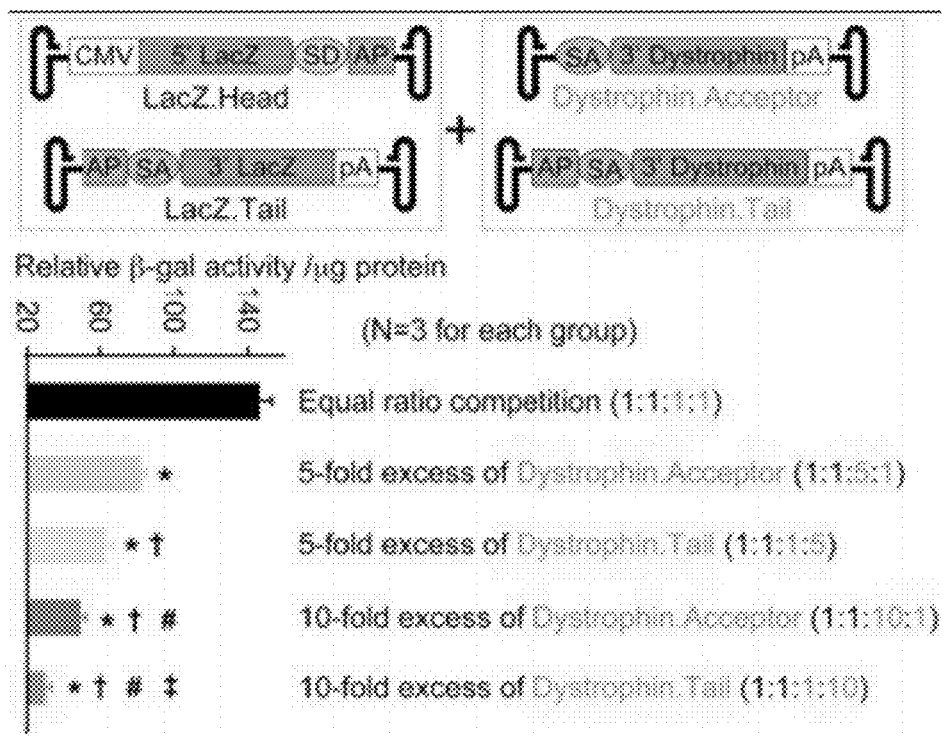
FIG. 9B illustrates a two-vector competition study.

A series of competition experiments were performed to provide further confirmation that both ts and overlapping pathways participate in target gene transduction using the hybrid vectors. First, as shown in FIG. 9A, cells were infected with LacZ.Head, LacZ.Tail and one of the competing vectors at the ratio of 1:1:1. Three competing vectors were examined including AP.Downstream, Dystrophin.Tail and Dystrophin.Aceptor. Both AP.Downstream and Dystrophin.Tail carry the AP sequence and these two vectors can directly compete with the LacZ hybrid vectors for AP sequence-mediated homologous recombination (overlapping pathway). Dystrophin.Acceptor does not contain the AP sequence and it does not directly compete with the overlapping pathway. Stronger inhibition with AP.Downstream and Dystrophin.Tail was observed. Next, as shown in FIG. 9B, a four-vector competition experiment was carried out, wherein LacZ.Head, LacZ.Tail, Dystrophin.Acceptor and Dystrophin.Tail were co-infected. The quantity of one of the competing vectors was subsequently raised. Increasing Dystrophin.Tail consistently led to a larger inhibition than increasing Dystrophin.Acceptor. The vectors with the AP sequence (such as AP.Downstream and Dystrophin.Tail) are stronger inhibitors, thus the overlapping pathway plays an important role in transgene reconstitution in the hybrid vector system. If a candidate therapeutic target gene does not have an optimal gene splitting site or is split at a poor site, the overlapping pathway provides an efficient alternate pathway for transgene reconstitution in the hybrid vectors provided herein.

EXAMPLE 5

Dual Hybrid AAV Vectors Efficiently Express a 6 kb Mini-Dystrophin Gene from a Poor Gene-Splitting Site The hdAAV vector system was tested to determine if it could improve transduction from a poor gene-splitting site in a therapeutic gene. The exon 55/56 junction divides the 6 kb mini-dystrophin gene into two 3 kb fragments. However, this junction is not ideal for splitting the mini-dystrophin gene (Lai et al., 2005). It has relatively low consensus splicing values (0.87 at the 5' end and 0.84 at the 3' end) and a relatively high U1 snRNA annealing free energy exchange value ($\Delta G$, −7.7 kcal/mol) (Lai et al., 2005; Sironi, 2001).

Figure 10:
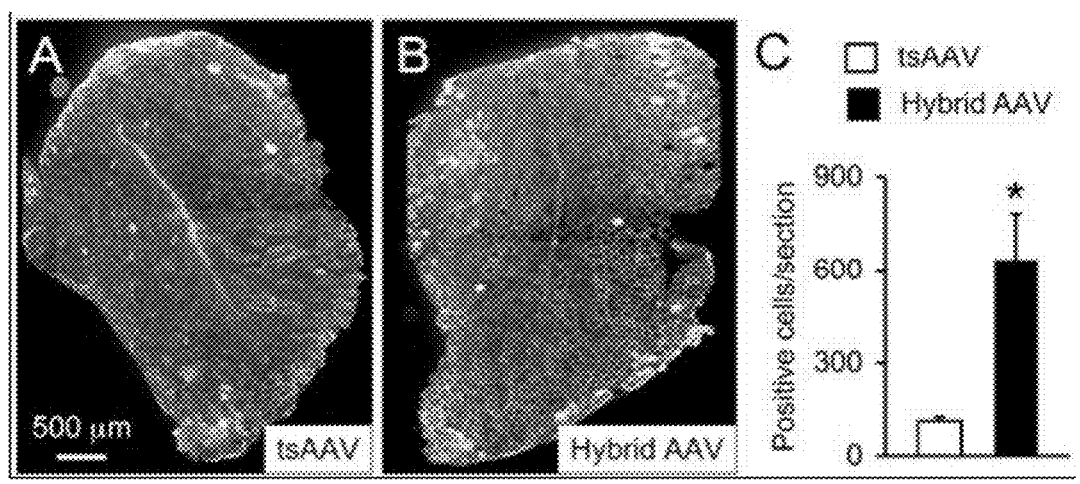
FIGS. 10A and 10B are representative dystrophin immunostaining photomicrographs from the trans-splicing (ts) and hybrid mini-dystrophin vectors, respectively.
FIG. 10C illustrates quantitative evaluation of mini-dystrophin expression.

The tsAAV and hdAAV vectors were generated by splitting the mini-dystrophin gene at the exon 55/56 junction. Each set of vectors was then independently injected into the tibialis anterior muscles of 2 month old dystrophin-deficient mdx mice ($1 \times 10^{10}$ vg particles of each vector and a total of $2 \times 10^{10}$ vg particles per muscle for each vector pair). Six weeks after injection, mini-dystrophin expression was quantified by immunofluorescence staining. The tsAAV vectors yielded 112.3±13.6 positive fibers/section and the dual hybrid AAV vectors yielded 635.3±146.4 positive fibers/section (FIG. 10). The transduction efficiency of the hybrid AAV vectors was significantly higher than that of the tsAAV vectors.

EXAMPLE 6

Trimming the AP Sequence to Meet the Need of the Hybrid Tri-AAV (htAAV) Vectors able to Express Full-Length Dystrophin A single AAV vector has the capacity of 5 kb. To construct an htAAV vector system for the full-length dystrophin gene, the dystrophin expression cassette is split into 5'-end, middle and 3'-end fragments. Therefore, four foreign overlapping and highly recombinogenic sequences are needed to reconstitute the dystrophin gene, one in the head, two in the body and another one in the tail. If the 0.87 kb AP sequence used in Example 1 is used as the foreign overlapping sequence, the size of the expression cassette, the four AP sequences, the splicing signals and the ITRs add up to a total genome size of 17.04 kb, which is beyond the 15 kb capacity of three single AAV vectors.

To solve this problem, the 0.87 kb AP sequence is further streamlined. First, the 0.87 kb AP sequence was divided into two parts in the middle (resulting in 0.44 kb and a 0.43 kb AP sequences). When inserted into the LacZ hybrid vectors as described in Examples 1 and 2, the transduction efficiency only reached half of that of the original LacZ hybrid vectors.

Figure 11:
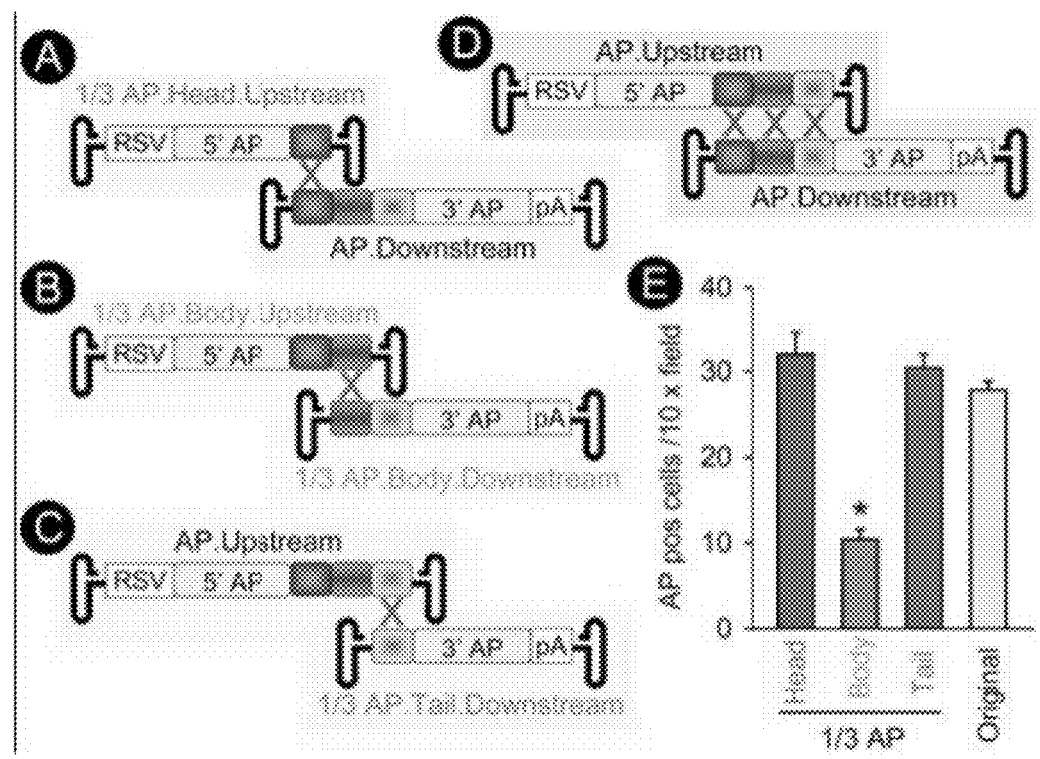
FIGS. 11A-D illustrate vectors with different AP sequence fragments.
FIG. 11E illustrates the respective transduction efficiency of each of the vectors.

Next, the 0.87 kb AP sequence was split into three pieces including a 0.27 kb fragment (1/3 AP.Head), a 0.34 kb fragment (1/3 AP.Body) and a 0.26 kb fragment (1/3 AP.Tail). The recombination efficiency of each of these fragments was compared in the context of the overlapping vectors (FIG. 11). Vectors based on the 0.27 kb (1/3 AP.Head) and the 0.26 kb (1/3 AP.Tail) fragments yielded efficiencies comparable to that of the original AP overlapping vectors. The vectors based on the middle 0.34 kb fragment (1/3 AP.Body) resulted in low reconstitution (FIG. 11e).

Figure 12:
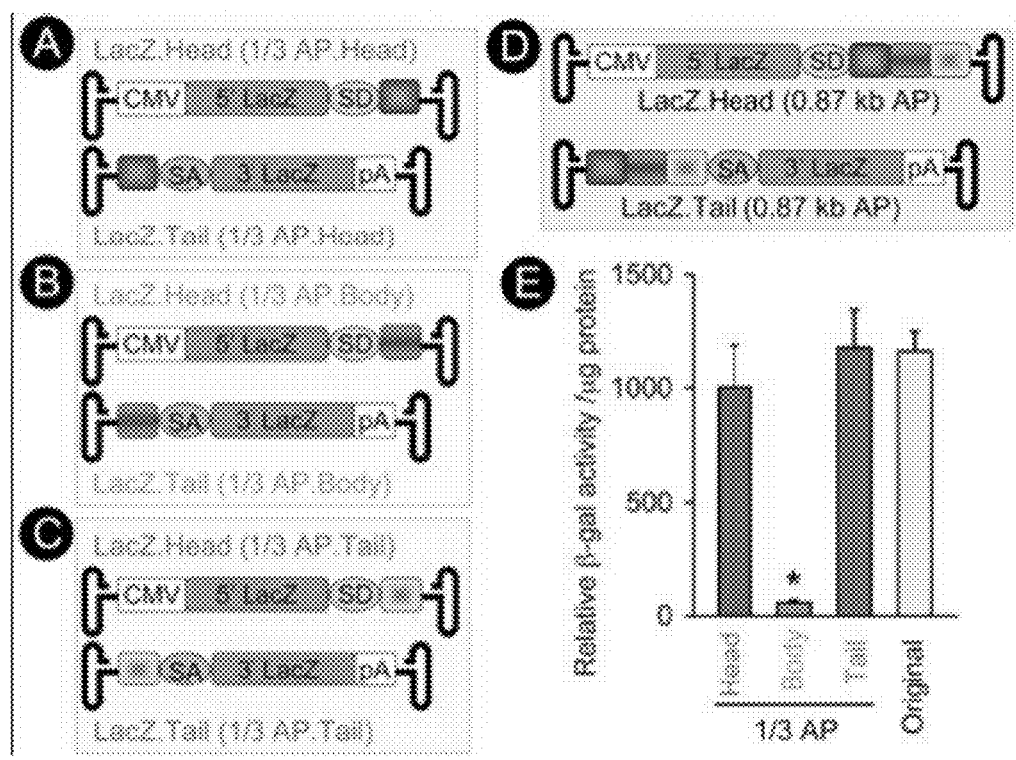
FIGS. 12A-D illustrate LacZ vectors with different AP sequence fragments.
FIG. 12E illustrates the respective transduction efficiency of each of the vectors.
Figure 13:
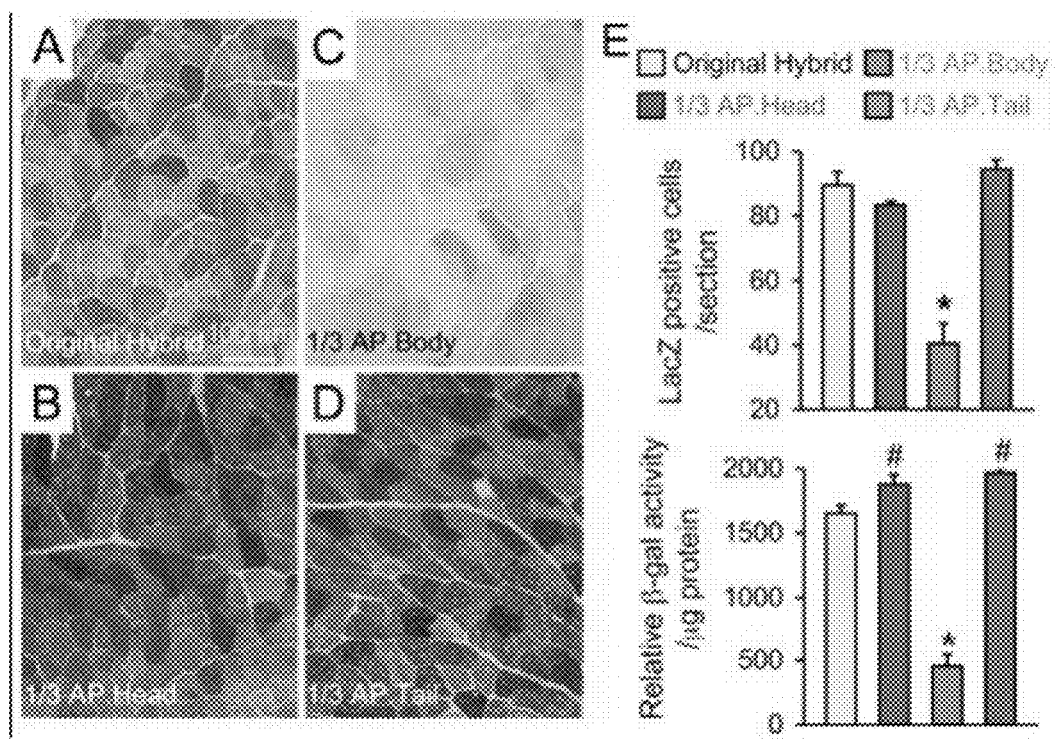
FIGS. 13A-D are representative cross-sectional images of mouse skeletal muscle at 40 days post-infection with the hybrid vectors depicted in FIG. 12.
FIG. 13E is the respective transduction efficiency in muscle section (number of positive cells) and muscle lysate (β-galactosidase activity).

Three sets of the LacZ hybrid AAV vectors were generated using these minimized AP sequences (0.27 kb, 0.34 kb and 0.26 kb, respectively (FIG. 12). Consistent with the findings with respect to the overlapping vectors (in FIG. 11), the hybrid vectors based on the 0.34 kb AP (1/3 AP.Body) yielded significantly much lower efficiency than other hybrid vectors in MO59K cells (FIG. 12E). This observation was further confirmed in mouse skeletal muscle (FIG. 13). On the other hand, the hybrid vectors based on the 0.27 kb and the 0.26 kb AP sequences (1/3 AP.Head and 1/3 AP.Tail., respectively) performed extremely well. The result showed stronger LacZ staining in muscle sections and significantly higher β-galactosidase activities than the LacZ hdAAV vectors discussed in Examples 1 to 4. Additional sequence analysis suggests that the 0.27 kb (1/3 AP.Head) and the 0.26 kb (1/3 AP.Tail) are two different sequences with different GC contents and do not share any sequence homology.

The identification of two distinctive and highly recombinogenic AP sequences allows for the generation of the htAAV vectors. The size of these fragments perfectly fits the 15 kb maximal packaging capacity of the htAAV system, as the total genome size is: 11.86 kb (expression cassette)+1.7 kb (ITRs and splicing signals)+1.06 kb (four overlapping AP sequences)=14.62 kb.

EXAMPLE 7

Design and Construction of htAAV Vectors

Figure 14A:
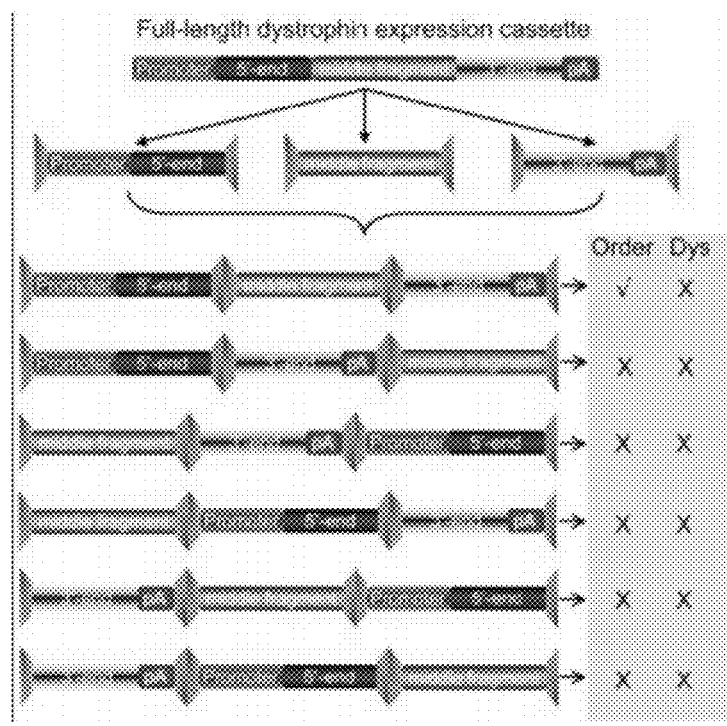
FIG. 14A Illustrates the concept that for hdAAV recombination, random recombination will unlikely put three AAV genomes in the right order.
Figure 14B:
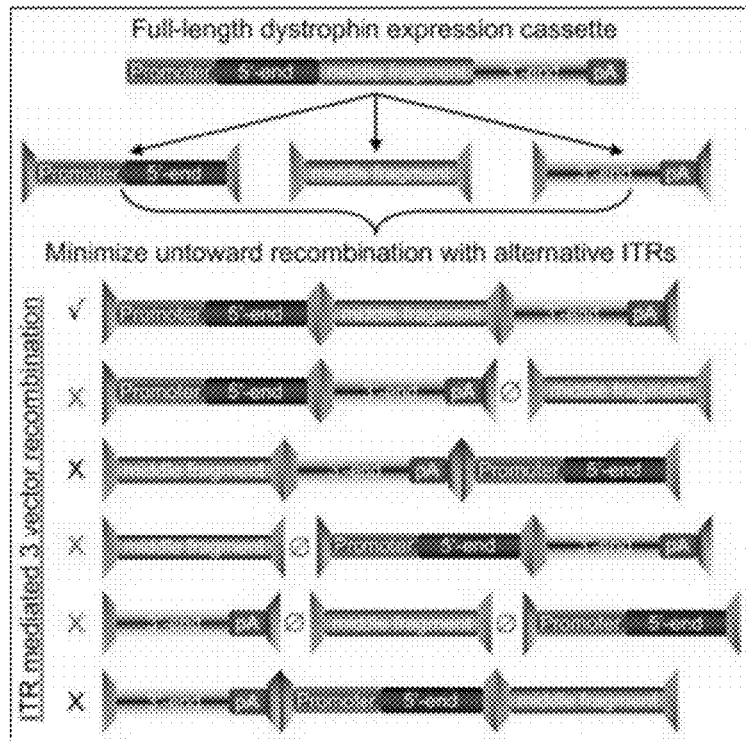
FIG. 14B illustrates the concept that using ITRs from different AAV serotypes minimizes random recombination.

Construction and Design of Tri-Hybrid AAV Vector System able to Express Full-Length Dystrophin Gene A full-length dystrophin expression cassette is 11.86 kb, as described in Example 5. The expression cassette includes the full-length dystrophin coding sequence (11.06 kb), a promoter (0.6 kb) and a polyadenylation (pA) signal (0.2 kb). For generation of the htAAV vector system, the expression cassette is split into three parts (head, body and tail) and then cloned into three AAV vectors (head vector, body vector and tail vector) The head vector contains the promoter and the 5'-end of the dystrophin gene, the body vector contains the middle portion of the dystrophin gene, and the tail vector contains the 3' end of the dystrophin gene and the pA signal. The chance of these three vectors to unidirectionally recombine in the correct order is slim, as shown by FIG. 14A. Furthermore, the intervening viral ITRs prevent any recombined genome from expressing the protein (FIG. 14A).

Figure 15:
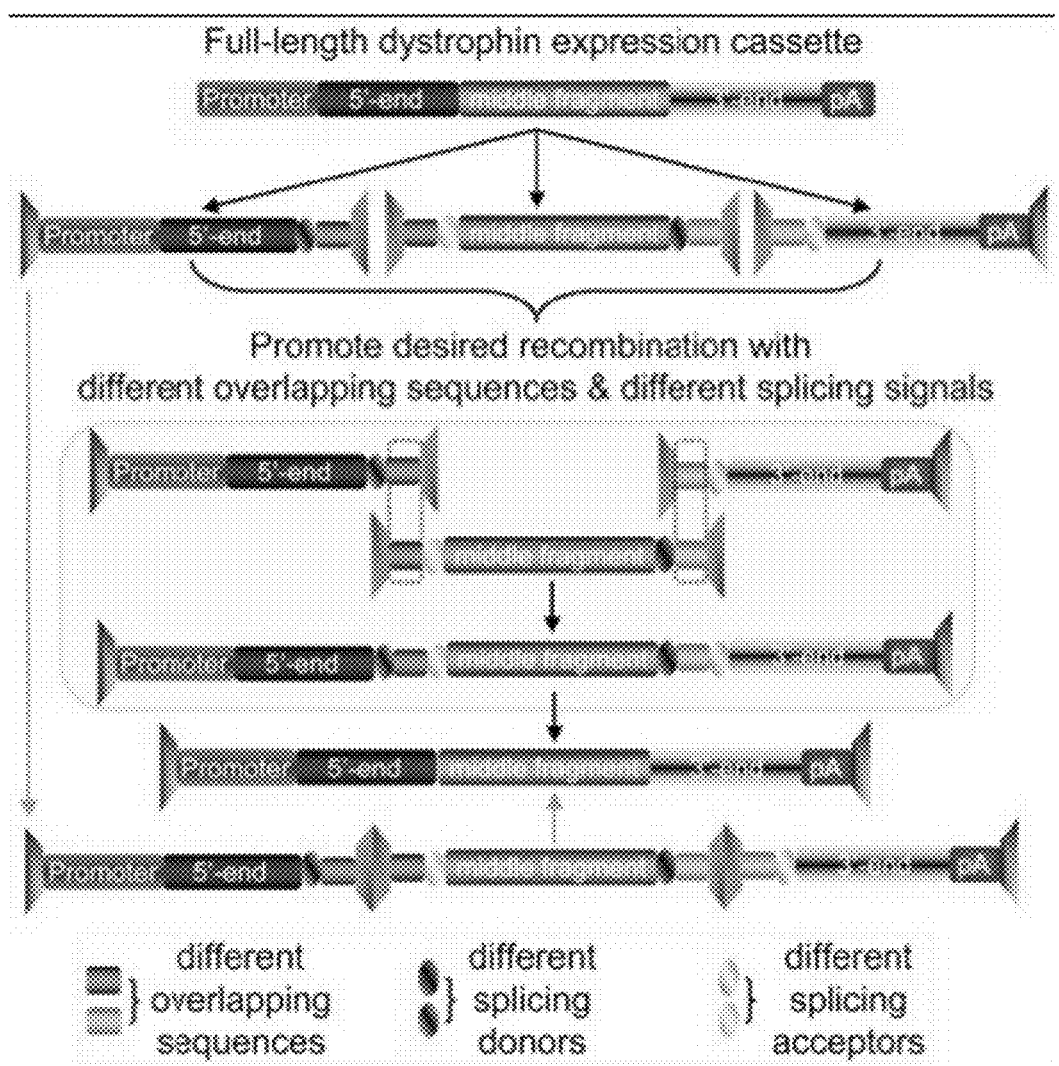
FIG. 15 is a schematic illustration of the htAAV hybrid vector design to deliver a full-length therapeutic target gene. Different AP sequences and splicing signals are used to promote unidirectional recombination.

To minimize random recombination, and improve unidirectional recombination, different ITRs were cloned on the opposite ends of the AAV vectors. AAV-5 ITR was cloned on the 5' end of the head AAV vector and the 3' end of the tail AAV vector, and AAV-2 at all other ends of the vectors (FIG. 15B). After co-infection, only the same type ITRs will recombine. This significantly reduces random recombination. In addition, by using two different splicing signals and two different AP sequences, the htAAV construction is designed to minimize random recombination for the AAV vectors and enhance unidirectional AAV recombination. See FIG. 15.

A complete set of the htAAV vectors is illustrated in FIG. 16 and includes the following components: 6 ITRs (4 AAV-2 ITRs and 2 AAV-5 ITRs; a total of 0.9 kb; each ITR is 0.15 kb), two sets of splicing signals (2 donors and 2 acceptors; a total of 0.8 kb), two sets of foreign DNA sequences, and the full-length dystrophin expression cassette (promoter, coding sequence and pA; a total of 11.86 kb) (see Example 6; FIG. 15). The 0.26 kb and 0.27 kb AP sequences we described in Example 6 (FIGS. 11 and 12) are used to mediate intergenome recombination through the overlapping pathway. Together the combined genome size of three AAV vectors is 14.62 kb.

A single AAV vector can only package a 5 kb genome, thus the maximal size of the dystrophin coding sequence that can be packaged in the head, body and tail vectors is 3.64 kb, 3.77 kb and 4.03 kb, respectively (see Table 1). The dystrophin coding sequence from ATG to exon 27 is 3786 bp (see Table 2). Thus, the dystrophin gene in the head vector can only include the first 26 exons. The dystrophin coding sequence from exon 48 to TAG (the stop codon) is 4145 bp (see Table 2). Thus, the dystrophin gene in the tail vector can only include the sequences after exon 48 (starting from exon 49). Table 2 lists a number of different combinations that can be used to split the full-length dystrophin gene in the htAAV vectors. Among these, the exon 26/27 and 48/49 junctions have the best splicing parameters (Table 2, option #3). The dystrophin gene was split at these sites to build the htAAV vectors. FIG. 16 depicts the schematic view of the head, body and tail vectors that were generated.

Figure 17:
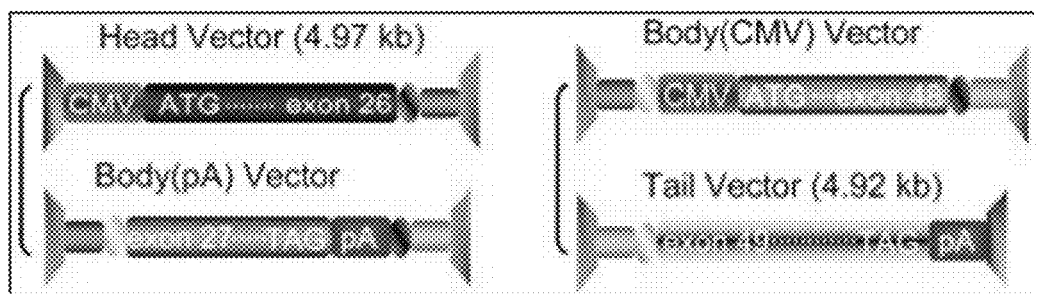
FIG. 17 is a schematic view of the control vectors used to evaluate recombination efficiency between the head/body vectors and body/tail vectors shown in FIG. 16.

To express the full-length dystrophin protein, two independent recombination events have to occur, one between the head and the body vectors and the other between the body and the tail vectors. Poor reconstitution in either one reduces full-length protein expression. To address this issue, two control vectors were generated as illustrated in FIG. 17. The first one is called Body(pA) vector, wherein an in-frame stop codon and the pA signal is inserted in the original Body vector (FIG. 17). Co-infection of the Head vector and the Body(pA) vector shows the reconstitution efficiency between the head and the body vectors. The second control vector is called Body(CMV) vector which has an engineered CMV promoter, the Kozak sequence and an in-frame ATG in the original Body vector (FIG. 17). Co-infection of the Body(CMV) vector and the Tail vector demonstrates the reconstitution efficiency between the body and the tail vectors.

In Table 2, five different combinations are listed that may be used to build the htAAV vectors. In each case, the full-length gene is split at a different set of exon-exon junctions. The same 0.26 kb and 0.27 kb AP fragments were used for reconstitution via the overlapping pathway (FIG. 11). Therefore, similar reconstitution efficiency via the overlapping pathway for both head/body and body/tail recombination was seen. To ensure the most efficient reconstitution via the trans-splicing pathway, the sites harboring the most favorable splicing values as calculated by the splicing parameters were used to build the htAAV vectors (Table 2, option #3). The other four options listed in Table 2 may alternatively be used. This combination yields the maximal overall reconstitution.

EXAMPLE 8

Local Injection and Co-Infection of the htAAV Vectors in Mdx Mice

Recombinant AAV production and local injection. Previous studies have shown that AAV-6 is the most potent AAV serotype for muscle expression after local injection (Ghosh et al., 2006; Gregorevic et al., 2004; Lai et al., 2006; Lai et al., 2005; Wang et al., 2005). Thus, AAV constructs developed in Example 7 were packaged into AAV-6 using our published protocols (Ghosh et al., 2006; Lai et al., 2006; Wang et al., 2005). The current AAV-6 yield is $1 \times 10^{10}$ vg particles/µl (vg, viral genome). The head, body and tail vectors (15 µl each at 1:1:1 ratio; $1.5 \times 10^{11}$ vg particles/vector) were injected into the tibialis anterior (TA) muscle in 2-month-old male mdx mice according to a published protocol (Duan et al., 1998; Ghosh et al., 2006). The maximum volume that a 2-month-old mdx TA muscle can receive is 45 µl. Due to a time-dependent increase in large concatamer formation after AAV infection (Duan et al., 1998), the TA muscles were harvested at 40 or 90 days post-injection to evaluate dystrophin expression (N=4 muscles).

Evaluate full-length dystrophin expression by immunofluorescence staining and western blot Serial sections of htAAV infected muscle were cut and immunostaining was performed according to published protocols (Lai et al., 2005; Liu et al., 2005; Yue et al., 2003b; Yue et al., 2004). A microsomal preparation (cell lysate enriched in membrane-associated proteins) was prepared from the remaining tissue and western blots were subsequently performed according to a published protocol (Lai et al., 2005; Yue, 2006; Yue, 2004). Immunostaining showed sarcolemmal localization. The percentage of dystrophin positive cells was quantified by a previously described morphometric method (Lai et al., 2005; Yue et al., 2006). The molecular weight and the relative level of hdAAV expression was illustrated by Western blot by comparing with serial diluted BL10 muscle lysate.

Table 3 lists 12 different dystrophin antibodies that were used that are specific to muscles from mdx, BL10 and a series of transgenic mdx mice expressing different isoforms of human dystrophin. Four antibodies detect expression from the head vector (Manex 1A, Manex 7B, Dys-3 and H-300), four antibodies detect expression from the body vector (Mandys 8, Mandys 103, Manex 44A and Manex 46B) and three antibodies will detect expression from the tail vector (Manex 50, Mandra 1 and Dys-2). Manex 4850A recognizes an epitope located between 48-50. Because this epitope is split between the body and tail vectors, the recombination efficiency between the body and tail vectors can be examined with this antibody. Dys-3, Mandys 103 and Manex 4850A only recognize human dystrophin, therefore these antibodies distinguish htAAV expression from mouse dystrophin in revertant myofibers in mdx muscle or endogenous murine dystrophin in BL10 muscle.

Controls used include: (1) uninfected mdx TA muscle; (2) BL10 TA muscle; (3) mdx TA muscle injected with individual head, body or tail vector; (4) mdx TA muscle injected with micro-dystrophin AAV vector; and (5) mdx TA muscle injected with mini-dystrophin hybrid vectors.

In the mini-dystrophin dual vector studies, efficient reconstitution was achieved in more than 80% myofibers. This transduction efficiency is comparable to that of a single AAV infection. The htAAV system reached therapeutic expression levels because the underlying mechanism(s) are the same, To ensure the dose of the htAAV vectors is sufficient for all three vectors to co-infect the same muscle nucleus, a minimum of a 7-fold increase in dosage ($1.5 \times 10^{11}$ vg particles/vector/muscle) is used as compared to the in vivo mini-dystrophin hdAAV vector study ($2 \times 10^{10}$ vg particles/vector/muscle).

EXAMPLE 9

Hybrid Tri-AAV (htAAV) Mediated Full-Length Dystrophin Expression Restores the DGC, Ameliorates Muscle Pathology and Improves Muscle Force in Mdx Mice An important biological function of dystrophin is to assemble the dystrophin-associated glycoprotein complex (DGC). htAAV mediated full-length dystrophin expression can fully restore the entire DGC including nNOS. DMD gene therapy aims to reduce muscle pathology and improve muscle force. htAAV mediated full-length dystrophin expression reduces muscle degeneration and inflammation, enhances sarcolemma integrity and improves muscle force.

Examination of the DGC by immunofluorescence staining and nNOS activity staining. Immunostaining was performed using serial muscle sections obtained in Example 8 using antibodies and immunostaining protocols to detect the representative components of the DGC including β-dystroglycan, β-sarcoglycan, δ-sarcoglycan, syntrophin, dystrobrevin and nNOS (Lai et al., 2005; Liu et al., 2005; Yue et al., 2003b; Yue et al., 2006). To further confirm nNOS immunostaining results, an established in situ nNOS activity assay was used (Kameya et al., 1999; Rothe et al., 2005; Spessert et al., 1998).

Morphological examination of muscle pathology. Hematoxylin and eosin (HE) staining was performed to quantify the percentage of centrally nucleated cells (% CN) in htAAV transduced myofibers (Liu et al., 2005). HE staining also allows estimation of muscle inflammation. Dystrophic muscle inflammation was also measured by macrophage infiltration, which was examined by immunostaining for mouse macrophage (F4/8 antibody) and non-specific esterase staining for macrophage. The sarcolemma integrity was evaluated by Evans blue dye (EBD) uptake.

Measuring twitch and tetanic muscle force, and eccentric contraction-induced muscle damage. The extensor digitorium longus (EDL) was used to measure force improvement after therapeutic interventions in mdx mice. Briefly, 10 µl hdAAV mixtures (~3.3×10$^{10}$ vg particles/vector/muscle) were injected to the left EDL muscle in 2-month-old male mdx mice (N=6 muscles) according to a published protocol (Lai et al., 2005; Liu, 2005). For the untreated control, the right EDL muscle was mock injected with equal volume HEPES buffer (N=6 muscles). Muscle physiology assays to measure specific twitch force, specific tetanic force, and force drop over 10 cycles of eccentric contraction were performed at 50 days post-injection according to a published protocol (Lai et al., 2005; Liu et al., 2005; Yue et al., 2006). All the muscle force data was compared with results in AAV microdystrophin vector and AAV mini-dystrophin trans-splicing vector treated BL10 mdx mice (Lai et al., 2005; Liu et al., 2005; Yue et al., 2006). A set of control muscles were used, including mdx BL10 and mdx individually injected with the head, body or tail vector, mdx treated with microgene and minigene AAV vectors.

The full-length dystrophin protein carries out all biological functions, therefore the htAAV vectors yield superior therapy than that can be achieved with micro- or mini-dystrophin. A full recovery of the DGC (including nNOS), an effective amelioration of muscle pathology (a reduction in % CN, inflammation and EBD uptake), an improvement in muscle force and a protection from contraction-induced injury were observed in muscle injected with the htAAV vectors.

To reduce potential complications with immunostaining as a result of DGC restoration from revertant fibers, the studies described above may alternatively be carried out in mdx4cv mice (Jackson Laboratory, Bar Harbor, Me.). Mdx4cv mice are N-ethylnitrosourea-induced dystrophin mutant model (Chapman et al., 1989). They carry 10-fold fewer revertant fibers than that of mdx mice (Danko et al., 1993; Li et al., 2006).

References

The References listed below, and all references cited in the specification are hereby incorporated by reference in their entirety.

1. Acsadi, G., G. Dickson, D. R. Love, A. Jani, F. S. Walsh, A. Gurusinghe, J. A. Wolff, and K. E. Davies. 1991. Human dystrophin expression in mdx mice after intramuscular injection of DNA constructs [see comments]. Nature 352: 815-8.
2. Albrecht, D. E., and S. C. Froehner. 2002. Syntrophins and dystrobrevins: defining the dystrophin scaffold at synapses. Neurosignals 11:123-9.
3. Alter, J., F. Lou, A. Rabinowitz, H. Yin, J. Rosenfeld, S. D. Wilton, T. A. Partridge, and Q. L. Lu. 2006. Systemic delivery of morpholino oligonucleotide restores dystrophin expression bodywide and improves dystrophic pathology. Nat Med 12:175-7.
4. Beggs, A. H., E. P. Hoffman, J. R. Snyder, K. Arahata, L. Specht, F. Shapiro, C. Angelini, H. Sugita, and L. M. Kunkel. 1991. Exploring the molecular basis for variability among patients with Becker muscular dystrophy: dystrophin gene and protein studies. Am J Hum Genet 49:54-67.
5. Bilbao, R., D. P. Reay, E. Wu, H. Zheng, V. Biermann, S. Kochanek, and P. R. Clemens. 2005. Comparison of high-capacity and first-generation adenoviral vector gene delivery to murine muscle in utero. Gene Ther 12:39-47.
6. Brenman, J. E., D. S. Chao, S. H. Gee, A. W. McGee, S. E. Craven, D. R. Santillano, Z. Wu, F. Huang, H. Xia, M. F. Peters, S. C. Froehner, and D. S. Bredt. 1996. Interaction of nitric oxide synthase with the postsynaptic density protein PSD-95 and alpha1-syntrophin mediated by PDZ domains. Cell 84:757-67.
7. Brenman, J. E., D. S. Chao, H. Xia, K. Aldape, and D. S. Bredt. 1995. Nitric oxide synthase complexed with dystrophin and absent from skeletal muscle sarcolemma in Duchenne muscular dystrophy. Cell 82:743-52.
8. Bulman, D. E., E. G. Murphy, E. E. Zubrzycka-Gaarn, R. G. Worton, and P. N. Ray. 1991. Differentiation of Duchenne and Becker muscular dystrophy phenotypes with amino- and carboxyterminal antisera specific for dystrophin. Am J Hum Genet 48:295-304.
9. Chao, D. S., J. R. Gorospe, J. E. Brenman, J. A. Rafael, M. F. Peters, S. C. Froehner, E. P. Hoffman, J. S. Chamberlain, and D. S. Bredt. 1996. Selective loss of sarcolemmal nitric oxide synthase in Becker muscular dystrophy. J Exp Med 184:609-18.
10. Chapman, V. M., D. R. Miller, D. Armstrong, and C. T. Caskey. 1989. Recovery of induced mutations for X chromosome-linked muscular dystrophy in mice. Proc Natl Acad Sci USA 86:1292-6.
11. Clemens, P. R., S. Kochanek, Y. Sunada, S. Chan, H. H. Chen, K. P. Campbell, and C. T. Caskey. 1996. In vivo muscle gene transfer of full-length dystrophin with an adenoviral vector that lacks all viral genes. Gene Ther 3:965-72.
12. Crawford, G. E., J. A. Faulkner, R. H. Crosbie, K. P. Campbell, S. C. Froehner, and J. S. Chamberlain. 2000. Assembly of the dystrophin-associated protein complex does not require the dystrophin COOH terminal domain. J Cell Biol 150:1399-410.
13. Danko, I., J. D. Fritz, J. S. Latendresse, H. Herweijer, E. Schultz, and J. A. Wolff. 1993. Dystrophin expression improves myofiber survival in mdx muscle following intramuscular plasmid DNA injection Hum Mol Genet 2:2055-61.
14. Davies, K. E., and K. J. Nowak. 2006. Molecular mechanisms of muscular dystrophies: old and new players. Nat Rev Mol Cell Biol 7:762-73.
15. Deconinck, N., and B. Dan. 2007. Pathophysiology of duchenne muscular dystrophy: current hypotheses. Pediatr Neurol 36:1-7.
16. DelloRusso, C., J. M. Scott, D. Hartigan-O'Connor, G. Salvatori, C. Barjot, A. S. Robinson, R. W. Crawford, S. V. Brooks, and J. S. Chamberlain. 2002. Functional correction of adult mdx mouse muscle using gutted adenoviral vectors expressing full-length dystrophin. Proc Natl Acad Sci USA 99:12979-84.
17. Duan, D, Yan, Z, Yue, Y, Ding, W and Engelhardt, J F 2001a. Enhancement of muscle gene delivery with pseudotyped AAV-5 correlates with myoblast differentiation. *J Virol* 75: 7662-7671.
18. Duan, D, Yue, Y and Engelhardt, J F (2003). Consequences of DNA-dependent protein kinase catalytic subunit deficiency on recombinant adeno-associated virus genome circularization and heterodimerization in muscle tissue. *J Virol* 77: 4751-4759.

19. Duan, D, Yan, Z and Engelhardt, J F. 2006. Expanding the capacity of AAV vectors. In: Bloom, M E, Cotmore, S F, Linden, R M, Parrish, C R and Kerr, J R (eds). *Parvoviruses*. Hodder Arnold; Distributed in the USA by Oxford University Press: London, N.Y. pp. 525-532.
20. Duan, D., P. Sharma, J. Yang, Y. Yue, L. Dudus, Y. Zhang, K. J. Fisher, and J. F. Engelhardt. 1998. Circular Intermediates of Recombinant Adeno-Associated Virus have Defined Structural Characteristics Responsible for Long Term Episomal Persistence In Muscle. J. Virol. 72:8568-8577.
21. Duan, D., Y. Yue, and J. F. Engelhardt. 2001b. Expanding AAV Packaging Capacity With Trans-splicing Or Overlapping Vectors: A Quantitative Comparison. Mol Ther 4:383-91.
22. Duan, D., Y. Yue, Z. Yan, and J. F. Engelhardt. 2000. A new dual-vector approach to enhance recombinant adeno-associated virus-mediated gene expression through intermolecular cis activation. Nat. Med. 6:595-8.
23. Dudley, R. W., Y. Lu, R. Gilbert, S. Matecki, J. Nalbantoglu, B. J. Petrof, and G. Karpati. 2004. Sustained improvement of muscle function one year after full-length dystrophin gene transfer into mdx mice by a gutted helper-dependent adenoviral vector. Hum Gene Ther 15:145-56.
24. Emery, A. E. 1991. Population frequencies of inherited neuromuscular diseases—a world survey. Neuromuscul Disord 1:19-29.
25. Ervasti, J. M. 2007. Dystrophin, its interactions with other proteins, and implications for muscular dystrophy. Biochim Biophys Acta 1772:108-17.
26. Ervasti, J. M., and K. P. Campbell. 1991. Membrane organization of the dystrophin-glycoprotein complex. Cell 66:1121-31.
27. Fechner, H., A. Haack, H. Wang, X. Wang, K. Eizema, M. Pauschinger, R. Schoemaker, R. Veghel, A. Houtsmuller, H. P. Schultheiss, J. Lamers, and W. Poller. 1999. Expression of coxsackie adenovirus receptor and alphav-integrin does not correlate with adenovector targeting in vivo indicating anatomical vector barriers. Gene Ther 6:1520-35.
28. Fischer, A C, Smith, C I, Cebotaru, L, Zhang, X, Askin, F B, Wright, J et al. (2007). Expression of a truncated cystic fibrosis transmembrane conductance regulator with an AAV5-pseudotyped vector in primates. *Mol Ther* 15: 756-763.
29. Flotte, T R, Afione, S A, Solow, R, Drumm, M L, Markakis, D, Guggino, W B et al. (1993). Expression of the cystic fibrosis transmembrane conductance regulator from a novel adeno-associated virus promoter. *J Biol Chem* 268: 3781-3790.
30. Flotte, T R (2007). Gene therapy: the first two decades and the current state-of-the-art. *J Cell Physiol* 213: 301-305.
31. Fu, H, Muenzer, J, Samulski, R J, Breese, G, Sifford, J, Zeng, X et al. (2003). Self-complementary adeno-associated virus serotype 2 vector: global distribution and broad dispersion of AAV-mediated transgene expression in mouse brain. *Mol Ther* 8: 911-917.
32. Ghosh, A. 2007a. Rational design of split gene vectors to expand the packaging capacity of adenoassociated viral vectors. Ph.D. Thesis. University of Missouri, Columbia.
33. Ghosh, A., Y. Yue, and D. Duan. 2006. Viral serotype and the transgene sequence influence overlapping adeno-associated viral (AAV) vector-mediated gene transfer in skeletal muscle. J. Gene Med. 8:298-305.
34. Ghosh, A., Y. Yue, Y. Lai, and D. Duan. 2008. A hybrid vector system expands adeno-associated viral vector packaging capacity in a transgene independent manner. Mol Ther 16:124-130.
35. Ghosh, A., Y. Yue, C. Long, B. Bostick, and D. Duan. 2007b. Efficient Whole-body Transduction with Trans-splicing Adeno-associated Viral Vectors. Mol Ther 15:750-5.
36. Gilbert, R., R. W. Dudley, A. B. Liu, B. J. Petrof, J. Nalbantoglu, and G. Karpati. 2003. Prolonged dystrophin expression and functional correction of mdx mouse muscle following gene transfer with a helper-dependent (gutted) adenovirus-encoding murine dystrophin. Hum Mol Genet 12:1287-99.
37. Gilbert, R., A. Liu, B. Petrof, J. Nalbantoglu, and G. Karpati. 2002. Improved Performance of a Fully Gutted Adenovirus Vector Containing Two Full-Length Dystrophin cDNAs Regulated by a Strong Promoter. Mol Ther 6:501.
38. Gilbert, R., J. Nalbantoglu, J. M. Howell, L. Davies, S. Fletcher, A. Amalfitano, B. J. Petrof, A. Kamen, B. Massie, and G. Karpati. 2001. Dystrophin expression in muscle following gene transfer with a fully deleted ("gutted") adenovirus is markedly improved by trans-acting adenoviral gene products. Hum Gene Ther 12:1741-55.
39. Gilchrist, S. C., M. P. Ontell, S. Kochanek, and P. R. Clemens. 2002. Immune response to full-length dystrophin delivered to Dmd muscle by a high-capacity adenoviral vector. Mol Ther 6:359-68.
40. Grady, R. M., R. W. Grange, K. S. Lau, M. M. Maimone, M. C. Nichol, J. T. Stull, and J. R. Sanes. 1999. Role for alpha-dystrobrevin in the pathogenesis of dystrophin-dependent muscular dystrophies. Nat Cell Biol 1:215-20.
41. Grady, R. M., H. Zhou, J. M. Cunningham, M. D. Henry, K. P. Campbell, and J. R. Sanes. 2000. Maturation and maintenance of the neuromuscular synapse: genetic evidence for roles of the dystrophin-glycoprotein complex. Neuron 25:279-93.
42. Gregorevic, P., M. J. Blankinship, J. M. Allen, R. W. Crawford, L. Meuse, D. G. Miller, D. W. Russell, and J. S. Chamberlain. 2004. Systemic delivery of genes to striated muscles using adeno-associated viral vectors. Nat Med 10:828-34.
43. Halbert, C. L., J. M. Allen, and A. D. Miller. 2002. Efficient mouse airway transduction following recombination between AAV vectors carrying parts of a larger gene. Nat Biotechnol 20:697-701.
44. Harper, S. Q., M. A. Hauser, C. DelloRusso, D. Duan, R. W. Crawford, S. F. Phelps, H. A. Harper, A. S. Robinson, J. F. Engelhardt, S. V. Brooks, and J. S. Chamberlain. 2002. Modular flexibility of dystrophin: implications for gene therapy of Duchenne muscular dystrophy. Nat Med 8:253-61.
45. Hillier, B. J., K. S. Christopherson, K. E. Prehoda, D. S. Bredt, and W. A. Lim. 1999. Unexpected modes of PDZ domain scaffolding revealed by structure of nNOS-syntrophin complex. Science 284:812-5.
46. Hoffman, E. P. 1993. Genotype/phenotype correlations in Duchenne/Becker dystrophy. Mol Cell Biol Hum Dis Ser 3:12-36.
47. Hoffman, E. P., R. H. Brown, Jr., and L. M. Kunkel. 1987. Dystrophin: the protein product of the Duchenne muscular dystrophy locus. Cell 51:919-28.
48. Hoffman, E. P., K. H. Fischbeck, R. H. Brown, M. Johnson, R. Medori, J. D. Loike, J. B. Harris, R. Waterston, M. Brooke, L. Specht, and et al. 1988. Characterization of dystrophin in muscle-biopsy specimens from patients with Duchenne's or Becker's muscular dystrophy. N Engl J Med 318:1363-8.

49. Hoffman, E. P., L. M. Kunkel, C. Angelini, A. Clarke, M. Johnson, and J. B. Harris. 1989. Improved diagnosis of Becker muscular dystrophy by dystrophin testing. Neurology 39:1011-7.
50. Huang, X., F. Poy, R. Zhang, A. Joachimiak, M. Sudol, and M. J. Eck. 2000. Structure of a WW domain containing fragment of dystrophin in complex with beta-dystroglycan. Nat Struct Biol 7:634-8.
51. Jiang, Z., G. Schiedner, S. C. Gilchrist, S. Kochanek, and P. R. Clemens. 2004. CTLA4Ig delivered by high-capacity adenoviral vector induces stable expression of dystrophin in mdx mouse muscle. Gene Ther 11:1453-61.
52. Jung, D., B. Yang, J. Meyer, J. S. Chamberlain, and K. P. Campbell. 1995. Identification and characterization of the dystrophin anchoring site on beta-dystroglycan. J Biol Chem 270:27305-10.
53. Kameya, S., Y. Miyagoe, l. Nonaka, T. Ikemoto, M. Endo, K. Hanaoka, Y. Nabeshima, and S. Takeda. 1999. alpha1-syntrophin gene disruption results in the absence of neuronal-type nitric-oxide synthase at the sarcolemma but does not induce muscle degeneration. J Biol Chem 274: 2193-200.
54. Koenig, M., A. H. Beggs, M. Moyer, S. Scherpf, K. Heindrich, T. Bettecken, G. Meng, C. R. Muller, M. Lindlof, H. Kaariainen, and et al. 1989. The molecular basis for Duchenne versus Becker muscular dystrophy: correlation of severity with type of deletion. Am J Hum Genet 45:498-506.
55. Koenig, M., A. P. Monaco, and L. M. Kunkel. 1988. The complete sequence of dystrophin predicts a rod-shaped cytoskeletal protein. Cell 53:219-26.
56. Kunkel, L. M. 2005. 2004 William Allan Award address. Cloning of the DMD gene. Am J Hum Genet 76:205-14.
57. Kunkel, L. M., and E. P. Hoffman. 1989. Duchenne/Becker muscular dystrophy: a short overview of the gene, the protein, and current diagnostics. Br Med Bull 45:630-43.
58. Lai, Y., Y. Yue, M. Liu, and D. Duan. 2006. Synthetic intron improves transduction efficiency of transsplicing adeno-associated viral vectors. Hum Gene Ther 17:1036-42.
59. Lai, Y., Y. Yue, M. Liu, A. Ghosh, J. F. Engelhardt, J. S. Chamberlain, and D. Duan. 2005. Efficient in vivo gene expression by trans-splicing adeno-associated viral vectors. Nat Biotechnol 23:1435-9.
60. Li, D., Yue, Y., and Duan, D. 2008. Preservation of Muscle Force in Mdx3cv Mice Correlates with Low-Level Expression of a Near Full-Length Dystrophin Protein. Am. J. Path 172:1332-41.
61. Li, S., E. Kimura, R. Ng, B. M. Fall, L. Meuse, M. Reyes, J. A. Faulkner, and J. S. Chamberlain. 2006. A highly functional mini-dystrophin/GFP fusion gene for cell and gene therapy studies of Duchenne muscular dystrophy. Hum Mol Genet 15:1610-22.
62. Liu, M., Y. Yue, S. Q. Harper, R. W. Grange, J. S. Chamberlain, and D. Duan. 2005. Adeno-associated virus-mediated micro-dystrophin expression protects young Mdx muscle from contraction-induced injury. Mol Ther 11:245-56.
63. Matecki, S., R. W. Dudley, M. Divangahi, R. Gilbert, J. Nalbantoglu, G. Karpati, and B. J. Petrof. 2004. Therapeutic gene transfer to dystrophic diaphragm by an adenoviral vector deleted of all viral genes. Am J Physiol Lung Cell Mol Physiol 287:L569-76.
64. McCarty, D M, Fu, H, Monahan, P E, Toulson, C E, Naik, P and Samulski, R J (2003). Adeno-associated virus terminal repeat (TR) mutant generates self-complementary vectors to overcome the rate-limiting step to transduction in vivo. Gene Ther 10: 2112-2118.
65. Nakai, H, Storm, T A and Kay, M A (2000). Increasing the size of rAAV-mediated expression cassettes in vivo by intermolecular joining of two complementary vectors. Nat Biotechnol 18: 527-532.
66. Nalbantoglu, J., G. Pari, G. Karpati, and P. C. Holland. 1999. Expression of the primary coxsackie and adenovirus receptor is downregulated during skeletal muscle maturation and limits the efficacy of adenovirus-mediated gene delivery to muscle cells. Hum Gene Ther 10:1009-19.
67. Ostedgaard, L S, Zabner, J, Vermeer, D W, Rokhlina, T, Karp, P H, Stecenko, A A et al. (2002). CFTR with a partially deleted R domain corrects the cystic fibrosis chloride transport defect in human airway epithelia in vitro and in mouse nasal mucosa in vivo. *Proc Natl Acad Sci USA* 99: 3093-3098.
68. Ostedgaard, L S, Rokhlina, T, Karp, P H, Lashmit, P, Afione, S, Schmidt, M et al. (2005). A shortened adeno-associated virus expression cassette for CFTR gene transfer to cystic fibrosis airway epithelia. *Proc Natl Acad Sci USA* 102: 2952-2957.
69. Peters, M. F., M. E. Adams, and S. C. Froehner. 1997. Differential association of syntrophin pairs with the dystrophin complex. J Cell Biol 138:81-93.
70. Petrof, B. J. 1998. The molecular basis of activity-induced muscle injury in Duchenne muscular dystrophy. Mol Cell Biochem 179:111-23.
71. Petrof, B. J. 2002. Molecular pathophysiology of myofiber injury in deficiencies of the dystrophinglycoprotein complex. Am J Phys Med Rehabil 81:S162-74.
72. Phelps, S. F., M. A. Hauser, N. M. Cole, J. A. Rafael, R. T. Hinkle, J. A. Faulkner, and J. S. Chamberlain. 1995. Expression of full-length and truncated dystrophin minigenes in transgenic mdx mice. Hum Mol Genet 4:1251-8.
73. Rando, T. A. 2001. The dystrophin-glycoprotein complex, cellular signaling, and the regulation of cell survival in the muscular dystrophies. Muscle Nerve 24:1575-1594
74. Reich, S J, Auricchio, A, Hildinger, M, Glover, E, Maguire, A M, Wilson, J M et al. (2003). Efficient trans-splicing in the retina expands the utility of adeno-associated virus as a vector for gene therapy. *Hum Gene Ther* 14: 37-44.
75. Romero, N. B., S. Braun, O. Benveniste, F. Leturcq, J. Y. Hogrel, G. E. Morris, A. Barois, B. Eymard, C. Payan, V. Ortega, A. L. Boch, L. Lejean, C. Thioudellet, B. Mourot, C. Escot, A. Choquel, D. Recan, J. C. Kaplan, G. Dickson, D. Klatzmann, V. Molinier-Frenckel, J. G. Guillet, P. Squiban, S. Herson, and M. Fardeau. 2004. Phase I study of dystrophin plasmid-based gene therapy in Duchenne/Becker muscular dystrophy. Hum Gene Ther 15:1065-76.
76. Rothe, F., K. Langnaese, and G. Wolf. 2005. New aspects of the location of neuronal nitric oxide synthase in the skeletal muscle: a light and electron microscopic study. Nitric Oxide 13:21-35.
77. Sadoulet-Puccio, H. M., M. Rajala, and L. M. Kunkel. 1997. Dystrobrevin and dystrophin: an interaction through coiled-coil motifs. Proc Natl Acad Sci USA 94:12413-8.
78. Sander, M., B. Chavoshan, S. A. Harris, S. T. Iannaccone, J. T. Stull, G. D. Thomas, and R. G. Victor. 2000. Functional muscle ischemia in neuronal nitric oxide synthase-deficient skeletal muscle of children with Duchenne muscular dystrophy. Proc Natl Acad Sci USA 97:13818-23.

79. Sironi, M., U. Pozzoli, R. Cagliani, G. P. Comi, A. Bardoni, and N. Bresolin. 2001. Analysis of splicing parameters in the dystrophin gene: relevance for physiological and pathogenetic splicing mechanisms. Hum Genet 109: 73-84.

80. Spessert, R., and M. Claassen. 1998. Histochemical differentiation between nitric oxide synthaserelated and -unrelated diaphorase activity in the rat olfactory bulb. Histochem J 30:41-50.

81. Sun, L., J. Li, and X. Xiao. 2000. Overcoming adeno-associated virus vector size limitation through viral DNA heterodimerization. Nat. Med. 6:599-602.

82. Thomas, G. D., M. Sander, K. S. Lau, P. L. Huang, J. T. Stull, and R. G. Victor. 1998. Impaired metabolic modulation of alpha-adrenergic vasoconstriction in dystrophin-deficient skeletal muscle. Proc Natl Acad Sci USA 95:15090-5.

83. Thomas, G. D., P. W. Shaul, I. S. Yuhanna, S. C. Froehner, and M. E. Adams. 2003. Vasomodulation by skeletal muscle-derived nitric oxide requires alpha-syntrophin-mediated sarcolemmal localization of neuronal Nitric oxide synthase. Circ Res 92:554 60.

84. Tidball, J. G., and M. Wehling-Henricks. 2007. The role of free radicals in muscular dystrophy. J Appl Physiol 102: 1677-86.

85. Tochio, H., Q. Zhang, P. Mandal, M. Li, and M. Zhang. 1999. Solution structure of the extended neuronal nitric oxide synthase PDZ domain complexed with an associated peptide. Nat Struct Biol 6:417-21.

86. Uchida, Y., Y. Maeda, E. Kimura, S. Yamashita, Y. Nishida, T. Arima, T. Hirano, E. Uyama, S. Mita, and M. Uchino. 2005. Effective repetitive dystrophin gene transfer into skeletal muscle of adult mdx mice using a helper-dependent adenovirus vector expressing the coxsackievirus and adenovirus receptor (CAR) and dystrophin. J Gene Med 7:1010-22.

87. Wang, B, Li, J and Xiao, X (2000). Adeno-associated virus vector carrying human minidystrophin genes effectively ameliorates muscular dystrophy in mdx mouse model. *Proc Natl Acad Sci USA* 97: 13714-13719.

88. Wang, Y. 2006. HSV-1 amplicon vectors are an efficient gene transfer system for skeletal muscle cells. Curr Gene Ther 6:371-81.

89. Wang, Z., T. Zhu, C. Qiao, L. Zhou, B. Wang, J. Zhang, C. Chen, J. Li, and X. Xiao. 2005. Adenoassociated virus serotype 8 efficiently delivers genes to muscle and heart. Nat Biotechnol 23:321-8.

90. Wang, Z, Ma, H I, Li, J, Sun, L, Zhang, J and Xiao, X (2003). Rapid and highly efficient transduction by double-stranded adeno-associated virus vectors in vitro and in vivo. *Gene Ther* 10: 2105-2111.

91. Wolff, J. A., and V. Budker. 2005. The mechanism of naked DNA uptake and expression. Adv Genet 54:3-20.

92. Xu, Z, Yue, Y, Lai, Y, Ye, C, Qiu, J, Pintel, D J et al. (2004). Trans-splicing adeno-associated viral vector-mediated gene therapy is limited by the accumulation of spliced mRNA but not by dual vector coinfection efficiency. *Hum Gene Ther* 15: 896-905.

93. Yan, Z., D. C. Lei-Butters, Y. Zhang, R. Zak, and J. F. Engelhardt. 2007. Hybrid adeno-associated virus bearing nonhomologous inverted terminal repeats enhances dual-vector reconstruction of minigenes in vivo. Hum Gene Ther 18:81-7.

94. Yan, Z., R. Zak, Y. Zhang, and J. F. Engelhardt. 2005. Inverted terminal repeat sequences are important for intermolecular recombination and circularization of adeno-associated virus genomes. J Virol 79:364-79.

95. Yan, Z., Y. Zhang, D. Duan, and J. F. Engelhardt. 2000. From the Cover: Trans-splicing vectors expand the utility of adeno-associated virus for gene therapy. Proc. Natl. Acad. Sci. USA 97:6716-6721.

96. Yang, J., W. Zhou, Y. Zhang, T. Zidon, T. Ritchie, and J. F. Engelhardt. 1999. Concatamerization of Adeno-associated Viral Circular Genomes Occurs Through Intermolecular Recombination. J. Virol. 73:9468-77.

97. Yoshimura, M., Sakamoto, M., Ikemoto, M., Mochizuki, Y., Yuasa, K., Miyagoe-Suzuki, Y., and Takeda, S. 2004. AAV Vector-Mediated Microdystrophin Expression in a Relatively Small Percentage of mdx Myofibers Improved the mdx Phenotype. Mol. Ther. 10:821-28.

98. Yue, Y., and D. Duan. 2003a. Double strand interaction is the predominant pathway for intermolecular recombination of adeno-associated viral genomes. Virology 313:1-7.

99. Yue, Y., Z. Li, S. Q. Harper, R. L. Davisson, J. S. Chamberlain, and D. Duan. 2003b. Microdystrophin Gene Therapy of Cardiomyopathy Restores Dystrophin-Glycoprotein Complex and Improves Sarcolemma Integrity in the Mdx Mouse Heart. Circulation 108:1626-32.

100. Yue, Y., M. Liu, and D. Duan. 2006. C-terminal truncated microdystrophin recruits dystrobrevin and syntrophin to the dystrophin-associated glycoprotein complex and reduces muscular dystrophy in symptomatic utrophin/dystrophin double knock-out mice. Mol Ther 14:79-87.

101. Yue, Y., J. W. Skimming, M. Liu, T. Strawn, and D. Duan. 2004. Full-length dystrophin expression in half of the heart cells ameliorates beta-isoproterenol-induced cardiomyopathy in mdx mice. Hum Mol Genet 13:1669-75.

102. Yue, Y and Duan, D (2002). Development of multiple cloning site cis-vectors for recombinant adeno-associated virus production. *Biotechniques* 33: 672, 674, 676-678.

103. Zhang, L, Wang, D, Fischer, H, Fan, P D, Widdicombe, J H, Kan, Y W et al. (1998). Efficient expression of CFTR function with adeno-associated virus vectors that carry shortened CFTR genes. *Proc Natl Acad Sci USA* 95: 10158-10163.

TABLE 1

Table 1. The size of each vector in the tri-AAV system (in kb)

| Components | Head Vector | Body Vector | Tail Vector |
|---|---|---|---|
| ITRs (2 for each AAV) | 0.3 | 0.3 | 0.3 |
| Promoter | 0.6 | — | — |
| polyA | — | — | 0.2 |
| Splicing donor | 0.2 | 0.2 | — |
| Splicing acceptor | — | 0.2 | 0.2 |
| 0.26 kb AP sequence | 0.26 | 0.26 | — |
| 0.27 kb AP sequence | — | 0.27 | 0.27 |
| Dystrophin sequence | 3.64 | 3.77 | 4.03 |
| Sub total | 5 | 5 | 5 |

TABLE 2

Table 2. Putative dystrophin gene splitting sites and the predicted splicing parameters

| | | Head Vector (≦3.64 kb)* | | | Body Vector (≦3.77 kb)* | | Tail Vector (≦4.03 kb)* | | |
|---|---|---|---|---|---|---|---|---|---|
| | | Size (bp)** | Junction | Splicing Parameters*** | | Size (bp)** | | Size (bp)** | Junction | Splicing Parameters*** |
| | ATG to exon 25 | 3432 | exons 25/26 | 0.70, 0.82, −7.6 | exons 26 to 47 | | exon 48 to stop codon | 4145 | | |
| #1 | ATG to exon 25 | 3432 | exons 25/26 | 0.70, 0.82, −7.6 | exons 26 to 48 | 3667 | exon 49 to stop codon | 3959 | exons 48/49 | 0.85, 0.96, −10.2 |
| #2 | ATG to exon 25 | 3432 | exons 25/26 | 0.70, 0.82, −7.6 | exons 26 to 49 | 3769 | exon 50 to stop codon | 3857 | exons 49/50 | 0.81, 0.83, −5.9 |
| | ATG to exon 25 | 3432 | exons 25/26 | 0.70, 0.82, −7.6 | exons 26 to 50 | 3878 | exon 51 to stop codon | 3748 | | |
| #3 | ATG to exon 26 | 3603 | exons 26/27 | 0.80, 0.96, −7.3 | exons 27 to 48 | 3496 | exon 49 to stop codon | 3959 | exons 48/49 | 0.85, 0.96, −10.2 |
| #4 | ATG to exon 26 | 3603 | exons 26/27 | 0.80, 0.96, −7.3 | exons 27 to 49 | 3598 | exon 50 to stop codon | 3857 | exons 49/50 | 0.81, 0.83, −5.9 |
| #5 | ATG to exon 26 | 3603 | exons 26/27 | 0.80, 0.96, −7.3 | exons 27 to 50 | 3707 | exon 51 to stop codon | 3748 | exons 50/51 | 0.79, 0.63, −7.5 |
| | ATG to exon 26 | 3603 | exons 26/27 | 0.80, 0.96, −7.3 | exons 27 to 51 | 3940 | exon 52 to stop codon | 3515 | | |
| | ATG to exon 27 | 3786 | | | | | | | | |

*The number in the bracket is the maximal size of the dystrophin gene sequence that can fit into the respective vector (see Table 1).
**The size of the dystrophin gene framgent is based on Koenig et al Cell 50: 509-517, 1987 and Hoffman et al Cell 51: 919-928, 1987.
***In the order of 5' conserved splicing value, 3' conserved splicing value and free energy exchange during U1 snRNA annealing (Kcal/mol).

TABLE 3

Table 3. Epitope specific antibodies that we have tested for this project

| | Epitope | Name | Supply | Comment |
|---|---|---|---|---|
| Head Vector | exons 1-10 | Manex 1A | Dr. Glenn Moris | |
| | exons 7 & 8 | Manex 7B | Dr. Glenn Moris | |
| | exons 9 & 10 | Dys-3 | Novocastra, UK | Human specific |
| Body Vector | exons 18-23 | H-300 | Santa Cruz, CA | |
| | exon 32 | Mandys 8 | Sigma, MO | |
| | exon 43 | Mandys 103 | Dr. Glenn Moris | Human specific |
| | exon 44 | Manex 44A | Dr. Glenn Moris | |
| | exon 46 | Manex 46B | Dr. Glenn Moris | |
| Tail Vector | exons 48-50 | Manex 4850A | Dr. Glenn Moris | Human specific |
| | exons 48-50 | Manex 4850A | Dr. Glenn Moris | Human specific |
| | exon 50 | Manex 50 | Dr. Glenn Moris | |
| | exon 77 | Mandra 1 | Dr. Glenn Moris | |
| | exon 78 | Dys-2 | Novocastra, UK | |

What is claimed is:

1. A hybrid dual AAV (hdAAV) vector system comprising:
   (a) a first recombinant AAV vector comprising:
      (i) a first DNA segment comprising a 5'-inverted terminal repeat (5'-ITR) of AAV,
      (ii) a second DNA segment comprising a first portion of an open reading frame of a target gene operably linked to a promoter,
      (iii) a third DNA segment comprising a splice donor site,
      (iv) a fourth DNA segment comprising an alkaline phosphatase (AP) gene fragment, and
      (v) a fifth DNA segment comprising a 3'-inverted terminal repeat (3'-ITR) of AAV; and
   (b) a second recombinant AAV vector comprising:
      (i) a first DNA segment comprising a 5'-ITR of AAV,
      (ii) a second DNA segment comprising the AP gene fragment,
      (iii) a third DNA segment comprising a splice acceptor site,
      (iv) a fourth DNA segment comprising a second portion of the open reading frame of the target gene, which together with the first portion of the open reading frame encodes the target gene (polypeptide), operably linked with a polyadenylation (pA) signal, and
      (v) a fifth DNA segment comprising a 3'-ITR of AAV.

2. The hdAAV vector system of claim 1, wherein the target gene is between 5 kb and 10 kb.

3. The hdAAV vector system of claim 1, wherein target gene is a mini-dystrophin or micro-dystrophin gene.

4. The hdAAV vector system of claim 1, wherein the AP gene fragment may be selected from the DNA segments of SEQ ID NOs:1-6.

5. The hdAAV vector system of claim 1, wherein the AP gene fragment is SEQ ID NO:4.

6. The hdAAV vector system of claim 1, wherein the AP gene fragment is SEQ ID NO:6.

7. A hybrid tri-AAV (htAAV) vector system comprising:
   (a) a first recombinant AAV vector comprising:
      (i) a first DNA segment comprising a 5'-inverted terminal repeat (5'-ITR) of AAV,
      (ii) a second DNA segment comprising a head portion of an open reading frame of a target gene operably linked to a promoter,
      (iii) a third DNA segment comprising a first splicing donor site,
      (iv) a fourth DNA segment comprising an AP-head sequence, and
      (v) a fifth DNA segment comprising a 3'-inverted terminal repeat (3'-ITR) of AAV;
   (b) a second recombinant AAV vector comprising:
      (i) a first DNA segment comprising a 5'-ITR of AAV,
      (ii) a second DNA segment comprising the AP-head sequence,
      (iii) a third DNA segment comprising a first splicing acceptor site,
      (iv) a fourth DNA segment comprising a middle portion of the open reading frame of the target gene,
      (v) a fifth DNA segment comprising a second splicing donor site,
      (vi) a sixth DNA segment comprising a AP-tail sequence, and
      (vii) a seventh DNA segment comprising a 3'-ITR of AAV; and
   (c) a third recombinant AAV vector comprising:
      (i) a first DNA segment comprising a 5'-ITR of AAV,
      (ii) a second DNA segment comprising the AP-tail sequence,
      (iii) a third DNA segment comprising a second splicing acceptor site,
      (iv) a fourth DNA segment comprising a tail portion of the open reading frame of the target gene, which together with the head and middle portions encodes the target gene, operably linked with a pA signal, and
      (v) a fifth DNA segment comprising a 3'-ITR of AAV.

8. The htAAV vector system of claim 7, wherein the 5'-ITR of the first recombinant AAV vector and the 3'-ITR of the third recombinant AAV vector are from AAV serotype-5 and wherein the 3'-ITR of the first recombinant AAV vector, the 5'-ITR and 3'-ITR of the second recombinant AAV vector and the 5'-ITR of the third recombinant AAV vector are from AAV serotype-2.

9. The htAAV vector system of claim 7, wherein the target gene is between 10 kb and 15 kb.

10. The htAAV vector system of claim 7, wherein the target gene is a full-length dystrophin coding sequence.

11. The htAAV vector system of claim 7, wherein the head portion of the therapeutic target gene is SEQ ID NO:7, the middle portion of the therapeutic target gene is SEQ ID NO:8, and the tail portion of the therapeutic target gene is SEQ ID NO:9.

12. The htAAV vector system of claim 7, wherein the AP-head sequence is SEQ ID NO:4.

13. The htAAV vector system of claim 7, wherein the AP-tail sequence is SEQ ID NO:6.

14. A method of treating a clinical disease caused at least in part by a defective gene comprising:
   providing a hybrid AAV vector system according to claim 1 or claim 7, capable of expressing a therapeutic target gene, wherein the therapeutic target gene is capable of replacing, restoring or counteracting the effects of the defective gene; and administering a therapeutic amount of said vector system to a subject wherein said therapeutic target gene is expressed at levels having a therapeutic effect.

15. The method of claim 14 wherein the clinical disease is caused by a single defective gene.

16. The method of claim 14 wherein the clinical disease is DMD, BMD, XLDC.

17. The method of claim 14 wherein the target gene is dystrophin.

18. The method of claim 14 wherein the hybrid vector system is an hdAAV vector system and the target gene is a mini-or micro-dystrophin gene.

19. The method of claim 14 wherein the hybrid vector system is an htAAV vector system and the target gene is a full-length dystrophin coding sequence.

* * * * *

UNITED STATES PATENT AND TRADEMARK OFFICE
CERTIFICATE OF CORRECTION

PATENT NO. : 8,236,557 B2
APPLICATION NO. : 12/473651
DATED : August 7, 2012
INVENTOR(S) : Dongsheng Duan et al.

Page 1 of 1

It is certified that error appears in the above-identified patent and that said Letters Patent is hereby corrected as shown below:

Cover page, at (75), Inventor, replace "Duan Dongsheng;" with -- Dongsheng Duan; --

Column 1, line 13, under the heading "GRANT STATEMENT", replace "This invention was made at least in part from" with -- This invention was made with --; lines 15-16, replace "The Government has certain rights in this invention." with -- The government has certain rights in the invention. --

Signed and Sealed this
Fifteenth Day of January, 2013

David J. Kappos
*Director of the United States Patent and Trademark Office*

SEQUENCE LISTING

<160> NUMBER OF SEQ ID NOS: 21

<210> SEQ ID NO 1
<211> LENGTH: 865
<212> TYPE: DNA
<213> ORGANISM: Homo sapiens

<400> SEQUENCE: 1

```
ccccgggtgc gcggcgtcgg tggtgccggc gggggggcgcc aggtcgcagg cggtgtaggg      60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
cgtgtaggcc ttcctgtccc gggccttgcc agcggccagc ccgatgaagg agctccctcg     360 caggggtag cctccgaagg agaagacgtg ggagtggtcg gcagtgacga ggctcagcgt     420
gtcctcctcg ctggtgagct ggcccgccct ctcaatggcg tcgtcgaaca tgatcgtctc     480
```

```
agtcagtgcc cggtaagccc tgctttcatg atgaccatgg tcgatgcgac caccctccac      540
gaagaggaag aagccgcggg ggtgtctgct cagcaggcgc agggcagcct ctgtcatctc      600
catcagggag gggtccagtg tggagtctcg gtggatctcg tatttcatgt ctccaggctc      660
aaagagaccc atgagatggg tcacagacgg gtccagggaa gcctgcatga gctcagtgcg      720
gttccacacg taccgggcac cctggcgttc gccgagccat tcctgcacca gattcttccc      780
gtccagcctg gtcccacctt ggctgtagtc atctgggtac tcagggtctg gggttcccat      840
gcgaaacatg tactttcggc ctcca                                            865

<210> SEQ ID NO 2
<211> LENGTH: 437
<212> TYPE: DNA
<213> ORGANISM: Homo sapiens

<400> SEQUENCE: 2
ccccgggtgc gcggcgtcgg tggtgccggc gggggcgcc aggtcgcagg cggtgtaggg       60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttccgt ataggaggac     300
cgtgtaggcc ttcctgtccc gggccttgcc agcggccagc ccgatgaagg agctccctcg     360 caggggtag cctccgaagg agaagacgtg ggagtggtcg gcagtgacga ggctcagcgt      420
gtcctcctcg ctggtga                                                    437

<210> SEQ ID NO 3
<211> LENGTH: 428
<212> TYPE: DNA
<213> ORGANISM: Homo sapiens

<400> SEQUENCE: 3
gctggcccgc cctctcaatg gcgtcgtcga acatgatcgt ctcagtcagt gcccggtaag      60
ccctgctttc atgatgacca tggtcgatgc gaccaccctc cacgaagagg aagaagccgc     120
gggggtgtct gctcagcagg cgcagggcag cctctgtcat ctccatcagg gaggggtcca     180
gtgtggagtc tcggtggatc tcgtatttca tgtctccagg ctcaaagaga cccatgagat     240
gggtcacaga cgggtccagg gaagcctgca tgagctcagt gcggttccac acgtaccggg     300
caccctggcg ttcgccgagc cattcctgca ccagattctt cccgtccagc ctggtcccac     360
cttggctgta gtcatctggg tactcagggt ctggggttcc catgcgaaac atgtactttc     420
ggcctcca                                                              428

<210> SEQ ID NO 4
<211> LENGTH: 287
<212> TYPE: DNA
<213> ORGANISM: Homo sapiens

<400> SEQUENCE: 4
ccccgggtgc gcggcgtcgg tggtgccggc gggggcgcc aggtcgcagg cggtgtaggg       60
ctccaggcag gcggcgaagg ccatgacgtg cgctatgaag gtctgctcct gcacgccgtg     120
aaccaggtgc gcctgcgggc cgcgcgcgaa caccgccacg tcctcgcctg cgtgggtctc     180
ttcgtccagg ggcactgctg actgctgccg atactcgggg ctcccgctct cgctctcggt     240
aacatccggc cgggcgccgt ccttgagcac atagcctgga ccgtttc                   287
```

<210> SEQ ID NO 5
<211> LENGTH: 290
<212> TYPE: DNA
<213> ORGANISM: Homo sapiens

<400> SEQUENCE: 5

```
cgtataggag gaccgtgtag gccttcctgt cccgggcctt gccagcggcc agcccgatga      60
aggagctccc tcgcaggggg tagcctccga aggagaagac gtgggagtgg tcggcagtga     120
cgaggctcag cgtgtcctcc tcgctggtga gctggcccgc cctctcaatg gcgtcgtcga     180
acatgatcgt ctcagtcagt gcccggtaag ccctgctttc atgatgacca tggtcgatgc     240
gaccaccctc cacgaagagg aagaagccgc gggggtgtct gctcagcagg               290
```

<210> SEQ ID NO 6
<211> LENGTH: 288
<212> TYPE: DNA
<213> ORGANISM: Homo sapiens

<400> SEQUENCE: 6

```
cgcagggcag cctctgtcat ctccatcagg gaggggtcca gtgtggagtc tcggtggatc      60
tcgtatttca tgtctccagg ctcaaagaga cccatgagat gggtcacaga cgggtccagg     120
gaagcctgca tgagctcagt gcggttccac acgtaccggg caccctggcg ttcgccgagc     180
cattcctgca ccagattctt cccgtccagc ctggtccacc cttggctgta gtcatctggg     240
tactcagggt ctggggttcc catgcgaaac atgtactttc ggcctcca                 288
```

<210> SEQ ID NO 7
<211> LENGTH: 3603
<212> TYPE: DNA
<213> ORGANISM: Homo sapiens

<400> SEQUENCE: 7

```
atgctttggt gggaagaagt agaggactgt tatgaaagag aagatgttca aagaaaaca       60
ttcacaaaat gggtaaatgc acaatttttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc tcgattcaa gagctatgcc    900
tacacacagg ctgcttatgt caccaccctct gaccctacac ggagcccatt tccttcacag   960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
```

```
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaagaaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgtcacc accactcagc catcactaac acagacaact   2040
gtaatggaaa cagtaactac ggtgaccaca agggaacaga tcctggtaaa gcatgctcaa   2100
gaggaacttc caccaccacc tccccaaaag aagaggcaga ttactgtgga ttctgaaatt   2160
aggaaaaggt tggatgttga tataactgaa cttcacagct ggattactcg ctcagaagct   2220
gtgttgcaga gtcctgaatt tgcaatcttt cggaaggaag caacttctc agacttaaaa   2280
gaaaagtca atgccataga gcgagaaaaa gctgagaagt tcagaaaact gcaagatgcc   2340
agcagatcag ctcaggccct ggtggaacag atggtgaatg agggtgttaa tgcagatagc   2400
atcaaacaag cctcagaaca actgaacagc cggtggatcg aattctgcca gttgctaagt   2460
gagagactta actggctgga gtatcagaac aacatcatcg ctttctataa tcagctacaa   2520
caattggagc agatgacaac tactgctgaa aactggttga aaatccaacc caccacccca   2580
tcagagccaa cagcaattaa aagtcagtta aaaatttgta aggatgaagt caaccggcta   2640
tcaggtcttc aacctcaaat tgaacgatta aaaattcaaa gcatagccct gaaagagaaa   2700
ggacaaggac ccatgttcct ggatgcagac tttgtggcct ttacaaatca tttttaagcaa  2760
gtcttttctg atgtgcaggc cagagagaaa gagctacaga caattttttga cacttttgcca  2820
ccaatgcgct atcaggagac catgagtgcc atcaggacat gggtccagca gtcagaaacc   2880
aaactctcca tacctcaact tagtgtcacc gactatgaaa tcatggagca gagactcggg   2940
gaattgcagg ctttacaaag ttctctgcaa gagcaacaaa gtggcctata ctatctcagc   3000
accactgtga aagagatgtc gaagaaagcg ccctctgaaa ttagccggaa atatcaatca   3060
gaatttgaag aaattgaggg acgctggaag aagctctcct cccagctggt tgagcattgt   3120
caaaagctag aggagcaaat gaataaactc cgaaaaattc agaatcacat acaaaccctg   3180
aagaaatgga tggctgaagt tgatgttttt ctgaaggagg aatggcctgc ccttggggat   3240
tcagaaattc taaaaaagca gctgaaacag tgcagacttt tagtcagtga tattcagaca   3300
attcagccca gtctaaacag tgtcaatgaa ggtgggcaga agataaagaa tgaagcagag   3360
ccagagtttg cttcgagact tgagacagaa ctcaaagaac ttaacactca gtgggatcac   3420
atgtgccaac aggtctatgc cagaaaggag gccttgaagg gaggtttgga gaaaactgta   3480
```

-continued

| | |
|---|---|
| agcctccaga aagatctatc agagatgcac gaatggatga cacaagctga agaagagtat | 3540 |
| cttgagagag attttgaata taaaactcca gatgaattac agaaagcagt tgaagagatg | 3600 |
| aag | 3603 |

<210> SEQ ID NO 8
<211> LENGTH: 3495
<212> TYPE: DNA
<213> ORGANISM: Homo sapiens

<400> SEQUENCE: 8

| | |
|---|---|
| agagctaaag aagaggccca acaaaaagaa gcgaaagtga aactccttac tgagtctgta | 60 |
| aatagtgtca tagctcaagc tccacctgta gcacaagagg ccttaaaaaa ggaacttgaa | 120 |
| actctaacca ccaactacca gtggctctgc actaggctga atgggaaatg caagactttg | 180 |
| gaagaagttt gggcatgttg gcatgagtta ttgtcatact tggagaaagc aaacaagtgg | 240 |
| ctaaatgaag tagaatttaa acttaaaacc actgaaaaca ttcctggcgg agctgaggaa | 300 |
| atctctgagg tgctagattc acttgaaaat ttgatgcgac attcagagga taacccaaat | 360 |
| cagattcgca tattggcaca gaccctaaca gatggcggag tcatggatga gctaatcaat | 420 |
| gaggaacttg agacatttaa ttctcgttgg agggaactac atgaagaggc tgtaaggagg | 480 |
| caaaagttgc ttgaacagag catccagtct gcccaggaga ctgaaaaatc cttacactta | 540 |
| atccaggagt ccctcacatt cattgacaag cagttggcag cttatattgc agacaaggtg | 600 |
| gacgcagctc aaatgcctca ggaagcccag aaaatccaat ctgatttgac aagtcatgag | 660 |
| atcagtttag aagaaatgaa gaaacataat caggggaagg aggctgccca agagtcctg | 720 |
| tctcagattg atgttgcaca gaaaaaatta caagatgtct ccatgaagtt tcgattattc | 780 |
| cagaaaccag ccaattttga gctgcgtcta caagaaagta gatgattttt agatgaagtg | 840 |
| aagatgcact tgcctgcatt ggaaacaaag agtgtggaac aggaagtagt acagtcacag | 900 |
| ctaaatcatt gtgtgaactt gtataaaagt ctgagtgaag tgaagtctga agtggaaatg | 960 |
| gtgataaaga ctggacgtca gattgtacag aaaaagcaga cggaaaatcc caaagaactt | 1020 |
| gatgaaagag taacagcttt gaaattgcat tataatgagc tgggagcaaa ggtaacagaa | 1080 |
| agaaagcaac agttggagaa atgcttgaaa ttgtcccgta agatgcgaaa ggaaatgaat | 1140 |
| gtcttgacag aatggctggc agctacagat atggaattga caaagagatc agcagttgaa | 1200 |
| ggaatgccta gtaatttgga ttctgaagtt gcctggggaa aggctactca aaaagagatt | 1260 |
| gagaaacaga aggtgcacct gaagagtatc acagaggtag gagaggcctt gaaaacagtt | 1320 |
| ttgggcaaga aggagacgtt ggtggaagat aaactcagtc ttctgaatag taactggata | 1380 |
| gctgtcacct cccgagcaga agagtggtta aatcttttgt tggaatacca gaaacacatg | 1440 |
| gaaactttg accagaatgt ggaccacatc acaaagtgga tcattcaggc tgacacactt | 1500 |
| ttggatgaat cagagaaaaa gaaacccag caaaagaag acgtgcttaa gcgtttaaag | 1560 |
| gcagaactga atgacatacg cccaaaggtg gactctacac gtgaccaagc agcaaacttg | 1620 |
| atggcaaacc gcggtgacca ctgcaggaaa ttagtagagc cccaaatctc agagctcaac | 1680 |
| catcgatttg cagccatttc acacagaatt aagactggaa aggcctccat tcctttgaag | 1740 |
| gaattggagc agtttaactc agatatacaa aaattgcttg aaccactgga ggctgaaatt | 1800 |
| cagcaggggg tgaatctgaa agaggaagac ttcaataaag atatgaatga agacaatgag | 1860 |
| ggtactgtaa aagaattgtt gcaaagagga gacaacttac aacaaagaat cacagatgag | 1920 |
| agaaagagag aggaaataaa gataaaacag cagctgttac agacaaaaca taatgctctc | 1980 |

```
aaggatttga ggtctcaaag aagaaaaaag gctctagaaa tttctcatca gtggtatcag    2040
tacaagaggc aggctgatga tctcctgaaa tgcttggatg acattgaaaa aaaattagcc    2100
agcctacctg agcccagaga tgaaaggaaa ataaaggaaa ttgatcggga attgcagaag    2160
aagaaagagg agctgaatgc agtgcgtagg caagctgagg gcttgtctga ggatggggcc    2220
gcaatggcag tggagccaac tcagatccag ctcagcaagc gctggcggga aattgagagc    2280
aaatttgctc agtttcgaag actcaacttt gcacaaattc acactgtccg tgaagaaacg    2340
atgatggtga tgactgaaga catgcctttg gaaatttctt atgtgccttc tacttatttg    2400
actgaaatca ctcatgtctc acaagcccta ttagaagtgg aacaacttct caatgctcct    2460
gacctctgtg ctaaggactt tgaagatctc tttaagcaag aggagtctct gaagaatata    2520
aaagatagtc tacaacaaag ctcaggtcgg attgacatta ttcatagcaa gaagacagca    2580
gcattgcaaa gtgcaacgcc tgtggaaagg gtgaagctac aggaagctct ctcccagctt    2640
gatttccaat gggaaaaagt taacaaaatg tacaaggacc gacaagggcg atttgacaga    2700
tctgttgaga atggcggcg ttttcattat gatataaaga tatttaatca gtggctaaca    2760
gaagctgaac agtttctcag aaagacacaa attcctgaga attgggaaca tgctaaatac    2820
aaatggtatc ttaaggaact ccaggatggc attgggcagc ggcaaactgt tgtcagaaca    2880
ttgaatgcaa ctggggaaga ataaattcag caatcctcaa aaacagatgc cagtattcta    2940
caggaaaaat tgggaagcct gaatctgcgg tggcaggagg tctgcaaaca gctgtcagac    3000
agaaaaaaga ggctagaaga acaaaagaat atcttgtcag aatttcaaag agatttaaat    3060
gaatttgttt tatggttgga ggaagcagat aacattgcta gtatcccact tgaacctgga    3120
aaagagcagc aactaaaaga aaagcttgag caagtcaagt tactggtgga agagttgccc    3180
ctgcgccagg gaattctcaa acaattaaat gaaactggag gacccgtgct tgtaagtgct    3240
cccataagcc cagaagagca agataaactt gaaaataagc tcaagcagac aaatctccag    3300
tggataaagg tttccagagc tttacctgag aaacaaggag aaattgaagc tcaaataaaa    3360
gaccttgggc agcttgaaaa aaagcttgaa gaccttgaag agcagttaaa tcatctgctg    3420
ctgtggttat ctcctattag gaatcagttg gaaatttata accaaccaaa ccaagaagga    3480
ccatttgacg ttcag                                                    3495
```

<210> SEQ ID NO 9
<211> LENGTH: 3936
<212> TYPE: DNA
<213> ORGANISM: Homo sapiens

<400> SEQUENCE: 9

```
gaaactgaaa tagcagttca agctaaacaa ccggatgtgg aagagatttt gtctaagggg     60
cagcatttgt acaaggaaaa accagccact cagccagtga agaggaagtt agaagatctg    120
agctctgagt ggaaggcggt aaaccgttta cttcaagagc tgagggcaaa gcagcctgac    180
ctagctcctg gactgaccac tattggagcc tctcctactc agactgttac tctggtgaca    240
caacctgtgg ttactaagga aactgccatc tccaaactag aaatgccatc ttccttgatg    300
ttggaggtac ctgctctggc agatttcaac cgggcttgga cagaacttac cgactggctt    360
tctctgcttg atcaagttat aaaatcacag agggtgatgg tgggtgacct tgaggatatc    420
aacgagatga tcatcaagca gaaggcaaca atgcaggatt ggaacagag gcgtccccag    480 ttggaagaac tcattaccgc tgcccaaaat ttgaaaaaca agaccagcaa tcaagaggct    540
agaacaatca ttacggatcg aattgaaaga attcagaatc agtgggatga agtacaagaa    600
```

```
caccttcaga accggaggca acagttgaat gaaatgttaa aggattcaac acaatggctg    660
gaagctaagg aagaagctga gcaggtctta ggacaggcca gagccaagct tgagtcatgg    720
aaggagggtc cctatacagt agatgcaatc caaaagaaaa tcacagaaac caagcagttg    780
gccaaagacc tccgccagtg gcagacaaat gtagatgtgg caaatgactt ggccctgaaa    840
cttctccggg attattctgc agatgatacc agaaaagtcc acatgataac agagaatatc    900
aatgcctctt ggagaagcat tcataaaagg gtgagtgagc gagaggctgc tttggaagaa    960
actcatagat tactgcaaca gttcccctg gacctggaaa agtttcttgc ctggcttaca    1020
gaagctgaaa caactgccaa tgtcctacag gatgctaccc gtaaggaaag gctcctagaa    1080
gactccaagg gagtaaaaga gctgatgaaa caatggcaag acctccaagg tgaaattgaa    1140
gctcacacag atgtttatca aacctggat gaaaacagcc aaaaaatcct gagatccctg    1200
gaaggttccg atgatgcagt cctgttacaa agacgtttgg ataacatgaa cttcaagtgg    1260
agtgaacttc ggaaaaagtc tctcaacatt aggtcccatt tggaagccag ttctgaccag    1320
tggaagcgtc tgcacctttc tctgcaggaa cttctggtgt ggctacagct gaaagatgat    1380
gaattaagcc ggcaggcacc tattggaggc gactttccag cagttcagaa gcagaacgat    1440
gtacataggg ccttcaagag ggaattgaaa actaaagaac ctgtaatcat gagtactctt    1500
gagactgtac gaatatttct gacagagcag cctttggaag gactagagaa actctaccag    1560
gagcccagag agctgcctcc tgaggagaga gcccagaatg tcactcggct tctacgaaag    1620
caggctgagg aggtcaatac tgagtgggaa aaattgaacc tgcactccgc tgactggcag    1680
agaaaaatag atgagaccct tgaaagactc caggaacttc aagaggccac ggatgagctg    1740
gacctcaagc tgcgccaagc tgaggtgatc aagggatcct ggcagcccgt gggcgatctc    1800
ctcattgact ctctccaaga tcacctcgag aaagtcaagg cacttcgagg agaaattgcg    1860
cctctgaaag agaacgtgag ccacgtcaat gaccttgctc gccagcttac cactttgggc    1920
attcagctct caccgtataa cctcagcact ctggaagacc tgaacaccag atggaagctt    1980
ctgcaggtgg ccgtcgagga ccgagtcagg cagctgcatg aagcccacag ggactttggt    2040
ccagcatctc agcactttct ttccacgtct gtccagggtc cctgggagag agccatctcg    2100
ccaaacaaag tgccctacta tatcaaccac gagactcaaa caacttgctg ggaccatccc    2160
aaaatgacag agctctacca gtctttagct gacctgaata atgtcagatt ctcagcttat    2220
aggactgcca tgaaactccg aagactgcag aaggcccttt gcttggatct cttgagcctg    2280
tcagctgcat gtgatgcctt ggaccagcac aacctcaagc aaaatgacca gcccatggat    2340
atcctgcaga ttattaattg tttgaccact atttatgacc gcctggagca agagcacaac    2400
aatttggtca acgtccctct ctgcgtggat atgtgtctga actggctgct gaatgtttat    2460
gatacgggac gaacagggag gatccgtgtc ctgtcttta aaactggcat catttccctg    2520
tgtaaagcac atttggaaga caagtacaga tacctttca agcaagtggc aagttcaaca    2580
ggattttgtg accagcgcag gctgggcctc cttctgcatg attctatcca aattccaaga    2640
cagttgggtg aagttgcatc ctttgggggc agtaacattg agccaagtgt ccggagctgc    2700
ttccaatttg ctaataataa gccagagatc gaagcggccc tcttcctaga ctggatgaga    2760
ctggaacccc agtccatggt gtggctgccc gtcctgcaca gagtggctgc tgcagaaact    2820
gccaagcatc aggccaaatg taacatctgc aaagagtgtc caatcattgg attcaggtac    2880
aggagtctaa agcactttaa ttatgacatc tgccaaagct gctttttttc tggtcgagtt    2940
gcaaaaggcc ataaaatgca ctatcccatg gtggaatatt gcactccgac tacatcagga    3000
```

-continued

```
gaagatgttc gagactttgc caaggtacta aaaacaaat ttcgaaccaa aaggtatttt    3060
gcgaagcatc cccgaatggg ctacctgcca gtgcagactg tcttagaggg ggacaacatg    3120
gaaacgccag tagattctgc gcctgcctcg tcccctcagc tttcacacga tgatactcat    3180
tcacgcattg aacattatgc tagcaggcta gcagaaatgg aaaacagcaa tggatcttat    3240
ctaaatgata gcatctctcc taatgagagc atagatgatg aacatttgtt aatccagcat    3300
tactgccaaa gtttgaacca ggactccccc ctgagccagc ctcgtagtcc tgcccagatc    3360
ttgatttcct tagagagtga ggaaagaggg gagctagaga gaatcctagc agatcttgag    3420
gaagaaaaca ggaatctgca agcagaatat gaccgtctaa agcagcagca cgaacataaa    3480
ggcctgtccc cactgccgtc ccctcctgaa atgatgccca cctctcccca gagtccccgg    3540
gatgctgagc tcattgctga ggccaagcta ctgcgtcaac acaaaggccg cctggaagcc    3600
aggatgcaaa tcctggaaga ccacaataaa cagctggagt cacagttaca caggctaagg    3660
cagctgctgg agcaacccca ggcagaggcc aaagtgaatg gcacaacggt gtcctctcct    3720
tctacctctc tacagaggtc cgacagcagt cagcctatgc tgctccgagt ggttggcagt    3780
caaacttcgg actccatggg tgaggaagat cttctcagtc ctccccagga cacaagcaca    3840
gggttagagg aggtgatgga gcaactcaac aactccttcc ctagttcaag aggaagaaat    3900
acccctggaa agccaatgag agaggacaca atgtag                              3936
```

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gcgcgctagc gggatcgaaa gagcctgcta aagc                                 34

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
gcgcggatcc atgcggtacc tcagaaacgc                                      30

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
gaagactctt gcgtttctg                                                  19

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
gcgctctaga cgggcagaca tggcctgccc gg                                   32

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
aggtctgcat gcgtgatcct aggtgg                                    26

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
atattagcat gcaccacgga ccgccc                                    26

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gccagagcca agcttgagtc atgg                                      24

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gatacttact tgccattgtt tcatcag                                   27

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
tctccacagg acctccaagg tgaaattg                                  28

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ccacctgcag aagcttccat ctgg                                      24

<210> SEQ ID NO 20
<211> LENGTH: 29
<212> TYPE: DNA
<213> ORGANISM: Artificial Sequence
<220> FEATURE:
<223> OTHER INFORMATION: Primer

```
<400> SEQUENCE: 20
caatggcaag taagtatcaa ggttacaag                                              29

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
ttggaggtcc tgtggagaga aaggcaaag                                              29
```